(12) United States Patent
Watanabe et al.

(10) Patent No.: US 8,431,323 B2
(45) Date of Patent: Apr. 30, 2013

(54) FLUORINATED MONOMER OF CYCLIC ACETAL STRUCTURE, POLYMER, RESIST PROTECTIVE COATING COMPOSITION, RESIST COMPOSITION, AND PATTERNING PROCESS

(75) Inventors: Takeru Watanabe, Joetsu (JP); Satoshi Shinachi, Joetsu (JP); Takeshi Kinsho, Joetsu (JP); Koji Hasegawa, Joetsu (JP); Yuji Harada, Joetsu (JP); Jun Hatakeyama, Joetsu (JP); Kazunori Maeda, Joetsu (JP); Tomohiro Kobayashi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 582 days.

(21) Appl. No.: 12/608,556

(22) Filed: Oct. 29, 2009

(65) Prior Publication Data
US 2010/0112482 A1     May 6, 2010

(30) Foreign Application Priority Data

Oct. 30, 2008  (JP) .................................. 2008-279212
Oct. 30, 2008  (JP) .................................. 2008-279224
Oct. 30, 2008  (JP) .................................. 2008-279231

(51) Int. Cl.
| G03F 7/039 | (2006.01) |
| G03F 7/11  | (2006.01) |
| G03F 7/20  | (2006.01) |
| G03F 7/30  | (2006.01) |
| G03F 7/38  | (2006.01) |

(52) U.S. Cl.
USPC .................. 430/270.1; 430/271.1; 430/273.1; 430/325; 430/326; 430/311; 430/330; 430/907; 430/942; 430/919; 430/921; 526/242; 526/247; 526/266; 526/270

(58) Field of Classification Search .......................... None
See application file for complete search history.

(56) References Cited

U.S. PATENT DOCUMENTS

| 5,541,037 | A | 7/1996 | Hatakeyama et al. |
| 6,312,867 | B1 | 11/2001 | Kinsho et al. |
| 6,869,744 | B2 | 3/2005 | Hatakeyama |
| 7,244,545 | B2 | 7/2007 | Takebe et al. |
| 7,455,952 | B2 | 11/2008 | Hatakeyama et al. |
| 7,531,289 | B2 | 5/2009 | Kinsho et al. |
| 7,537,880 | B2 | 5/2009 | Harada et al. |
| 7,592,407 | B2 | 9/2009 | Harada et al. |
| 2006/0094817 | A1* | 5/2006 | Harada et al. .................. 524/544 |
| 2007/0122736 | A1 | 5/2007 | Hatakeyama et al. |
| 2008/0032202 | A1 | 2/2008 | Ishizuka et al. |
| 2008/0090172 | A1 | 4/2008 | Hatakeyama et al. |
| 2008/0118860 | A1* | 5/2008 | Harada et al. .............. 430/270.1 |
| 2009/0053650 | A1 | 2/2009 | Irie |
| 2009/0130592 | A1 | 5/2009 | Wang |
| 2009/0142715 | A1 | 6/2009 | Araki et al. |
| 2009/0181323 | A1 | 7/2009 | Kanda et al. |

FOREIGN PATENT DOCUMENTS

| JP | 60-38821 A | 2/1985 |
| JP | 62-62520 A | 3/1987 |
| JP | 62-62521 A | 3/1987 |
| JP | 6-273926 A | 9/1994 |
| JP | 9-246173 A | 9/1997 |
| JP | 2803549 B2 | 9/1998 |
| JP | 2000-336121 A | 12/2000 |
| JP | 2002-99090 A | 4/2002 |
| JP | 2005-264131 A | 9/2005 |
| JP | 2006-48029 A | 2/2006 |
| JP | 2006-91798 A | 4/2006 |
| JP | 2006-124314 A | 5/2006 |
| JP | 2006-133716 A | 5/2006 |
| JP | 2006-152255 A | 6/2006 |
| JP | 2006-309245 A | 11/2006 |
| JP | 2007-140446 A | 6/2007 |
| JP | 2007-187887 A | 7/2007 |
| JP | 2008-111103 A | 5/2008 |
| JP | 2008-122932 A | 5/2008 |
| KR | 10-2008-0031643 A | 4/2008 |
| KR | 10-2008-0034789 A | 4/2008 |
| WO | WO 2005/042453 A1 | 5/2005 |
| WO | WO 2005/069676 A1 | 7/2005 |

OTHER PUBLICATIONS

Japanese Office Action, dated Apr. 13, 2011, for Japanese Application No. 2008-279212.
Allen et al., "Design of Protective Topcoats for Immersion Lithography", Journal of Photopolymer Science and Technology, 2005, vol. 18, No. 5. p. 615-619.
Hirayama, "Resist and Cover Material Investigation for Immersion Lithography", 2nd Immersion Workshop, Jul. 11, 2003.
Ito et al., "Aliphatic platforms for the design of 157nm chemically amplified resists", 2002, Proc. SPIE, vol. 4690, p. 18.

(Continued)

*Primary Examiner* — Sin J. Lee
(74) *Attorney, Agent, or Firm* — Birch, Stewart, Kolasch & Birch, LLP

(57) ABSTRACT

A fluorinated monomer of cyclic acetal structure has formula (1) wherein R is a $C_1$-$C_{20}$ alkyl group which may be substituted with halogen or separated by oxygen or carbonyl, and Z is a divalent organic group which forms a ring with alkylenoxy and contains a polymerizable unsaturated group. A polymer derived from the fluorinated monomer may be endowed with appropriate water repellency, water sliding property, lipophilicity, acid lability and hydrolyzability and is useful in formulating a protective coating composition and a resist composition.

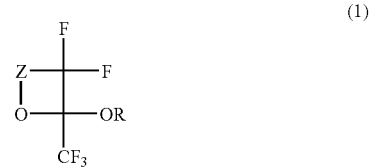

(1)

28 Claims, No Drawings

OTHER PUBLICATIONS

Lin, "Semiconductor Foundry, Lithography, and Partners", Micropatterning Division, TSMC, Inc., 2002, Proc. SPIE, vol. 4690, xxix.

Murase et al., "Characterization of molecular interfaces in hydrophobic systems", Progress in Organic Coatings, 1997, 31, p. 97.

Murase et al., "Neuer Begriff und ein Nano-Hybrid System für Hydrophobie", XXIV FATIPEC Congress Book, 1997, vol. 1 B, p. 15.

Nakano et al., "Defectivity data taken with a full-field immersion exposure tool", 2nd International symposium on Immersion Lithography. Sep. 12-15, 2005, Slide 1-27.

Owa et al., "Immersion lithography; its potential performance and issues", 2003, Proceedings of SPIE, vol. 5040, p. 724.

Sanders et al., "New materials for surface energy control of 193nm photoresists", 4th International symposium on Immersion Lithography, RE-04, 2006.

Shirota et al., "Development of non-topcoat resist polymers for 193-nm immersion lithography", Proc. SPIE, 2007, vol. 6519, p. 651905-1-651905-11.

* cited by examiner

FLUORINATED MONOMER OF CYCLIC ACETAL STRUCTURE, POLYMER, RESIST PROTECTIVE COATING COMPOSITION, RESIST COMPOSITION, AND PATTERNING PROCESS

CROSS-REFERENCE TO RELATED APPLICATION

This non-provisional application claims priority under 35 U.S.C. §119(a) on Patent Application Nos. 2008-279212, 2008-279224 and 2008-279231 filed in Japan on Oct. 30, 2008, Oct. 30, 2008 and Oct. 30, 2008, respectively, the entire contents of which are hereby incorporated by reference.

TECHNICAL FIELD

This invention relates to novel fluorinated monomers of cyclic acetal structure capable of forming polymers which are fully transparent over a wide spectrum ranging from visible light to wavelength 200 nm or shorter and fully water repellent, so that the monomers are useful as raw materials for the synthesis of opto-functional materials and coating materials. Because of high transparency to ArF laser radiation and a possible choice of a proper structure so as to tailor properties including water repellency, lipophilicity, acid lability, and hydrolyzability, the polymers are useful as components for use in ArF laser immersion lithography such as photoresist additives and protective coating materials.

This invention generally relates to a photolithography process for the microfabrication of semiconductor devices, and particularly to an immersion photolithography process involving directing ArF excimer laser radiation of wavelength 193 nm from a projection lens toward a resist-coated substrate, with a liquid (e.g., water) intervening between the lens and the substrate. More particularly, it relates to a resist protective coating composition used to form a protective coating on a resist film for protection in the immersion photolithography, and a process for forming a pattern using the same. It also relates to a resist composition comprising the polymer, and a patterning process using the resist composition.

BACKGROUND ART

In the recent drive for higher integration and operating speeds in LSI devices, the pattern rule is made drastically finer. The background supporting such a rapid advance is a reduced wavelength of the light source for exposure. The change-over from i-line (365 nm) of a mercury lamp to shorter wavelength KrF laser (248 nm) enabled mass-scale production of dynamic random access memories (DRAM) with an integration degree of 64 MB (processing feature size $\leq 0.25$ μm). To establish the micropatterning technology necessary for the fabrication of DRAM with an integration degree of 256 MB and 1 GB or more, the lithography using ArF excimer laser (193 nm) is under active investigation. The ArF excimer laser lithography, combined with a high NA lens (NA$\leq 0.9$), is considered to comply with 65-nm node devices. For the fabrication of next 45-nm node devices, the $F_2$ laser lithography of 157 nm wavelength became a candidate. However, because of many problems including a cost and a shortage of resist performance, the employment of $F_2$ lithography was postponed. ArF immersion lithography was proposed as a substitute for the $F_2$ lithography. Efforts have been made for the early introduction of ArF immersion lithography (see Proc. SPIE, Vol. 4690, xxix, 2002).

In the ArF immersion lithography, the space between the projection lens and the wafer is filled with water and ArF excimer laser is irradiated through the water. Since water has a refractive index of 1.44 at 193 nm, pattern formation is possible even using a lens with NA of 1.0 or greater. Theoretically, it is possible to increase the NA to 1.44. The resolution is improved by an increment of NA. A combination of a lens having NA of at least 1.2 with ultra-high resolution technology suggests a way to the 45-nm node (see Proc. SPIE, Vol. 5040, p 724, 2003).

Several problems arise when a resist film is exposed in the presence of water. For example, the acid once generated from a photoacid generator and a basic compound added to the resist can be partially leached in water. As a result, pattern profile changes and pattern collapse can occur. It is also pointed out that water droplets remaining on the resist film, though in a minute volume, can penetrate into the resist film to generate defects.

These drawbacks of the ArF immersion lithography may be overcome by providing a protective coating between the resist film and water to prevent resist components from being leached out and water from penetrating into the resist film (see the 2nd Immersion Workshop, Resist and Cover Material Investigation for Immersion Lithography, 2003).

With respect to the protective coating on the photoresist film, a typical antireflective coating on resist (ARCOR) process is disclosed in JP-A 62-62520, JP-A 62-62521, and JP-A 60-38821. The ARCs are made of fluorinated compounds having a low refractive index, such as perfluoroalkyl polyethers and perfluoroalkyl amines. Since these fluorinated compounds are less compatible with organic substances, fluorocarbon solvents are used in coating and stripping of protective coatings, raising environmental and cost issues.

Other resist protective coating materials under investigation include water-soluble or alkali-soluble materials. See, for example, JP-A 6-273926, Japanese Patent No. 2803549, and J. Photopolymer Sci. and Technol., Vol. 18, No. 5, p 615, 2005. Since the alkali-soluble resist protective coating material is strippable with an alkaline developer, it eliminates a need for an extra stripping unit and offers a great cost saving. From this standpoint, great efforts have been devoted to develop water-insoluble resist protective coating materials, for example, resins having alkali-soluble groups such as fluorinated alcohol, carboxyl or sulfo groups on side chains. See WO 2005/42453, WO 2005/69676, JP-A 2005-264131, JP-A 2006-133716, and JP-A 2006-91798.

Required of the resist protective coating materials are not only the ability to prevent the generated acid and basic compound in the photoresist film from being leached out in water and to prevent water from penetrating into the resist film, but also such properties as water repellency and water sliding property. Of these properties, water repellency is improved by introducing fluorine into the resin and water sliding property is improved by combining water repellent groups of different species to form a micro-domain structure, as reported, for example, in XXIV FATIPEC Congress Book, Vol. B, p 15 (1997) and Progress in Organic Coatings, 31, p 97 (1997).

One exemplary polymer exhibiting high water sliding property and water repellency is a fluorinated ring-closing polymerization polymer having hexafluoroalcohol pendants. It is reported in Proc. SPIE, Vol. 6519, p 651905 (2007) that this polymer is further improved in water sliding property by protecting hydroxyl groups on its side chains with acid labile groups.

Although the introduction of fluorine into resins is effective not only for improving water repellency, but also for improving water sliding properties as demonstrated by sliding angle, receding contact angle or the like, excessive introduction of fluorine results in resins with a greater surface contact angle following alkaline development. In the current technology, those defects so called "blob defects" that occur on the resist film surface (especially in the unexposed area) after development are regarded problematic. A tendency is known that a resist film having higher water repellency suffers from more blob defects. Accordingly, introducing extra fluorine into resins for the purpose of enhancing water repellency and water sliding property increases a likelihood of blob defects occurring.

It is believed that blob defects are caused by water droplets remaining on the resist film surface after development. The internal energy of a water droplet on a resist film increases in the spin drying step and reaches the maximum when the water droplet completely leaves the resist film surface. At the same time as the water droplet leaves the resist film surface, the resist film surface is damaged by that energy, which is observable as blob defects.

The internal energy of a water droplet on a resist film is higher as the surface becomes more water repellent. When a protective coating with higher water repellency is disposed on a resist film, the resist surface has a greater contact angle due to intermixing between the resist film and the protective coating, increasing a likelihood of blob defects occurring. This indicates that for the purpose of suppressing the occurrence of blob defects, the surface contact angle after development must be reduced to mitigate the internal energy of a water droplet.

Application of a more hydrophilic resist protective coating may be effective for reducing the surface contact angle after development. However, such a protective coating provides a smaller receding contact angle, which interferes with high-speed scanning and allows water droplets to remain after scanning, giving rise to defects known as water marks. A resist protective coating having carboxyl or sulfo groups is proposed in U.S. Pat. No. 7,455,952 (JP-A 2006-91798). Since both carboxyl and sulfo groups are fully hydrophilic, water repellency and water sliding property worsen.

It is then proposed to form a protective coating from a blend of a first polymer having sulfo groups and a second polymer having highly water repellent hexafluoroalcohol groups such that the second polymer having hexafluoroalcohol groups is segregated at the surface of the protective coating and the first polymer having sulfo groups is segregated at the interface with the underlying resist. See 4th Immersion Symposium RE-04 New Materials for surface energy control of 193 nm photoresists, Dan Sander et al. Although this protective coating is effective in reducing blob defects, the resist pattern suffers from film slimming after development because sulfo groups bind with an amine component in the resist so that the amine component becomes depleted near the resist surface. There exists a desire for a protective coating which prevents film slimming in order to produce a rectangular profile pattern and renders more hydrophilic the resist surface after development in order to inhibit blob defects.

The resist protective coating materials discussed above are needed not only in the ArF immersion lithography, but also in the electron beam (EB) lithography. When EB lithography is performed for mask image writing, it is pointed out that the resist changes its sensitivity due to evaporation of the acid generated during image writing, evaporation of vinyl ether produced by deprotection of acetal protective groups, or the like, as discussed in JP-A 2002-99090. It is then proposed to suppress resist sensitivity variation by applying a protective coating material to form a barrier film on top of a resist film.

As means for preventing resist components from being leached out and water from penetrating into the resist film without a need for a protective coating material, it is proposed in JP-A 2006-48029, JP-A 2006-309245, and JP-A 2007-187887 to add an alkali-soluble, hydrophobic, high-molecular-weight compound as a surfactant to the resist material. This method achieves equivalent effects to the use of protective coating material because the hydrophobic compound is segregated at the resist surface during resist film formation. Additionally, this method is economically advantageous over the use of a protective film because steps of forming and stripping the protective film are unnecessary.

It is believed that independent of whether the alkali-soluble surfactant or the resist protective coating material is used, water droplets remaining on the resist film or protective film after scanning cause failure (or defects) in pattern formation. The ArF immersion lithography systems commercially available at the present are designed such that exposure is carried out by scanning the wafer-mounted stage at a speed of 300 to 550 mm/sec while water is partly held between the projection lens and the wafer. In the event of such high-speed scanning, unless the performance of the resist or protective film is sufficient, water cannot be held between the projection lens and the wafer, and water droplets are left on the surface of the resist film or protective film after scanning. Such residual droplets can cause defects to the pattern.

To eliminate defects owing to residual droplets, it is necessary to improve the flow or mobility of water (hereinafter, water sliding property) on the relevant coating film and the water repellency of the film. It is reported effective to increase the receding contact angle of the resist or protective film with water. See 2nd International Symposium on Immersion Lithography, 12-15 Sep., 2005, Defectivity data taken with a full-field immersion exposure tool, Nakano et al.

For improving the water repellency of a coating film, introduction of fluorine into a base resin is effective. For improving water sliding property, combining water-repellent groups of different species to form a microdomain structure is effective. See XXIV FATIPEC Congress Book, Vol. B, p 15 (1997) and Progress in Organic Coatings, 31, p 97 (1997). According to these reports, when a water molecule interacts with methyl and trifluoromethyl groups, it orients via its oxygen and hydrogen atoms, and the orientation distance between water and methyl is longer. Thus a resin having not only water repellent fluorinated units introduced, but also both fluoroalkyl and alkyl groups incorporated is improved in water sliding property because of a longer orientation distance of water.

One exemplary material known to have excellent water sliding property and water repellency is a copolymer of α-trifluoromethylacrylate and norbornene derivative (Proc. SPIE, Vol. 4690, p 18, 2002). While this polymer was originally developed as a highly transparent resin for $F_2$ (157 nm) lithography resist materials, it is characterized by a regular arrangement of molecules of water repellent α-trifluoromethylacrylate and norbornene derivative in a ratio of 2:1. This characteristic arrangement increases the orientation distance of water relative to the resin and improves water sliding property. In fact, when this polymer is used as the base polymer in a protective coating for immersion lithography, water sliding property is drastically improved, as described in JP-A 2007-140446 or US 20070122736.

Another example of the highly water repellent/water sliding performance material is a fluorinated ring-closing polymerization polymer having hexafluoroalcohol groups on side chains. This polymer is further improved in water sliding property by protecting hydroxyl groups on side chains with acid labile groups, as reported in Proc. SPIE. Vol. 6519, p 651905 (2007).

A material having good water sliding property performance is required not only from the standpoint of defects, but also from the standpoint of productivity. The immersion lithography needs higher throughputs than ever. For improved productivity, the exposure time must be reduced, which in turn requires high-speed scanning operation of the stage. In order to move the stage at a high speed while holding water beneath the lens, it is desired to have a resist material or resist protective film having higher water sliding property performance.

The highly water repellent/water sliding performance materials discussed above are expected to be applied not only to the ArF immersion lithography, but also to the resist material for mask blanks. Resist materials for mask blanks suffer from problems including a change of sensitivity during long-term exposure in vacuum and long-term stability after coating. With respect to the control of sensitivity changes in vacuum, an improvement is made by a combination of acid labile groups of acetal and tertiary ester types (U.S. Pat. No. 6,869,744). It is believed that after coating of a resist material, an amine component is adsorbed to the resist film surface whereby the resist varies its sensitivity or profile. A method of modifying the surface of a resist film for preventing adsorption of an amine component to the resist film has been devised.

CITATION LIST

Patent Document 1: JP-A S62-62520
Patent Document 2: JP-A S62-62521
Patent Document 3: JP-A S60-38821
Patent Document 4: JP-A H06-273926
Patent Document 5: JP 2803549
Patent Document 6: WO 2005/42453
Patent Document 7: WO 2005/69676
Patent Document 8: JP-A 2005-264131
Patent Document 9: JP-A 2006-133716
Patent Document 10: JP-A 2006-91798 (U.S. Pat. No. 7,455,952)
Patent Document 11: JP-A 2002-099090
Patent Document 12: JP-A 2006-048029
Patent Document 13: JP-A 2006-309245
Patent Document 14: JP-A 2007-187887
Patent Document 15: JP-A 2007-140446 (US 20070122736)
Patent Document 16: U.S. Pat. No. 6,869,744
Patent Document 17: JP-A 2008-111103 (U.S. Pat. No. 7,537,880, KR 20080031643)
Patent Document 18: JP-A 2008-122932 (US 2008090172, KR 20080034789)
Non-Patent Document 1: Proc. SPIE, Vol. 4690, xxix, (2002)
Non-Patent Document 2: Proc. SPIE, Vol. 5040, p 724, (2003)
Non-Patent Document 3: 2nd Immersion Workshop: Resist and Cover Material Investigation for Immersion Lithography (2003)
Non-Patent Document 4: J. Photopolymer Sci. and Technol., Vol. 18, No. 5, p 615, (2005)
Non-Patent Document 5: XXIV FATIPEC Congress Book, Vol. B, p 15 (1997)
Non-Patent Document 6: Progress in Organic Coatings, 31, p 97 (1997)
Non-Patent Document 7: Proc. SPIE, Vol. 6519, p 651905 (2007)
Non-Patent Document 8: 4th Immersion Symposium RE-04 New Materials for surface energy control of 193 nm to photoresists, Dan Sander et al.
Non-Patent Document 9: 2nd International Symposium on Immersion Lithography, 12-15 September, (2005), Defectivity data taken with a full-field immersion exposure tool, Nakano et al.
Non-Patent Document 10:Proc. SPIE, Vol. 4690, p 18, (2002)

SUMMARY OF INVENTION

An object of the present invention is to provide a novel fluorinated monomer and a polymer derived therefrom. The monomer is useful as a raw material for the production of opto-functional materials and coating materials and can be prepared from reactants which are readily available and easy to handle; the polymer has high transparency to radiation of wavelength 200 nm or shorter and improved water repellency, is designed such that any of its properties including water repellency, lipophilicity, acid lability and hydrolyzability may be tailored by a choice of a proper structure, and finds use as the materials adapted for ArF laser exposure immersion lithography such as photoresist additives and protective coating materials.

Another object is to provide a resist protective coating composition for immersion lithography which has improved water repellency and water sliding property, causes few development defects, and allows for formation of a resist pattern of satisfactory profile after development; and a pattern forming process using the protective coating composition.

A further object is to provide a resist composition for immersion lithography which has improved water repellency and water sliding property, causes few development defects, and forms a resist pattern of satisfactory profile after development; and a pattern forming process using the resist composition.

The inventors have found that fluorinated monomers of cyclic acetal structure having the general formulae (1), (2), (3), (4), (2-1), (3-1), (4-1), (2-2), (3-2), and (4-2) can be easily prepared from reactants, which are readily available and easy to handle, in high yields by the method to be described later; and that polymers resulting from polymerization of these fluorinated monomers have improved water repellency and allow their performance to be tailored by a choice of structure.

The inventors have also found that polymers of cyclic acetal structure having the general formulae (5) to (7) have sufficient water repellency and water sliding property to serve as a base polymer in resist protective coating materials and allow their performance to be tailored by a choice of structure. When this polymer is blended with another polymer containing a sulfonic acid amine salt within recurring units, a resist protective coating composition is obtained which enables to form a resist pattern of good profile with no or few development defects. The polymer has high transparency to radiation of wavelength 200 nm or shorter, is designed such that any of its properties including water repellency, lipophilicity, acid lability and hydrolyzability may be tailored by a choice of a proper structure.

The inventors have further found that the polymers having the general formulae (5) to (7) are useful as an additive polymer in resist materials.

The invention provides a fluorinated monomer, a polymer, a protective coating composition, a resist composition, and pattern forming processes using the compositions, as defined below.

[1] A fluorinated monomer of cyclic acetal structure having the general formula (1):

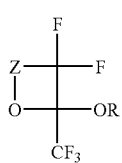

(1)

wherein R is a straight, branched or cyclic $C_1$-$C_{20}$ alkyl group in which at least one hydrogen atom may be substituted by a halogen atom or at least one methylene moiety may be substituted by an oxygen atom or carbonyl group, and Z is a divalent organic group which is attached at opposite ends to the alkylenoxy group to form a 5- or 6-membered ring and which contains a polymerizable unsaturated group.

[2] A fluorinated monomer of cyclic acetal structure having the general formula (2), (3) or (4).

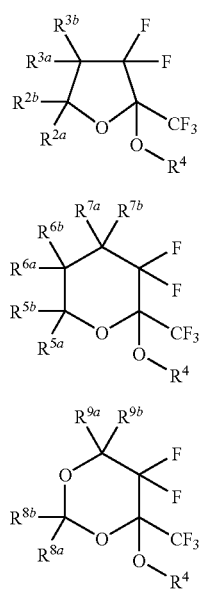

Herein $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, at least one of $R^{2a}$, $R^{2b}$, $R^{3a}$, and $R^{3b}$ is a monovalent organic group containing a polymerizable unsaturated group, or any two of $R^{2a}$, $R^{2b}$, $R^{3a}$, and $R^{3b}$ may bond together to form a ring with the carbon atom to which they are attached, with the proviso that said ring contains a polymerizable unsaturated group when the remaining groups of $R^{2a}$, $R^{2b}$, $R^{3a}$, and $R^{3b}$ which do not participate in the ring formation do not contain a polymerizable unsaturated group, $R^4$ is a straight, branched or cyclic $C_1$-$C_{20}$ alkyl group in which at least one hydrogen atom may be substituted by a halogen atom or at least one methylene moiety may be substituted by an oxygen atom or carbonyl group, $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, at least one of $R^{5a}$, $R^{5b}$, $R^{6a}$, $R^{6b}$, $R^{7a}$, and $R^{7b}$ is a monovalent organic group containing a polymerizable unsaturated group, or any two of $R^{5a}$, $R^{5b}$, $R^{6a}$, $R^{6b}$, $R^{7a}$, and $R^{7b}$ may bond together to form a ring with the carbon atom to which they are attached, with the proviso that said ring contains a polymerizable unsaturated group when the remaining groups of $R^{5a}$, $R^{5b}$, $R^{6a}$, $R^{6b}$, $R^{7a}$, and $R^{7b}$ which do not participate in the ring formation do not contain a polymerizable unsaturated group, $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, at least one of $R^{8a}$, $R^{8b}$, $R^{9a}$, and $R^{9b}$ is a monovalent organic group containing a polymerizable unsaturated group, or any two of $R^{8a}$, $R^{8b}$, $R^{9a}$, and $R^{9b}$ may bond together to form a ring with the carbon atom to which they are attached, with the proviso that said ring contains a polymerizable unsaturated group when the remaining groups of $R^{8a}$, $R^{8b}$, $R^{9a}$, and $R^{9b}$ which do not participate in the ring formation do not contain a polymerizable unsaturated group.

[3] A fluorinated monomer of cyclic acetal structure having the general formula (2-1), (3-1) or (4-1).

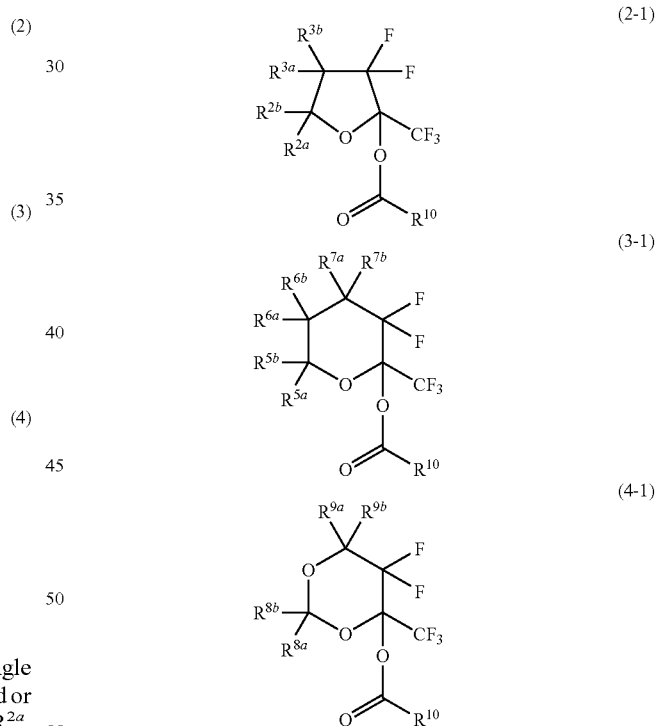

Herein $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, at least one of $R^{2a}$, $R^{2b}$, $R^{3a}$, and $R^{3b}$ is a monovalent organic group containing a polymerizable unsaturated group, or any two of $R^{2a}$, $R^{2b}$, $R^{3a}$, and $R^{3b}$ may bond together to form a ring with the carbon atom to which they are attached, with the proviso that said ring contains a polymerizable unsaturated group when the remaining groups of $R^{2a}$, $R^{2b}$, $R^{3a}$, and $R^{3b}$ which do not participate in the ring formation do not contain a polymerizable unsaturated group, $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, at least one of $R^{5a}$, $R^{5b}$, $R^{6a}$, $R^{6b}$, $R^{7a}$, and $R^{7b}$ is a monovalent organic group containing a polymerizable unsaturated group, or any two of $R^{5a}$, $R^{5b}$, $R^{6a}$, $R^{6b}$, $R^{7a}$, and $R^{7b}$ may bond together to form a ring with the carbon atom to which they are attached, with the proviso that said ring contains a polymerizable unsaturated group when the remaining groups of $R^{5a}$, $R^{5b}$, $R^{6a}$, $R^{6b}$, $R^{7a}$, and $R^{7b}$ which do not participate in the ring formation do not contain a polymerizable unsaturated group, $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, at least one of $R^{8a}$, $R^{8b}$, $R^{9a}$, and $R^{9b}$ is a monovalent organic group containing a polymerizable unsaturated group, or any two of $R^{8a}$, $R^{8b}$, $R^{9a}$, and $R^{9b}$ may bond together to form a ring with the carbon atom to which they are attached, with the proviso that said ring contains a polymerizable unsaturated group when the remaining groups of $R^{8a}$, $R^{8b}$, $R^{9a}$, and $R^{9b}$ which do not participate in the ring formation do not contain a polymerizable unsaturated group, and $R^{10}$ is a straight, branched or cyclic $C_1$-$C_{19}$ alkyl group in which at least one hydrogen atom may be substituted by a halogen atom or at least one methylene moiety may be substituted by an oxygen atom or carbonyl group.

[4] A fluorinated monomer of cyclic acetal structure having the general formula (2-2), (3-2) or (4-2).

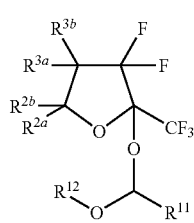

(2-2)

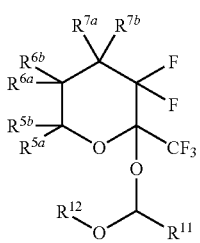

(3-2)

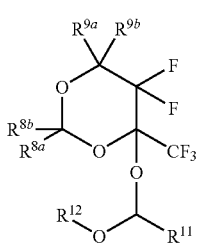

(4-2)

Herein $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, at least one of $R^{2a}$, $R^{2b}$, $R^{3a}$, and $R^{3b}$ is a monovalent organic group containing a polymerizable unsaturated group, or any two of $R^{2a}$, $R^{2b}$, $R^{3a}$, and $R^{3b}$ may bond together to form a ring with the carbon atom to which they are attached, with the proviso that said ring contains a polymerizable unsaturated group when the remaining groups of $R^{2a}$, $R^{2b}$, $R^{3a}$, and $R^{3b}$ which do not participate in the ring formation do not contain a polymerizable unsaturated group, $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, at least one of $R^{5a}$, $R^{5b}$, $R^{6a}$, $R^{6b}$, $R^{7a}$, and $R^{7b}$ is a monovalent organic group containing a polymerizable unsaturated group, or any two of $R^{5a}$, $R^{5b}$, $R^{6a}$, $R^{6b}$, $R^{7a}$, and $R^{7b}$ may bond together to form a ring with the carbon atom to which they are attached, with the proviso that said ring contains a polymerizable unsaturated group when the remaining groups of $R^{5a}$, $R^{5b}$, $R^{6a}$, $R^{6b}$, $R^{7a}$, and $R^{7b}$ which do not participate in the ring formation do not contain a polymerizable unsaturated group, $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, at least one of $R^{8a}$, $R^{8b}$, $R^{9a}$, and $R^{9b}$ is a monovalent organic group containing a polymerizable unsaturated group, or any two of $R^{8a}$, $R^{8b}$, $R^{9a}$, and $R^{9b}$ may bond together to form a ring with the carbon atom to which they are attached, with the proviso that said ring contains a polymerizable unsaturated group when the remaining groups of $R^{8a}$, $R^{8b}$, $R^{9a}$, and $R^{9b}$ which do not participate in the ring formation do not contain a polymerizable unsaturated group, $R^{11}$ is hydrogen or a straight, branched or cyclic $C_1$-$C_{18}$ alkyl group in which at least one hydrogen atom may be substituted by a halogen atom or at least one methylene moiety may be substituted by an oxygen atom or carbonyl group, and $R^{12}$ is a straight, branched or cyclic $C_1$-$C_{19}$ alkyl group in which at least one hydrogen atom may be substituted by a halogen atom or at least one methylene moiety may be substituted by an oxygen atom or carbonyl group, or $R^{11}$ and $R^{12}$ may bond together to form a cyclic structure with the carbon and oxygen atoms to which they are attached.

[5] The fluorinated monomer of cyclic acetal structure of any one of [1] to [4] wherein the polymerizable unsaturated group is a group of acrylate, methacrylate or α-trifluoromethylacrylate structure having the general formula (A):

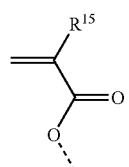

(A)

wherein $R^{15}$ is hydrogen, methyl or trifluoromethyl, and the broken line designates a valence bond.

[6] The fluorinated monomer of cyclic acetal structure of any one of [1] to [4] wherein the polymerizable unsaturated group is a group of unsaturated hydrocarbon structure having the general formula (B) or (C):

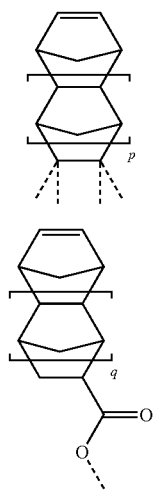

wherein p and q are each independently 1 or 0, and the broken line designates a valence bond.

[7] A polymer comprising recurring units of the general formula (5) and having a weight average molecular weight of 1,000 to 500,000.

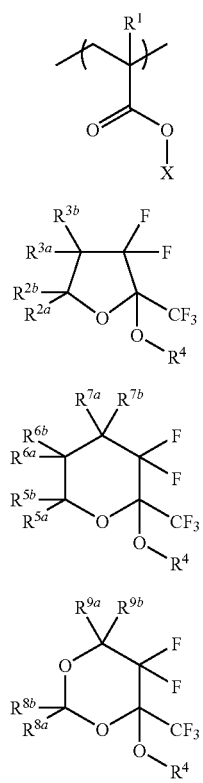

Herein $R^1$ is hydrogen, methyl or trifluoromethyl, and X is a structure having the general formula (X-1), (X-2) or (X-3), in formula (X-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (X-1) is linked to the —(C=O)—O— linkage in recurring unit (5) via any one of $R^{2a}$, $R^{2b}$, $R^{3a}$, and $R^{3b}$, in formula (X-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (X-2) is linked to the —(C=O)—O— linkage in recurring unit (5) via any one of $R^{5a}$, $R^{5b}$, $R^{6a}$, $R^{6b}$, $R^{7a}$, and $R^{7b}$, in formula (X-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (X-3) is linked to the —(C=O)—O— linkage in recurring unit (5) via any one of $R^{8a}$, $R^{8b}$, $R^{9a}$, and $R^{9b}$, $R^4$ is a straight, branched or cyclic $C_1$-$C_{20}$ alkyl group in which at least one hydrogen atom may be substituted by a halogen atom or at least one methylene moiety may be substituted by an oxygen atom or carbonyl group, with the proviso that when the structure (X-1), (X-2) or (X-3) is linked to the —(C=O)—O— linkage in recurring unit (5) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

[8] A polymer comprising recurring units of the general formula (6) and having a weight average molecular weight of 1,000 to 500,000.

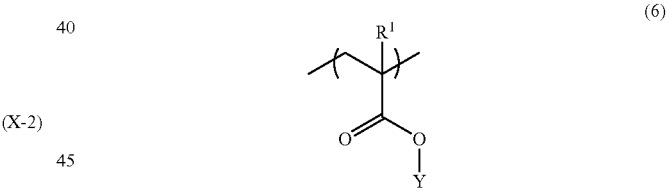

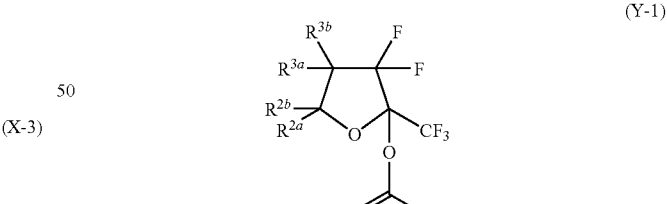

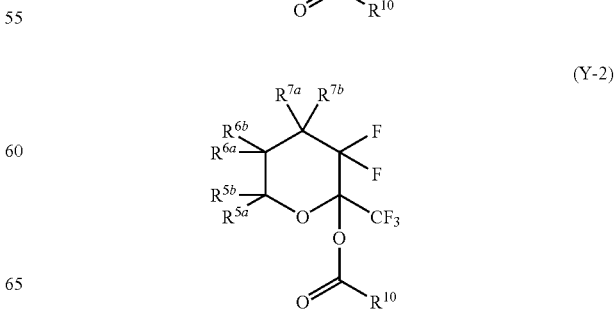

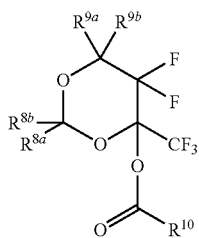

(Y-3)

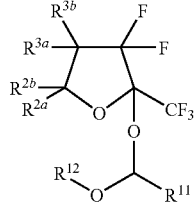

(Z-1)

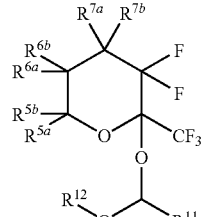

(Z-2)

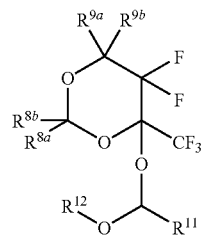

(Z-3)

Herein $R^1$ is hydrogen, methyl or trifluoromethyl, and Y is a structure having the general formula (Y-1), (Y-2) or (Y-3), in formula (Y-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (Y-1) is linked to the —(C=O)—O— linkage in recurring unit (6) via any one of $R^{2a}$, $R^{2b}$, $R^{3a}$, and $R^{3b}$, in formula (Y-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Y-2) is linked to the —(C=O)—O— linkage in recurring unit (6) via any one of $R^{5a}$, $R^{5b}$, $R^{6a}$, $R^{6b}$, $R^{7a}$, and $R^{7b}$, in formula (Y-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Y-3) is linked to the —(C=O)—O— linkage in recurring unit (6) via any one of $R^{8a}$, $R^{8b}$, $R^{9a}$, and $R^{9b}$, and $R^{10}$ is a straight, branched or cyclic $C_1$-$C_{19}$ alkyl group in which at least one hydrogen atom may be substituted by a halogen atom or at least one methylene moiety may be substituted by an oxygen atom or carbonyl group, with the proviso that when the structure (Y-1), (Y-2) or (Y-3) is linked to the —(C=O)—O— linkage in recurring unit (6) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

[9] A polymer comprising recurring units of the general formula (7) and having a weight average molecular weight of 1,000 to 500,000.

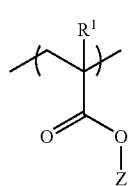

(7)

Herein $R^1$ is hydrogen, methyl or trifluoromethyl, and Z is a structure having the general formula (Z-1), (Z-2) or (Z-3), in formula (Z-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (Z-1) is linked to the —(C=O)—O— linkage in recurring unit (7) via any one of $R^{2a}$, $R^{2b}$, $R^{3a}$, and $R^{3b}$, in formula (Z-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Z-2) is linked to the —(C=O)—O— linkage in recurring unit (7) via any one of $R^{5a}$, $R^{5b}$, $R^{6a}$, $R^{6b}$, $R^{7a}$, and $R^{7b}$, in formula (Z-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Z-3) is linked to the —(C=O)—O— linkage in recurring unit (7) via any one of $R^{8a}$, $R^{8b}$, $R^{9a}$, and $R^{9b}$, $R^{11}$ is hydrogen or a straight, branched or cyclic $C_1$-$C_{18}$ alkyl group in which at least one hydrogen atom may be substituted by a halogen atom or at least one methylene moiety may be substituted by an oxygen atom or carbonyl group, $R^{12}$ is a straight, branched or cyclic $C_1$-$C_{19}$ alkyl group in which at least one hydrogen atom may be substituted by a halogen atom or at least one methylene moiety may be substituted by an oxygen atom or carbonyl group, or $R^{11}$ and $R^{12}$ may bond together to form a cyclic structure with the carbon and oxygen atoms to which they are attached, with the proviso that when the structure (Z-1), (Z-2) or (Z-3) is linked to the —(C=O)—O— linkage in recurring unit (7) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

[10] The polymer of any one of [7] to [9], further comprising recurring units of one or more type selected from the general formulae (8a) to (8f).

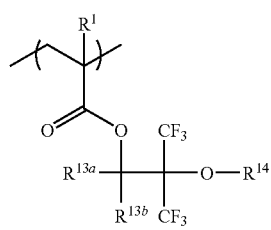
(8a)

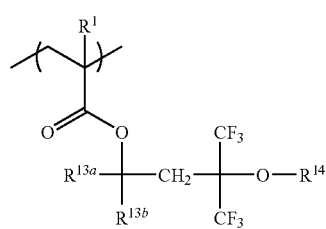
(8b)

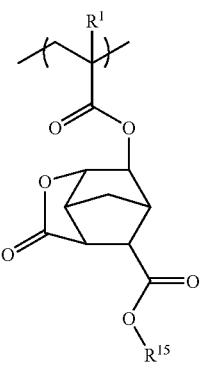
(8c)

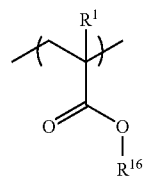
(8d)

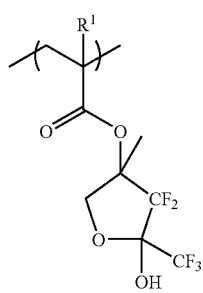
(8e)

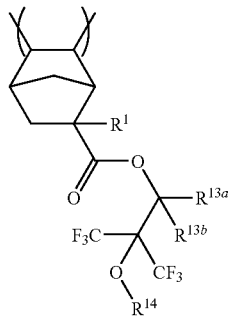
(8f)

Herein $R^1$ is hydrogen, methyl or trifluoromethyl, $R^{13a}$ and $R^{13b}$ each are hydrogen or a straight, branched or cyclic $C_1$-$C_{15}$ alkyl group, or $R^{13a}$ and $R^{13b}$ may bond together to form a ring with the carbon atom to which they are attached, $R^{14}$ is hydrogen, a straight, branched or cyclic $C_1$-$C_{15}$ alkyl or fluoroalkyl group, or an acid labile group, $R^{15}$ is a straight, branched or cyclic $C_1$-$C_{15}$ fluoroalkyl group, and $R^{16}$ is an acid labile group.

[11] A resist protective coating composition comprising a polymer comprising recurring units of the general formula (5).

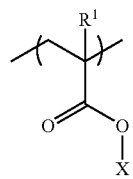
(5)

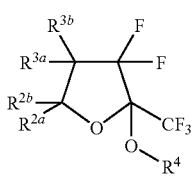
(X-1)

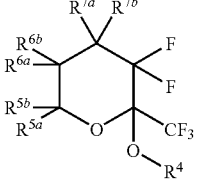
(X-2)

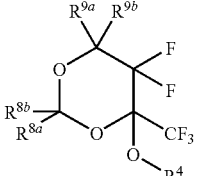
(X-3)

Herein $R^1$ is hydrogen, methyl or trifluoromethyl, and X is a structure having the general formula (X-1), (X-2) or (X-3), in formula (X-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (X-1) is linked to the —(C═O)—O— linkage in recurring unit (5) via any one of $R^{2a}$, $R^{2b}$, $R^{3a}$, and $R^{3b}$, in formula (X-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (X-2) is linked to the —(C═O)—O— linkage in recurring unit (5) via any one of $R^{5a}$, $R^{5b}$, $R^{6a}$, $R^{6b}$, $R^{7a}$, and $R^{7b}$, in formula (X-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (X-3) is linked to the —(C═O)—O— linkage in recurring unit (5) via any one of $R^{8a}$, $R^{8b}$, $R^{9a}$, and $R^{9b}$, $R^4$ is a straight, branched or cyclic $C_1$-$C_{20}$ alkyl group in which at least one hydrogen atom may be substituted by a halogen atom or at least one methylene moiety may be substituted by an oxygen atom or carbonyl group, with the proviso that when the structure (X-1), (X-2) or (X-3) is linked to the —(C═O)—O— linkage in recurring unit (5) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

[12] A resist protective coating composition comprising a polymer comprising recurring units of the general foula (6).

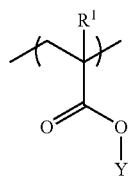

(6)

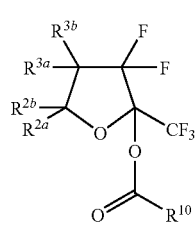

(Y-1)

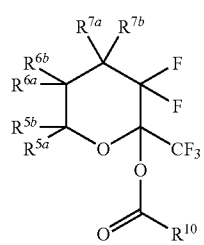

(Y-2)

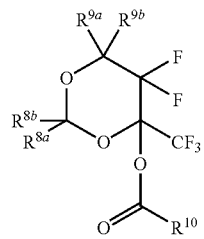

(Y-3)

Herein $R^1$ is hydrogen, methyl or trifluoromethyl, and Y is a structure having the general formula (Y-1), (Y-2) or (Y-3), in formula (Y-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (Y-1) is linked to the —(C═O)—O— linkage in recurring unit (6) via any one of $R^{2a}$, $R^{2b}$, $R^{3a}$, and $R^{3b}$, in formula (Y-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Y-2) is linked to the —(C═O)—O— linkage in recurring unit (6) via any one of $R^{5a}$, $R^{5b}$, $R^{6a}$, $R^{6b}$, $R^{7a}$, and $R^{7b}$, in formula (Y-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Y-3) is linked to the —(C═O)—O— linkage in recurring unit (6) via any one of $R^{8a}$, $R^{8b}$, $R^{9a}$, and $R^{9b}$, and $R^{10}$ is i a straight, branched or cyclic $C_1$-$C_{19}$ alkyl group in which at least one hydrogen atom may be substituted by a halogen atom or at least one methylene moiety may be substituted by an oxygen atom or carbonyl group, with the proviso that when the structure (Y-1), (Y-2) or (Y-3) is linked to the —(C═O)—O— linkage in recurring unit (6) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

[13] A resist protective coating composition comprising a polymer comprising recurring units of the general formula (7)

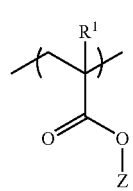

(7)

-continued

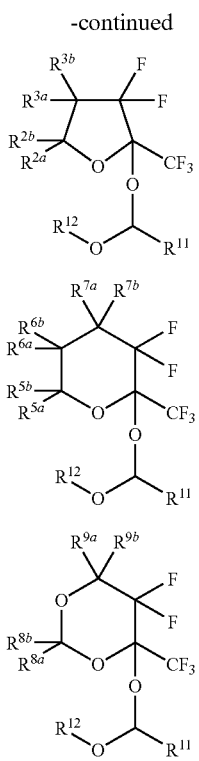

(Z-1)

(Z-2)

(Z-3)

Herein $R^1$ is hydrogen, methyl or trifluoromethyl, and Z is a structure having the general formula (Z-1), (Z-2) or (Z-3), in formula (Z-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (Z-1) is linked to the —(C═O)—O— linkage in recurring unit (7) via any one of $R^{2a}$, $R^{2b}$, $R^{3a}$, and $R^{3b}$, in formula (Z-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Z-2) is linked to the —(C═O)—O— linkage in recurring unit (7) via any one of $R^{5a}$, $R^{5b}$, $R^{6a}$, $R^{6b}$, $R^{7a}$, and $R^{7b}$, in formula (Z-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Z-3) is linked to the —(C═O)—O— linkage in recurring unit (7) via any one of $R^{8a}$, $R^{8b}$, $R^{9a}$, and $R^{9b}$, $R^{11}$ is hydrogen or a straight, branched or cyclic $C_1$-$C_{18}$ alkyl group in which at least one hydrogen atom may be substituted by a halogen atom or at least one methylene moiety may be substituted by an oxygen atom or carbonyl group, $R^{12}$ is a straight, branched or cyclic $C_1$-$C_{19}$ alkyl group in which at least one hydrogen atom may be substituted by a halogen atom or at least one methylene moiety may be substituted by an oxygen atom or carbonyl group, or $R^{11}$ and $R^{12}$ may bond together to form a cyclic structure with the carbon and oxygen atoms to which they are attached, with the proviso that when the structure (Z-1), (Z-2) or (Z-3) is linked to the —(C═O)—O— linkage in recurring unit (7) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

[14] The resist protective coating composition of any one of [11] to [13] wherein said polymer further comprises recurring units of one or more type selected from the general formulae (8a) to (8f).

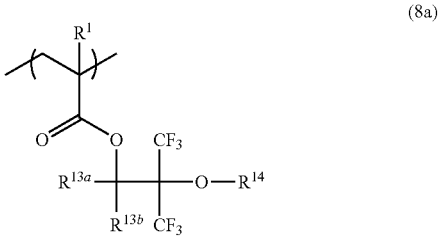

(8a)

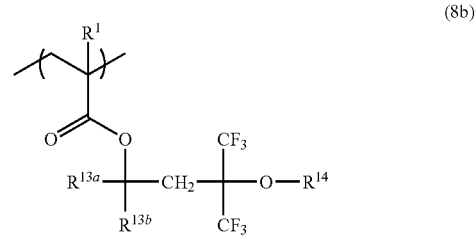

(8b)

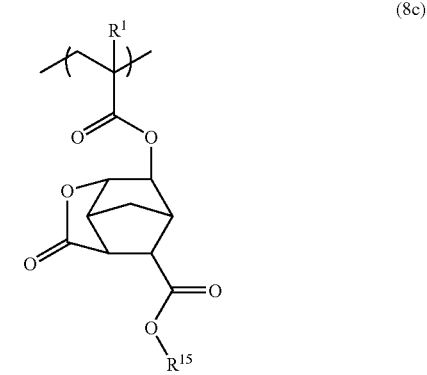

(8c)

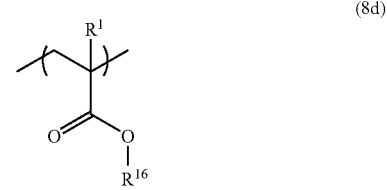

(8d)

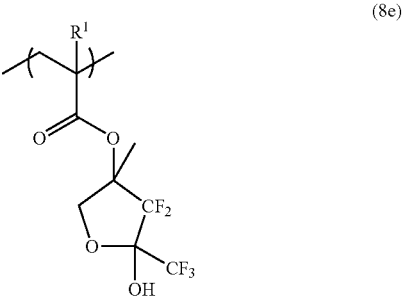

(8e)

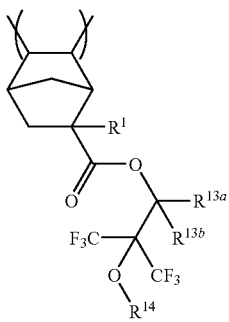

(8f)

Herein $R^1$ is hydrogen, methyl or trifluoromethyl, $R^{13a}$ and $R^{13b}$ each are hydrogen or a straight, branched or cyclic $C_1$-$C_{15}$ alkyl group, or $R^{13a}$ and $R^{13b}$ may bond together to form a ring with the carbon atom to which they are attached, $R^{14}$ is hydrogen, a straight, branched or cyclic $C_1$-$C_{15}$ alkyl or fluoroalkyl group, or an acid labile group, $R^{15}$ is a straight, branched or cyclic $C_1$-$C_{15}$ fluoroalkyl group, and $R^{16}$ is an acid labile group.

[15] The protective coating composition of any one of [11] to [14], further comprising a second polymer comprising recurring units of the general formula (9) or (10).

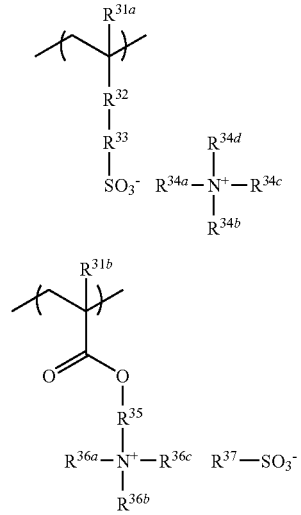

(9)

(10)

Herein $R^{31a}$ and $R^{31b}$ are hydrogen or methyl, $R^{32}$ is a single bond, $C_1$-$C_4$ alkylene, phenylene, —C(=O)—O—, or —C(=O)—NH—, $R^{33}$ is a single bond or a straight, branched or cyclic $C_1$-$C_8$ alkylene group, $R^{34a}$ to $R^{34d}$ and $R^{36a}$ to $R^{36c}$ are each independently hydrogen, a straight, branched or cyclic $C_1$-$C_{12}$ alkyl, alkenyl, oxoalkyl or oxoalkenyl group, $C_6$-$C_{20}$ aryl group, or $C_7$-$C_{12}$ aralkyl or aryloxoalkyl group, in which some or all hydrogen atoms may be substituted by alkoxy groups, $R^{34a}$ to $R^{34d}$ and $R^{36a}$ to $R^{36c}$ may contain a nitrogen atom, ether group, ester group, hydroxyl group or carboxyl group therein, any two of $R^{34a}$ to $R^{34d}$ and $R^{36a}$ to $R^{36c}$ may bond together to form a ring with the nitrogen atom to which they are attached, and when they form a ring, they are each independently a $C_3$-$C_{15}$ alkylene or a hetero-aromatic ring having the nitrogen atom therein, $R^{35}$ is a straight, branched or cyclic $C_1$-$C_8$ alkylene group, and $R^{37}$ is a straight, branched or cyclic $C_1$-$C_{20}$ alkyl group which may contain carbonyl, ester, ether or halogen, or a $C_6$-$C_{15}$ aryl group which may contain carbonyl, ester, ether, halogen, or $C_1$-$C_{15}$ alkyl or fluoroalkyl.

[16] The protective coating composition of [15], wherein the second polymer further comprises recurring units of the general formula (11):

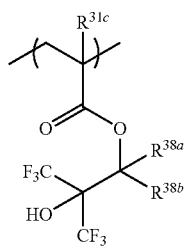

(11)

wherein $R^{31c}$ is hydrogen or methyl, $R^{38a}$ and $R^{38b}$ are hydrogen or a straight, branched or cyclic $C_1$-$C_{15}$ alkyl group, or $R^{38a}$ and $R^{38b}$ may bond together to form a ring with the carbon atom to which they are attached.

[17] The protective coating composition of any one of [11] to [16], further comprising a solvent.

[18] The protective coating composition of [17] wherein the solvent comprises an ether compound of 8 to 12 carbon atoms.

[19] The protective coating composition of [17] or [18] wherein the solvent comprises at least one ether compound of 8 to 12 carbon atoms selected from the group consisting of di-n-butyl ether, diisobutyl ether, di-sec-butyl ether, di-n-pentyl ether, diisopentyl ether, di-sec-pentyl ether, di-t-amyl ether, and di-n-hexyl ether.

[20] The protective coating composition of [18] or [19] wherein the solvent comprises a mixture of the ether compound and 0.1 to 90% by weight of an alcohol of 4 to 10 carbon atoms.

[21] A pattern forming process comprising the steps of (1) applying a resist material onto a substrate to form a photoresist film, (2) applying the resist protective coating composition of any one of [11] to [19] onto the photoresist film to form a protective coating thereon, (3) heat treating and exposing the coated substrate to high-energy radiation from a projection lens through a photomask while holding a liquid between the substrate and the projection lens, and (4) developing with a developer.

[22] The process of [21] wherein the liquid is water.

[23] The process of [21] or [22] wherein the high-energy radiation has a wavelength in the range of 180 to 250 nm.

[24] The process of any one of [21] to [23] wherein the developing step uses a liquid alkaline developer for thereby developing the photoresist film to form a resist pattern and stripping the resist protective coating therefrom at the same time.

[25] A lithography process for forming a pattern, comprising the steps of forming a protective coating on a photoresist layer disposed on a mask blank, exposing the layer structure in vacuum to electron beam, and developing, the protective coating being formed of the protective coating composition of any one of [11] to [19].

[26] A resist composition comprising (A) a polymer comprising recurring units of the general formula (5), (B) a base polymer having a structure derived from lactone ring, hydroxyl group and/or maleic anhydride, said base polymer becoming soluble in alkaline developer under the action of acid, (C) a compound capable of generating an acid upon exposure to high-energy radiation, and (D) an organic solvent.

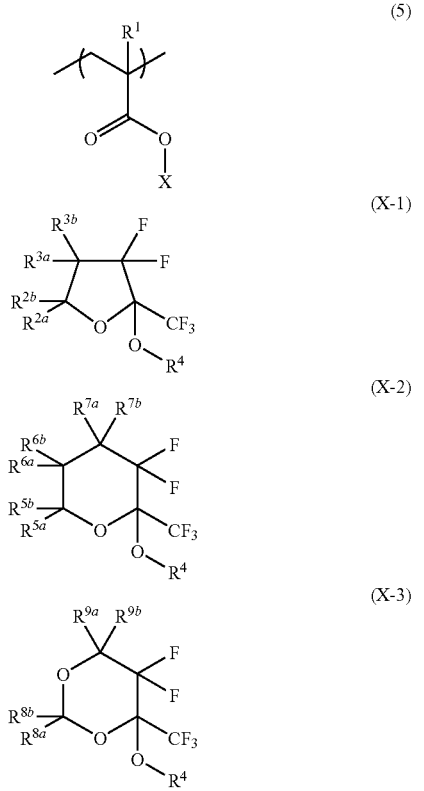

Herein $R^1$ is hydrogen, methyl or trifluoromethyl, and X is a structure having the general formula (X-1), (X-2) or (X-3), in formula (X-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (X-1) is linked to the —(C=O)—O— linkage in recurring unit (5) via any one of $R^{2a}$, $R^{2b}$, $R^{3a}$, and $R^{3b}$, in formula (X-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (X-2) is linked to the —(C=O)—O— linkage in recurring unit (5) via any one of $R^{5a}$, $R^{5b}$, $R^{6a}$, $R^{6b}$, $R^{7a}$, and $R^{7b}$, in formula (X-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (X-3) is linked to the —(C=O)—O— linkage in recurring unit (5) via any one of $R^{8a}$, $R^{8b}$, $R^{9a}$, and $R^{9b}$, $R^4$ is a straight, branched or cyclic $C_1$-$C_{20}$ alkyl group in which at least one hydrogen atom may be substituted by a halogen atom or at least one methylene moiety may be substituted by an oxygen atom or carbonyl group, with the proviso that when the structure (X-1), (X-2) or (X-3) is linked to the —(C=O)—O— linkage in recurring unit (5) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

[27] A resist composition comprising (A) a polymer comprising recurring units of the general formula (6), (B) a base polymer having a structure derived from lactone ring, hydroxyl group and/or maleic anhydride, said base polymer becoming soluble in alkaline developer under the action of acid, (C) a compound capable of generating an acid upon exposure to high-energy radiation, and (D) an organic solvent.

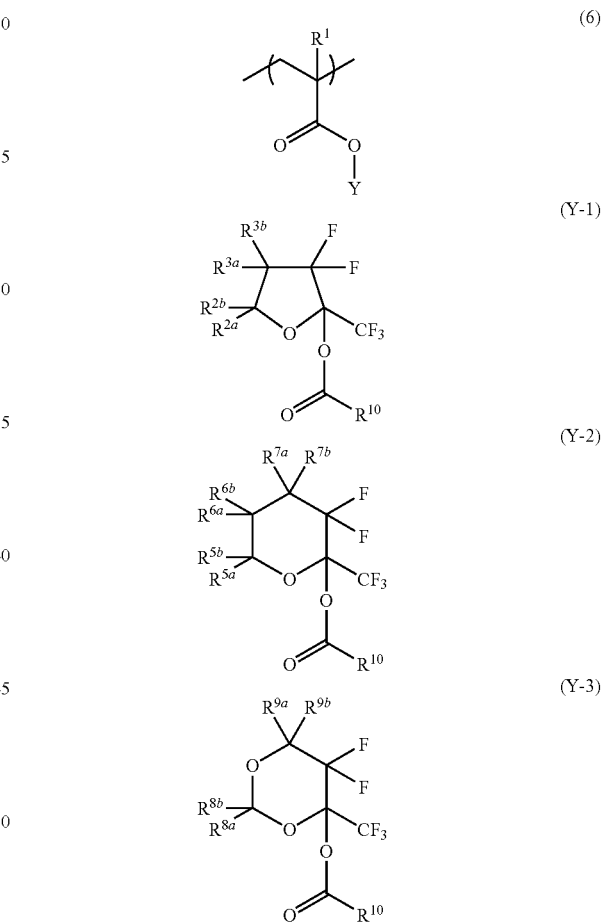

Herein $R^1$ is hydrogen, methyl or trifluoromethyl, and Y is a structure having the general formula (Y-1), (Y-2) or (Y-3), in formula (Y-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (Y-1) is linked to the —(C=O)—O— linkage in recurring unit (6) via any one of $R^{2a}$, $R^{2b}$, $R^{3a}$, and $R^{3b}$, in formula (Y-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Y-2) is linked to the —(C=O)—O— linkage in recurring unit (6) via any one of $R^{5a}$, $R^{5b}$, $R^{6a}$, $R^{6b}$, $R^{7a}$, and $R^{7b}$, in formula (Y-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Y-3) is linked to the —(C=O)—O— linkage in recurring unit (6) via any one of $R^{8a}$, $R^{8b}$, $R^{9a}$, and $R^{9b}$, and $R^{10}$ is a straight, branched or cyclic $C_1$-$C_{19}$ alkyl group in which at least one hydrogen atom may be substituted by a halogen atom or at least one methylene moiety may be substituted by an oxygen atom or carbonyl group, with the proviso that when the structure (Y-1), (Y-2) or (Y-3) is linked to the —(C=O)—O— linkage in recurring unit (6) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

[28] A resist composition comprising (A) a polymer comprising recurring units of the general formula (7), (B) a base polymer having a structure derived from lactone ring, hydroxyl group and/or maleic anhydride, said base polymer becoming soluble in alkaline developer under the action of acid, (C) a compound capable of generating an acid upon exposure to high-energy radiation, and (D) an organic solvent.

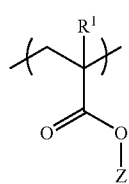

(7)

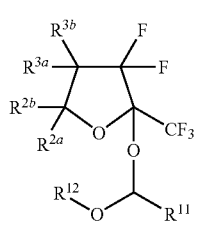

(Z-1)

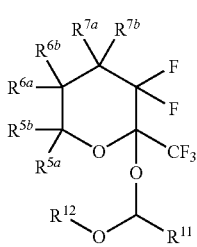

(Z-2)

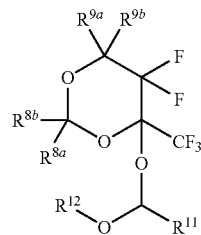

(Z-3)

Herein $R^1$ is hydrogen, methyl or trifluoromethyl, and Z is a structure having the general formula (Z-1), (Z-2) or (Z-3), in formula (Z-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (Z-1) is linked to the —(C=O)—O— linkage in recurring unit (7) via any one of $R^{2a}$, $R^{2b}$, $R^{3a}$, and $R^{3b}$, in formula (Z-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Z-2) is linked to the —(C=O)—O— linkage in recurring unit (7) via any one of $R^{5a}$, $R^{5b}$, $R^{6a}$, $R^{6b}$, $R^{7a}$, and $R^{7b}$, in formula (Z-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Z-3) is linked to the —(C=O)—O— linkage in recurring unit (7) via any one of $R^{8a}$, $R^{8b}$, $R^{9a}$, and $R^{9b}$, $R^{11}$ is hydrogen or a straight, branched or cyclic $C_1$-$C_{18}$ alkyl group in which at least one hydrogen atom may be substituted by a halogen atom or at least one methylene moiety may be substituted by an oxygen atom or carbonyl group, $R^{12}$ is a straight, branched or cyclic $C_1$-$C_{19}$ alkyl group in which at least one hydrogen atom may be substituted by a halogen atom or at least one methylene moiety may be substituted by an oxygen atom or carbonyl group, or $R^{11}$ and $R^{12}$ may bond together to form a cyclic structure with the carbon and oxygen atoms to which they are attached, with the proviso that when the structure (Z-1), (Z-2) or (Z-3) is linked to the —(C=O)—O— linkage in recurring unit (7) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

[29] A resist composition comprising (A) a polymer, (B) a base polymer having a structure derived from lactone ring, hydroxyl group and/or maleic anhydride, said base polymer becoming soluble in alkaline developer under the action of acid, (C) a compound capable of generating an acid upon exposure to high-energy radiation, and (D) an organic solvent, said polymer (A) comprises recurring units as set forth in [26], [27] or [28], and further recurring units of one or more type selected from the general formulae (8a) to (8f):

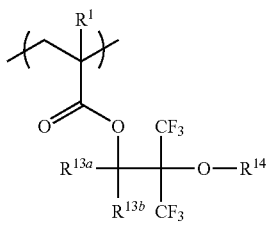

(8a)

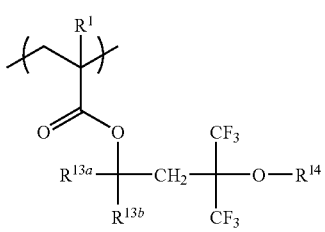

(8b)

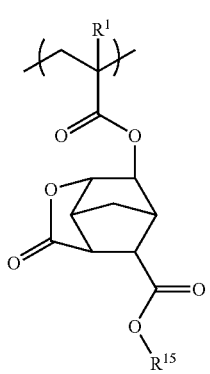

(8c)

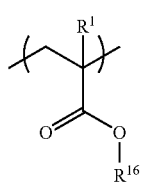

(8d)

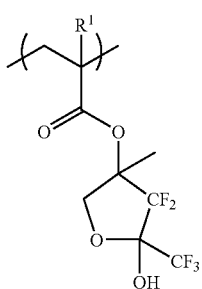

(8e)

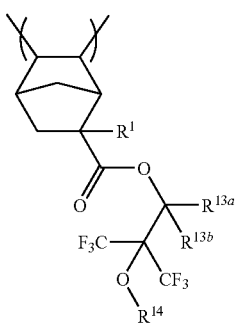

(8f)

wherein $R^1$ is hydrogen, methyl or trifluoromethyl, $R^{13a}$ and $R^{13b}$ each are hydrogen or a straight, branched or cyclic $C_1$-$C_{15}$ alkyl group, or $R^{13a}$ and $R^{13b}$ may bond together to form a ring with the carbon atom to which they are attached, $R^{14}$ is hydrogen, a straight, branched or cyclic $C_1$-$C_{15}$ alkyl or fluoroalkyl group, or an acid labile group, $R^{15}$ is a straight, branched or cyclic $C_1$-$C_{15}$ fluoroalkyl group, and $R^{16}$ is an acid labile group.

[30] The resist composition of any one of [26] to [29], further comprising (E) a basic compound.

[31] The resist composition of any one of [26] to [30], further comprising (F) a dissolution regulator.

[32] A pattern forming process comprising the steps of (1) applying the resist composition of any one of [26] to [31] onto a substrate to form a resist film, (2) heat treating the resist film and exposing it to high-energy radiation through a photomask, and (3) developing the exposed resist film with a developer.

[33] A pattern forming process comprising the steps of (1) applying the resist composition of any one of [26] to [31] onto a substrate to form a resist film, (2) heat treating the coated substrate, and exposing it to high-energy radiation through a photomask while keeping a liquid between a projection lens and the coated substrate, and (3) developing the exposed resist film with a developer.

[34] A pattern forming process comprising the steps of (1) applying the resist composition of any one of [26] to [31] onto a substrate to form a resist film, (2) forming a protective coating on the resist film, (3) heat treating the coated substrate, and exposing it to high-energy radiation through a photomask while keeping a liquid between a projection lens and the coated substrate, and (4) developing the exposed resist film with a developer.

[35] The process of [33] or [34], wherein the liquid is water.

[36] The process of any one of [32] to [35], wherein an exposure light source emits high-energy radiation having a wavelength of 180 to 250 nm.

[37] A pattern forming process comprising the steps of (1) applying the resist composition of any one of [26] to [31] onto a mask blank substrate to form a coating, (2) heat treating the coating and irradiating it in vacuum with an electron beam, and (3) developing the coating with a developer.

ADVANTAGEOUS EFFECTS OF INVENTION

The fluorinated monomer of cyclic acetal structure is useful as a raw material for the production of opto-functional materials and coating materials and can be prepared from reactants which are readily available and easy to handle. The polymer derived therefrom has high transparency to radiation of wavelength 200 nm or shorter and improved water repellency, is designed such that any of its properties including water repellency, lipophilicity, acid lability and hydrolyzability may be tailored by a choice of a proper structure, and finds use as the materials adapted for ArF laser exposure immersion lithography such as photoresist additives and protective coating materials.

The resist protective coating composition comprising the polymer of cyclic acetal structure forms a film which has a high receding contact angle sufficient to prevent leach-out of resist components and penetration of water, and allows for formation of a resist pattern of satisfactory profile without defects after development when processed by immersion lithography.

The resist composition comprising the polymer as an additive allows for formation of a resist pattern of satisfactory profile after development when processed by immersion lithography.

DESCRIPTION OF EMBODIMENTS

The singular forms "a", "an" and "the" include plural referents unless the context clearly dictates otherwise. The notation (Cn-Cm) means a group containing from n to m carbon atoms per group.

The abbreviation Me is methyl, and Ac is acetyl.

Fluorinated Monomer

One embodiment of the invention is a fluorinated monomer of cyclic acetal structure represented by the general formula (1):

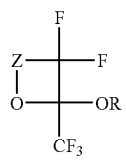
(1)

wherein R is a straight, branched or cyclic $C_1$-$C_{20}$ alkyl group in which at least one hydrogen atom may be substituted by a halogen atom or at least one methylene moiety may be substituted by an oxygen atom or carbonyl group, and Z is a divalent organic group which is attached at opposite ends to the alkylenoxy group to form a 5- or 6-membered ring and which contains a polymerizable unsaturated group.

In general, the acetal is known labile to acid. It is thus believed that the cyclic acetal structure in the fluorinated monomer is decomposable under the action of an acid generated by an acid generator, for example. In this case, the cyclic acetal is decomposed to form a hydrophilic hemiacetal structure, whereby the contact angle of polymer surface is reduced.

It is preferred for ease of preparation that the fluorinated monomer have a structure represented by the general formula (2), (3) or (4).

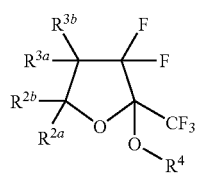
(2)

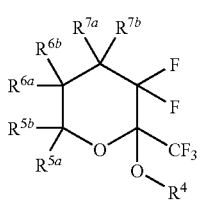
(3)

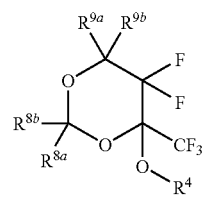
(4)

Herein $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, and at least one of $R^{2a}$, $R^{2b}$, $R^{3a}$, and $R^{3b}$ is a monovalent organic group containing a polymerizable unsaturated group. Any two of $R^{2a}$, $R^{2b}$, $R^{3a}$, and $R^{3b}$ may bond together to form a ring with the carbon atom to which they are attached, with the proviso that the ring contains a polymerizable unsaturated group when the remaining groups of $R^{2a}$, $R^{2b}$, $R^{3a}$, and $R^{3b}$ which do not participate in the ring formation do not contain a polymerizable unsaturated group. $R^4$ is a straight, branched or cyclic $C_1$-$C_{20}$ alkyl group in which at least one hydrogen atom may be substituted by a halogen atom or at least one methylene moiety may be substituted by an oxygen atom or carbonyl group. $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, and at least one of $R^{5a}$, $R^{5b}$, $R^{6a}$, $R^{6b}$, $R^{7a}$, and $R^{7b}$ is a monovalent organic group containing a polymerizable unsaturated group. Any two of $R^{5a}$, $R^{5b}$, $R^{6a}$, $R^{6b}$, $R^{7a}$, and $R^{7b}$ may bond together to form a ring with the carbon atom to which they are attached, with the proviso that the ring contains a polymerizable unsaturated group when the remaining groups of $R^{5a}$, $R^{5b}$, $R^{6a}$, $R^{6b}$, $R^{7a}$, and $R^{7b}$ which do not participate in the ring formation do not contain a polymerizable unsaturated group. $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, and at least one of $R^{8a}$, $R^{8b}$, $R^{9a}$, and $R^{9b}$ is a monovalent organic group containing a polymerizable unsaturated group. Any two of $R^{8a}$, $R^{8b}$, $R^{9a}$, and $R^{9b}$ may bond together to form a ring with the carbon atom to which they are attached, with the proviso that the ring contains a polymerizable unsaturated group when the remaining groups of $R^{8a}$, $R^{8b}$, $R^{9a}$, and $R^{9b}$ which do not participate in the ring formation do not contain a polymerizable unsaturated group.

In the foregoing formulae, the structure of the groups represented by Z, R, $R^{2a}$, $R^{2b}$, $R^{3a}$, $R^{3b}$, $R^4$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$ and the substitution position of a polymerizable unsaturated group thereon may be determined as appropriate depending on various conditions such as ease of preparation and polymerization ability of the monomer, and physical properties of a polymer synthesized therefrom.

Z is a divalent organic group containing a polymerizable unsaturated group. Typical are straight, branched or cyclic divalent $C_1$-$C_{15}$ organic groups containing a polymerizable unsaturated group. Suitable divalent organic groups are obtained from monovalent hydrocarbon groups by substituting a single bond for one hydrogen atom, and further substituting a polymerizable unsaturated group for another hydrogen atom, while suitable monovalent hydrocarbon groups include straight, branched or cyclic alkyl groups such as methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7,10}$]dodecylbutyl, tetracyclo[4.4.0.1$^{2,5}$.1$^{7,10}$]dodecylmethyl, ethyltetracyclo[4.4.0.1$^{2,5}$.1$^{7,10}$]dodecylmethyl, and ethyltetracyclo[4.4.0.1$^{2,5}$.1$^{7,10}$]dodecylethyl; aryl groups such as phenyl, tolyl, naphthyl, anthryl, and phenanthryl; and aralkyl groups such as benzyl, diphenylmethyl, and phenethyl. In the foregoing groups, one or more hydrogen atoms may be substituted by halogen, alkyl, aryl, alkoxy, alkoxycarbonyl or oxo groups.

R and $R^4$ each are a straight, branched or cyclic $C_1$-$C_{20}$ alkyl group in which at least one hydrogen atom may be substituted by a halogen atom or at least one methylene moiety may be substituted by an oxygen atom or carbonyl group. While those groups of the formula —CO—$R^{10}$ or —CH($R^{11}$)—O$R^{12}$ to be described later are desired, other suitable alkyl groups include methyl, ethyl, propyl, isopropyl, n-butyl, sec-butyl, tert-butyl, tert-amyl, n-pentyl, n-hexyl, n-heptyl, n-octyl, n-nonyl, n-decyl, eicosanyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, trifluoromethyl, 2,2,2-trifluoroethyl, 2,2,3,3,3-pentafluoropropyl, 2-methoxyethyl, 2-(hexafluoroisopropoxy)ethyl, 2-acetoxyethyl, and acetonyl. By selecting an optimum structure as R or $R^4$, properties such as water repellency and lipophilicity may be tailored as required.

$R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group. At least one of $R^{2a}$, $R^{2b}$, $R^{3a}$, and $R^{3b}$ is a monovalent organic group containing a polymerizable unsaturated group. The straight, branched or cyclic monovalent $C_1$-$C_{15}$ organic group include monovalent hydrocarbon groups, for example, straight, branched or cyclic alkyl groups such as methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7,10}$]dodecylbutyl, tetracyclo[4.4.0.1$^{2,5}$.1$^{7,10}$]dodecylmethyl, ethyltetracyclo[4.4.0.1$^{2,5}$.1$^{7,10}$]dodecylmethyl, and ethyltetracyclo[4.4.0.1$^{2,5}$.1$^{7,10}$]dodecylethyl, aryl groups such as phenyl, methylphenyl, naphthyl, anthryl, and phenanthryl, and aralkyl groups such as benzyl, diphenylmethyl and phenethyl; alkoxy groups such as methoxy, ethoxy and propoxy, and acyloxy groups such as formyloxy and acetoxy. In the foregoing groups, one or more hydrogen atoms may be substituted by halogen, alkyl, aryl, alkoxy, alkoxycarbonyl, oxo, alkoxyalkyl, acyloxy, acyloxyalkyl, alkoxyalkoxy or other groups. Inter alia, hydrogen, hydroxyl, halogen, methyl, ethyl, propyl, tert-butyl, and perfluoroalkyl groups are preferred. The monovalent organic group containing a polymerizable unsaturated group may be a polymerizable unsaturated group itself or a monovalent organic group as listed above in which one hydrogen atom is substituted by a polymerizable unsaturated group.

A combination of any two of $R^{2a}$, $R^{2b}$, $R^{3a}$, and $R^{3b}$ may bond together to form a ring with the carbon atom to which they are attached. Typical ring-forming pairs include a pair of $R^{2a}$ and $R^{2b}$, $R^{2a}$ and $R^{3a}$, $R^{2a}$ and $R^{3b}$, $R^{2b}$ and $R^{3a}$, $R^{2b}$ and $R^{3b}$, and $R^{3a}$ and $R^{3b}$. Exemplary rings thus formed include $C_3$-$C_{12}$ alicyclic hydrocarbons such as cyclopropane, cyclobutane, cyclopentane, cyclohexane, bicyclo[2.2.1]heptane, bicyclo[2.2.2]octane, tricyclo[5.2.1.0$^{2,6}$]decane, adamantane, and tetracyclo[4.4.0.1$^{2,5}$.1$^{7,10}$]dodecane as well as fused rings containing any of the foregoing. In the foregoing alicyclic hydrocarbons, one or more hydrogen atoms may be substituted by hydroxyl, halogen, alkyl, aryl, alkoxy, alkoxycarbonyl, oxo, alkoxyalkyl, acyloxy, acyloxyalkyl, alkoxyalkoxy or other groups.

It is noted that the ring contains a polymerizable unsaturated group when the remaining groups of $R^{2a}$, $R^{2b}$, $R^{3a}$, and $R^{3b}$ which do not participate in the ring formation (for example, $R^{3a}$ and $R^{3b}$ when $R^{2a}$ and $R^{2b}$ form a ring, or $R^{2b}$ and $R^{3b}$ when $R^{2a}$ and $R^{3a}$ form a ring) do not contain a polymerizable unsaturated group.

$R^{5a}$, $R^{5b}$, $R^{6a}$, $R^{6b}$, $R^{7a}$, and $R^{7b}$ are as exemplified for $R^{2a}$, $R^{2b}$, $R^{3a}$, and $R^{3b}$. Typical ring-forming pairs include a pair of $R^{5a}$ and $R^{5b}$, $R^{5a}$ and $R^{6a}$, $R^{5a}$ and $R^{6b}$, $R^{5b}$ and $R^{6a}$, $R^{5b}$ and $R^{6b}$, $R^{6a}$ and $R^{6b}$, $R^{6a}$ and $R^{7a}$, $R^{6a}$ and $R^{7b}$, $R^{6b}$ and $R^{7a}$, $R^{6b}$ and $R^{7b}$, and $R^{7a}$ and $R^{7b}$. The same applies to $R^{8a}$, $R^{8b}$, $R^{9a}$, and $R^{9b}$, and typical ring-forming pairs include a pair of $R^{8a}$ and $R^{8b}$, and $R^{9a}$ and $R^{9b}$.

The fluorinated monomer of the invention may be endowed with alkaline hydrolyzability depending on the desired performance. In such a case, the fluorinated monomer preferably has a structure of the general formula (2-1), (3-1) or (4-1). Hemiacetal hydroxyl group has a higher acidity than alcoholic hydroxyl group. Since the ester bond in formula (2-1), (3-1) or (4-1) is an ester between a carboxylic acid and a hemiacetal hydroxyl group having a further higher acidity as a result of five fluorine atoms bonding to vicinal carbon atoms, and thus regarded as mixed acid anhydride, this ester is highly susceptible to alkaline hydrolysis as compared with esters of carboxylic acid with ordinary alcohol. It is thus believed that this ester is readily hydrolyzed with an alkaline developer, for example. When the ester bond in formula (2-1), (3-1) or (4-1) is hydrolyzed, a highly hydrophilic hemiacetal structure forms whereby the contact angle at polymer surface is reduced.

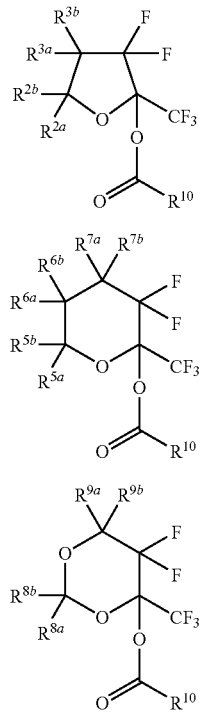

(2-1)

(3-1)

(4-1)

Herein $R^{2a}$ through $R^{9b}$ are as defined and exemplified above, and $R^{10}$ is a straight, branched or cyclic $C_1$-$C_{19}$ alkyl group in which at least one hydrogen atom may be substituted by a halogen atom or at least one methylene moiety may be substituted by an oxygen atom or carbonyl group.

$R^{10}$ is a straight, branched or cyclic $C_1$-$C_{19}$ alkyl group in which at least one hydrogen atom may be substituted by a halogen atom or at least one methylene moiety may be substituted by an oxygen atom or carbonyl group. Suitable alkyl groups include methyl, ethyl, propyl, isopropyl, n-butyl, sec-butyl, tert-butyl, isobutyl, tert-amyl, n-pentyl, neopentyl, n-hexyl, n-heptyl, n-octyl, n-nonyl, n-decyl, nonadecyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, trifluoromethyl, 2,2,2-trifluoroethyl, 2,2,3,3,3-pentafluoropropyl, 1-methyl-2,2,2-trifluoroethyl, 2-methoxyethyl, 2-(hexafluoroisopropoxy)ethyl, 2-acetoxyethyl, and acetonyl. By selecting an optimum structure as $R^{10}$, properties such as alkaline hydrolysis, water repellency and lipophilicity may be tailored as required.

Also the fluorinated monomer of the invention may be endowed with higher acid lability depending on the desired performance. In such a case, the fluorinated monomer preferably has a structure of the general formula (2-2), (3-2) or (4-2). It is believed that the acid labile acetal structure (—O—CH($R^{11}$)—O$R^{12}$) included in formula (2-2), (3-2) or (4-2) will be readily decomposed if an acid generated by an acid generator is present in proximity thereto. When the acetal structure (—O—CH($R^{11}$)—O$R^{12}$) in formula (2-2), (3-2) or (4-2) is decomposed, a highly hydrophilic hemiacetal structure forms whereby the contact angle at polymer surface is reduced.

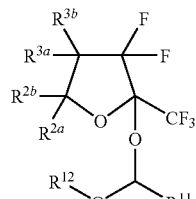

(2-2)

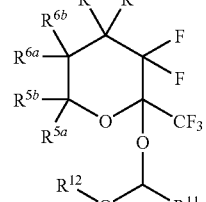

(3-2)

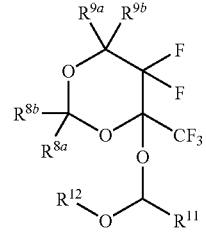

(4-2)

Herein $R^{2a}$ through $R^{9b}$ are as defined and exemplified above, $R^{11}$ is hydrogen or a straight, branched or cyclic $C_1$-$C_{18}$ alkyl group in which at least one hydrogen atom may be substituted by a halogen atom or at least one methylene moiety may be substituted by an oxygen atom or carbonyl group. $R^{12}$ is a straight, branched or cyclic $C_1$-$C_{19}$ alkyl group in which at least one hydrogen atom may be substituted by a halogen atom or at least one methylene moiety may be substituted by an oxygen atom or carbonyl group. $R^{11}$ and $R^{12}$ may bond together to form a cyclic structure with the carbon and oxygen atoms to which they are attached.

$R^{11}$ is hydrogen or a straight, branched or cyclic $C_1$-$C_{18}$ alkyl group in which at least one hydrogen atom may be substituted by a halogen atom or at least one methylene moiety may be substituted by an oxygen atom or carbonyl group. Suitable groups of $R^{11}$ include hydrogen, methyl, ethyl, propyl, isopropyl, n-butyl, sec-butyl, tert-butyl, isobutyl, tert-amyl, n-pentyl, 2-pentyl, 3-pentyl, neopentyl, n-hexyl, 2-hexyl, 3-hexyl, n-heptyl, n-octyl, n-nonyl, n-decyl, octadecyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, trifluoromethyl, 2,2,2-trifluoroethyl, 2,2,3,3,3-pentafluoropropyl, 1-methyl-2,2,2-trifluoroethyl, 2-methoxyethyl, 2-(hexafluoroisopropoxy)ethyl, 2-acetoxyethyl, and acetonyl.

$R^{12}$ is a straight, branched or cyclic $C_1$-$C_{19}$ alkyl group in which at least one hydrogen atom may be substituted by a halogen atom or at least one methylene moiety may be substituted by an oxygen atom or carbonyl group. Suitable alkyl groups include methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7,10}$]dodecylbutyl, tetracyclo[4.4.0.1$^{2,5}$.1$^{7,10}$]dodecylmethyl, ethyltetracyclo[4.4.0.1$^{2,5}$.1$^{7,10}$]dodecylmethyl, ethyltetracyclo[4.4.0.1$^{2,5}$.1$^{7,10}$]dodecylethyl, trifluoromethyl, 2,2,2-trifluoroethyl, 2,2,3,3,3-pentafluoropropyl, 1-methyl-2,2,2-trifluoroethyl, 2-methoxyethyl, 2-(hexafluoroisopropoxy)ethyl, 2-acetoxyethyl, 2-(1-adamantylcarbonyloxy)ethyl, and acetonyl.

R$^{11}$ and R$^{12}$ may bond together to form a cyclic structure with the carbon and oxygen atoms to which they are attached. Examples of the cyclic structure formed by R$^{11}$ and R$^{12}$ include tetrahydrofuran, methyltetrahydrofuran, methoxytetrahydrofuran, tetrahydropyran, methyltetrahydropyran, methoxytetrahydropyran, 1,4-dioxane rings. By selecting an optimum structure as R$^{11}$ and R$^{12}$, properties such as acid lability, water repellency and lipophilicity may be tailored as required.

The polymerizable unsaturated group included in formulae (1), (2), (3), (4), (2-1), (3-1), (4-1), (2-2), (3-2), and (4-2) may be any double bond-bearing group capable of polymerization by polymerization means such as radical polymerization, anionic polymerization or cationic polymerization. Suitable polymerizable unsaturated group-bearing structures include unsaturated hydrocarbon structures such as bicyclo[2.2.1]hept-2-ene, tricyclo[5.2.1.0$^{2,6}$]dec-8-ene, tetracyclo[4.4.0.1$^{2,5}$.1$^{7,10}$]dodec-3-ene, unsaturated ether structures such as vinyloxy and allyloxy, α,β-unsaturated ketone structures such as vinylketone and isopropenylketone, α,β-unsaturated ester structures such as acrylate, methacrylate, α-trifluoromethylacrylate and α-fluoroacrylate, and unsaturated hydrocarbon ester structures such as bicyclo[2.2.1]hept-5-ene-5-carboxylate and tetracyclo[4.4.0.1$^{2,5}$.1$^{7,10}$]dodec-8-ene-3-carboxylate. Of these, those groups of α,β-unsaturated ester structure having the general formula (A) below are preferred. Namely, acrylate, methacrylate and α-trifluoromethylacrylate structures are preferred.

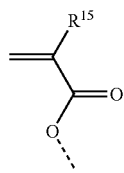

(A)

Herein R$^{15}$ is hydrogen, methyl or trifluoromethyl, and the broken line designates a valence bond.

The polymerizable unsaturated group may also be a group of unsaturated hydrocarbon structure having the general formula (B) or (C).

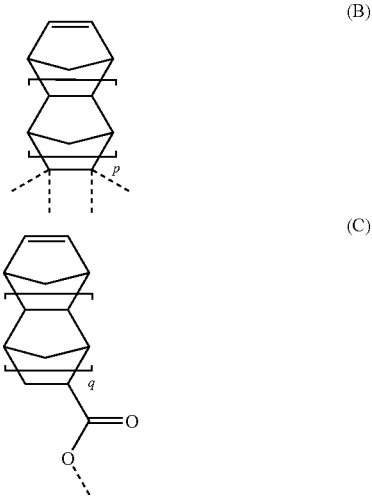

Herein p and q are each independently 1 or 0, and the broken line designates a valence bond.

It is preferred that the divalent organic group represented by Z or the polymerizable unsaturated group-containing monovalent organic group or polymerizable unsaturated group-containing ring represented by R$^{2a}$ to R$^{9b}$ contain a polymerizable unsaturated group of the above formula (A), (B) or (C). In this case, the polymerizable unsaturated group of formula (A) or (C) is incorporated in Z or polymerizable unsaturated group-containing ring in the form wherein its single valance bond binds with any one valence bond of a trivalent linking group. The trivalent linking group is preferably a straight, branched or cyclic C$_1$-C$_{10}$ alkylene group which may have substituted thereon a hydroxyl, halogen, alkoxy, alkoxyalkyl, alkoxyalkoxy, acyloxy, acyloxyalkyl or other groups, with one hydrogen atom being replaced by a single bond (or valence bond). The polymerizable unsaturated group of formula (A) or (C) is incorporated in the polymerizable unsaturated group-containing monovalent organic group represented by R$^{2a}$ to R$^{9b}$ in two different forms. In one form, the group of formula (A) or (C) as such constitutes the polymerizable unsaturated group-containing monovalent organic group, and this group binds directly with a carbon atom (designated carbon atom "C"), that is, the valence bond of formula (A) or (C) binds directly with carbon atom "C". In the other form, the group of formula (A) or (C) binds with carbon atom "C" via a divalent linking group, preferably a straight, branched or cyclic C$_1$-C$_{10}$ alkylene group, that is, the valence bond of formula (A) or (C) binds with carbon atom "C" via a divalent linking group.

As to the polymerizable unsaturated group of formula (B), preferably one or two of its valence bonds become the valence bond via which said group is incorporated in Z or the polymerizable unsaturated group-containing monovalent organic group or polymerizable unsaturated group-containing ring represented by R$^{2a}$ to R$^{9b}$, while the remaining valence bonds preferably bind with hydrogen atoms, hydroxyl groups, halogen atoms, or straight, branched or cyclic C$_1$-C$_{15}$ organic groups (as exemplified above).

The form wherein one valence bond of formula (B) is incorporated in Z or the polymerizable unsaturated group-containing monovalent organic group or polymerizable unsaturated group-containing ring represented by R$^{2a}$ to R$^{9b}$ is the same as that of the valance bond of formula (A) or (C). The form wherein two valence bonds of formula (B) are incorporated in Z or the polymerizable unsaturated group-containing ring includes the form wherein the group of formula (B) itself constitutes Z or the relevant ring, and the form wherein one or both of the two valence bonds bind with the divalent linking group to constitute Z or the relevant ring. The form wherein two valence bonds of formula (B) are incorporated in the polymerizable unsaturated group-containing monovalent organic group includes the form wherein two valence bonds bind with the divalent linking groups which bind with a carbon atom at an appropriate position to form a ring, which constitutes the polymerizable unsaturated group-containing monovalent organic group.

Notably, the form wherein two valence bonds of formula (B) bind with the structure of formula (2) is exemplified by a spiro ring represented by the formula:

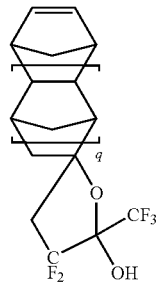

wherein p is as defined above, or a fused ring represented by the formula:

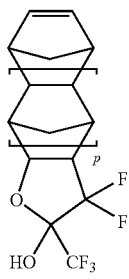

wherein p is as defined above.

Examples of the linking group are given below.

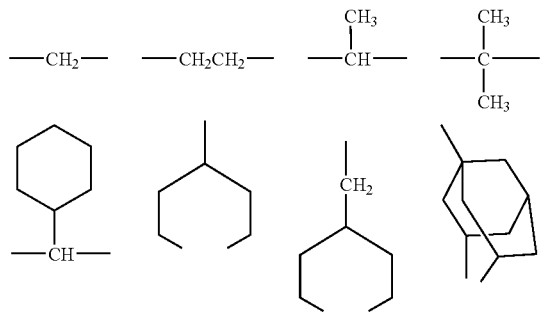

In the fluorinated monomers of cyclic acetal structure represented by formulae (1), (2), (3), (4), (2-1), (3-1), (4-1), (2-2), (3-2), and (4-2), some carbon atoms constituting the molecule may become asymmetric depending on the type and combination of groups represented by Z, R, $R^4$, $R^{2a}$ to $R^{9b}$, and $R^{10}$ to $R^{12}$, indicating that there can exist enantiomers and diastereomers. Each of formulae (1), (2), (3), (4), (2-1), (3-1), (4-1), (2-2), (3-2), and (4-2) collectively represents all such stereoisomers. Such stereoisomers may be used alone or in admixture.

Examples of the fluorinated monomers of cyclic acetal structure represented by formulae (1), (2), (3), (4), (2-1), (3-1), (4-1), (2-2), (3-2), and (4-2) are given below, bt not limited thereto.

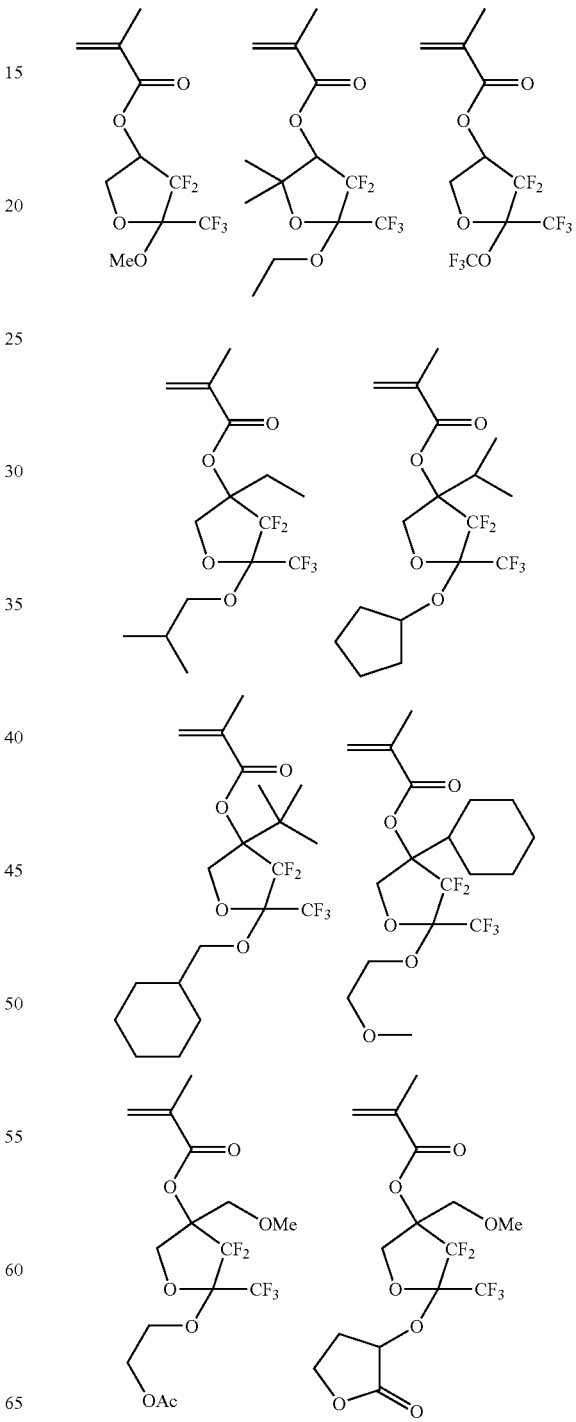

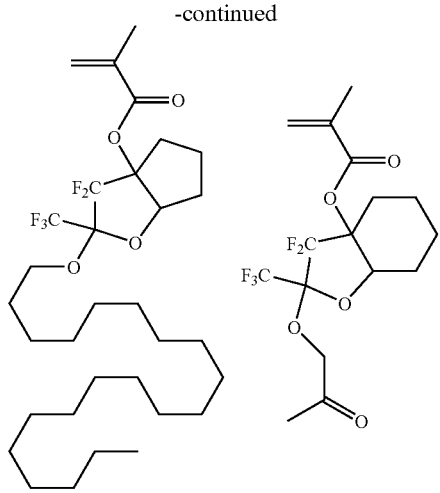
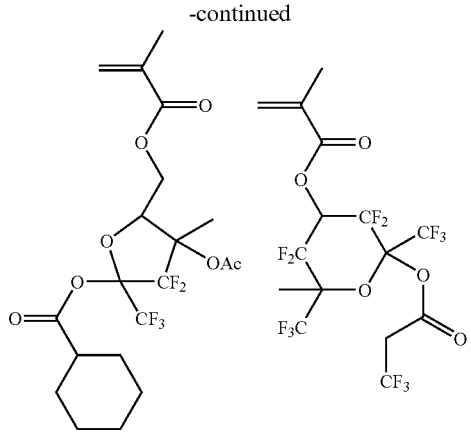
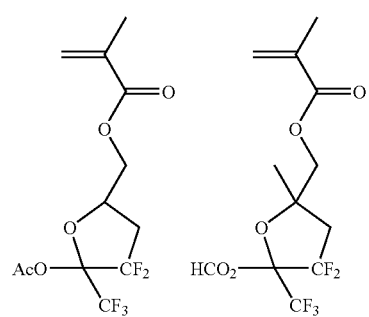
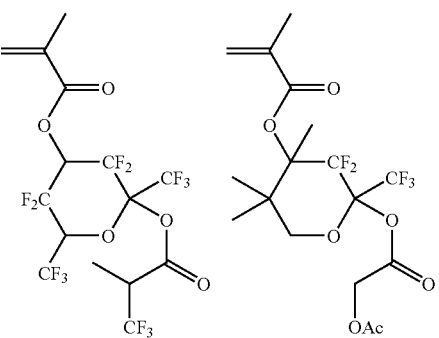
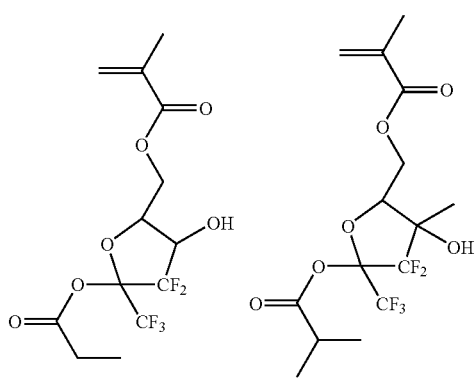
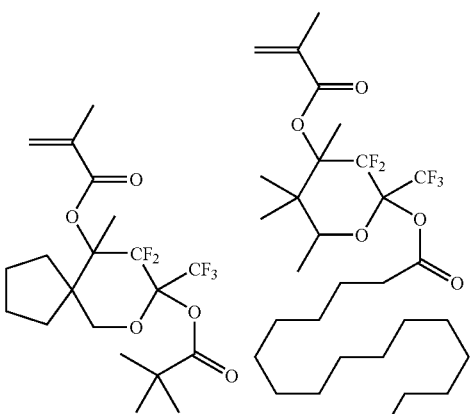
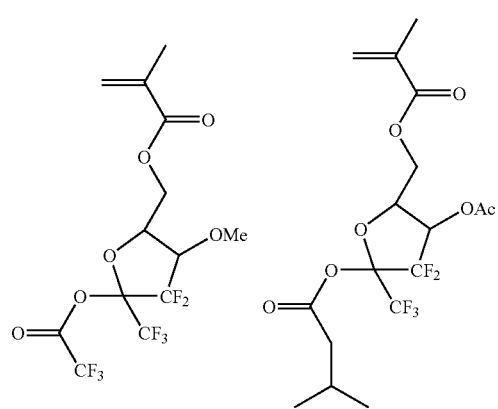
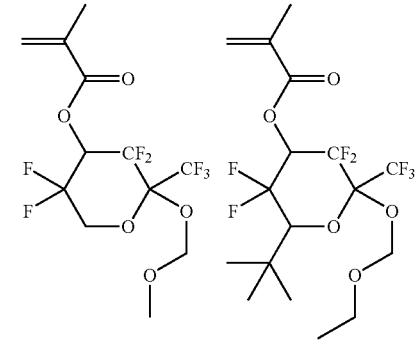

41
-continued
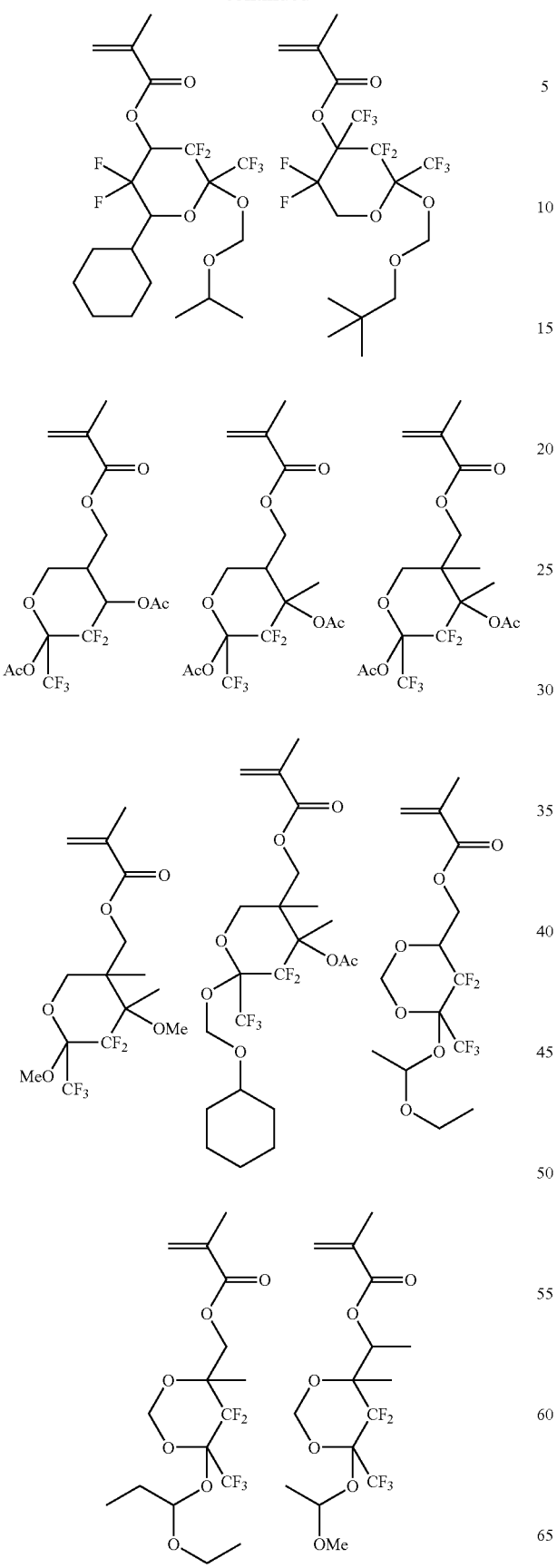
42
-continued
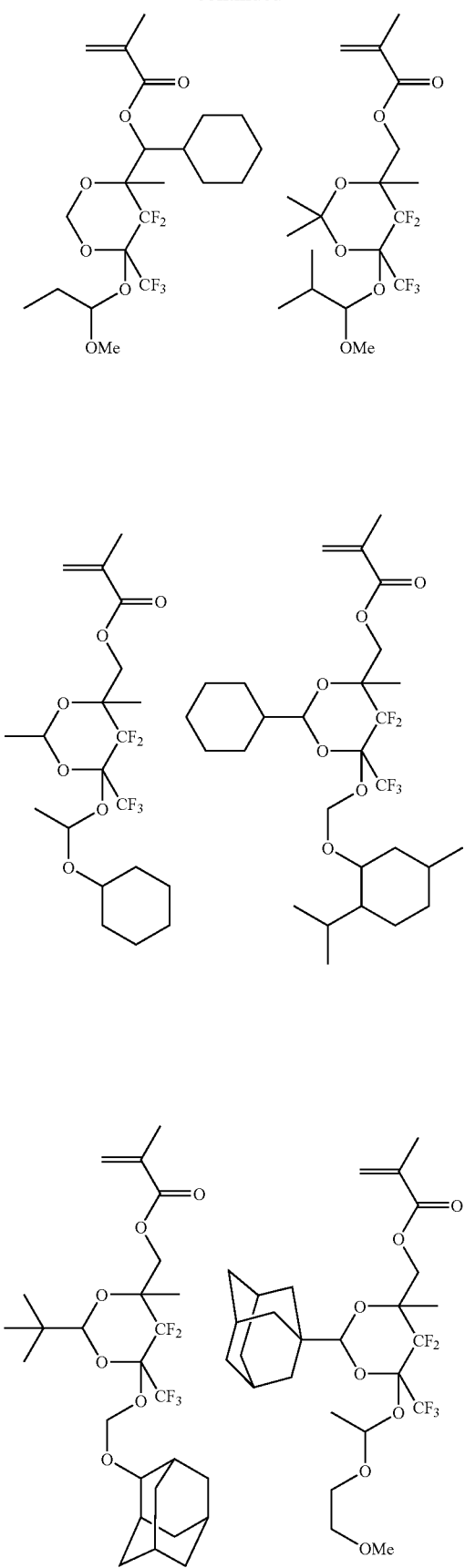

-continued
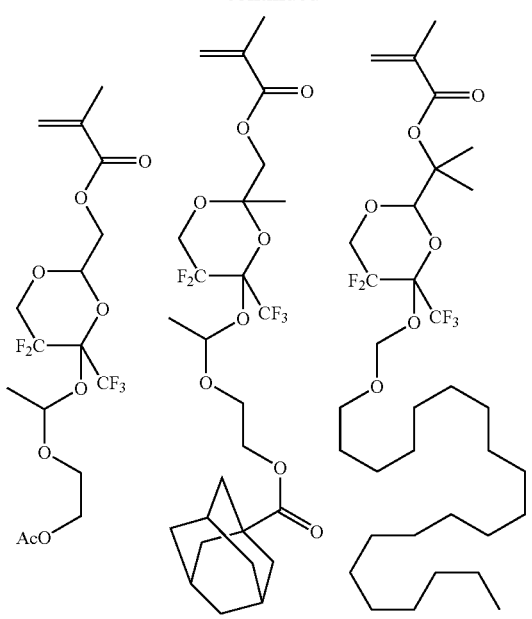
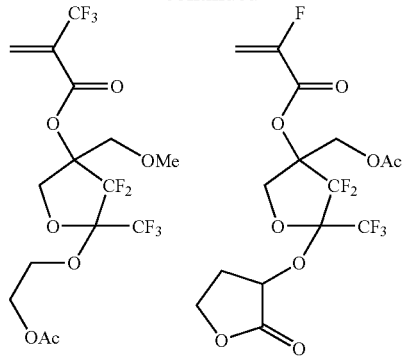
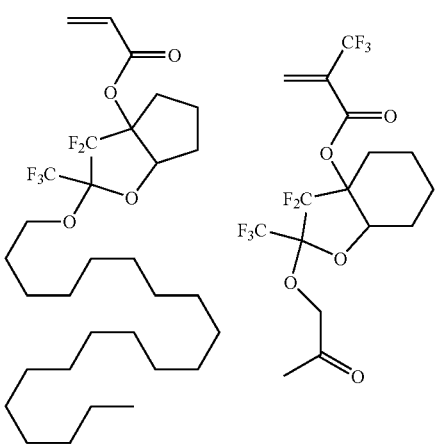
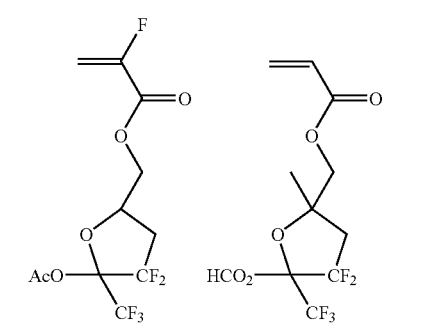
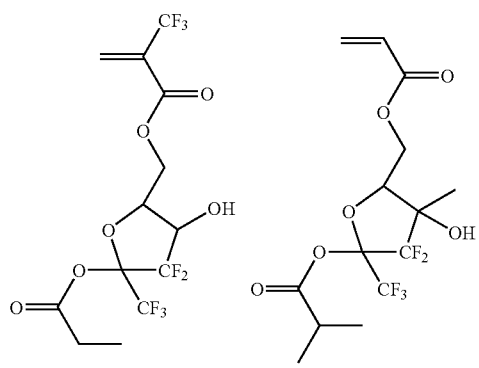

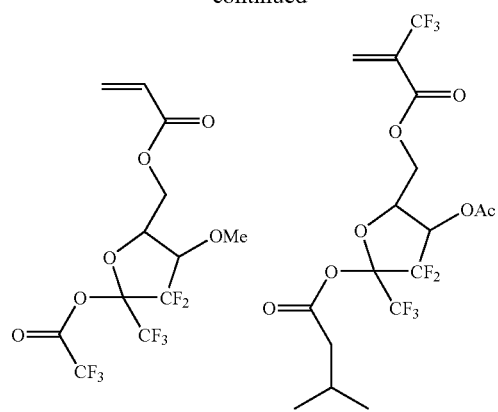
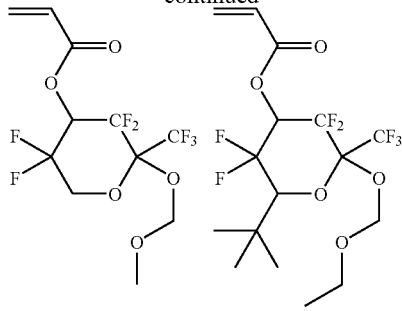
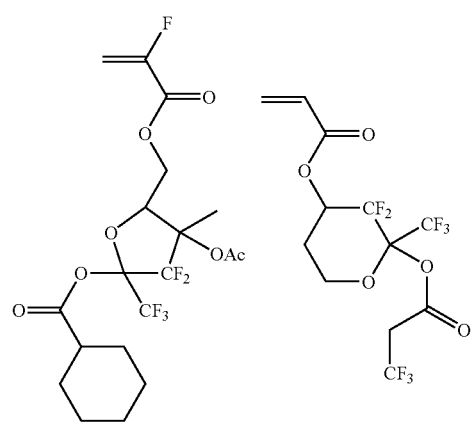
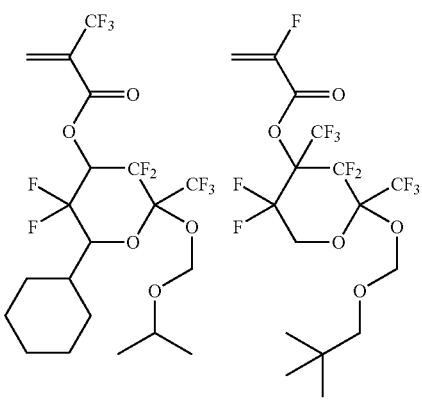
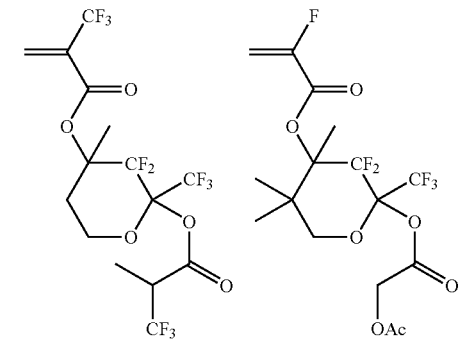
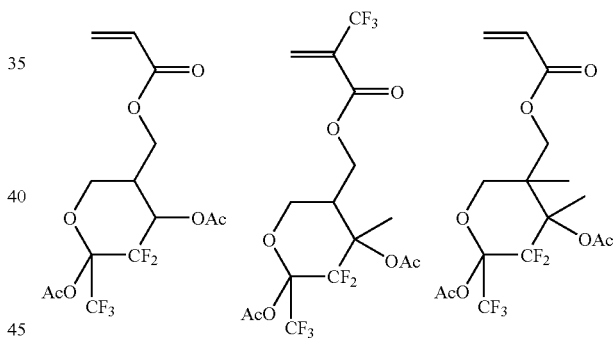
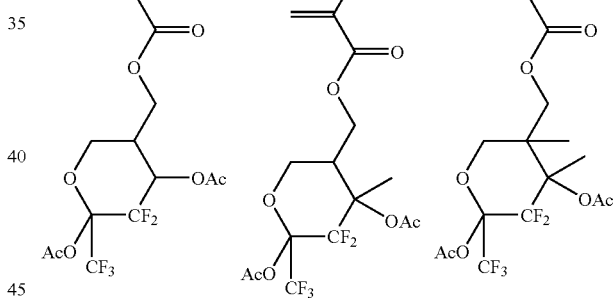
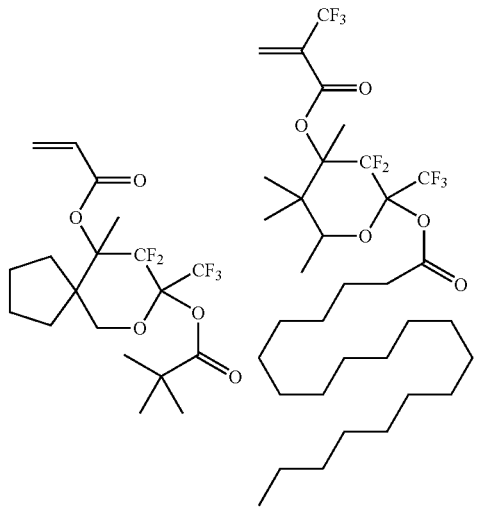
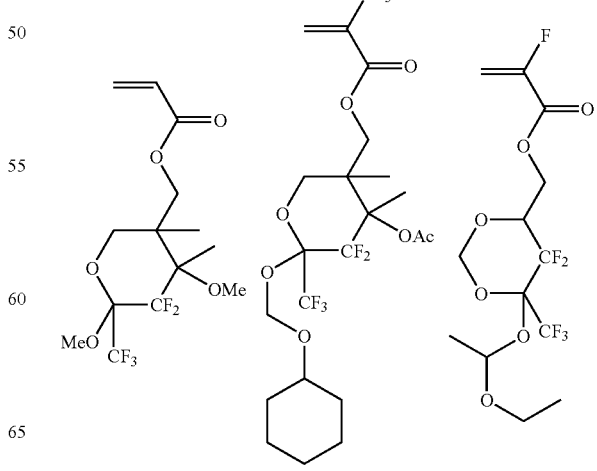

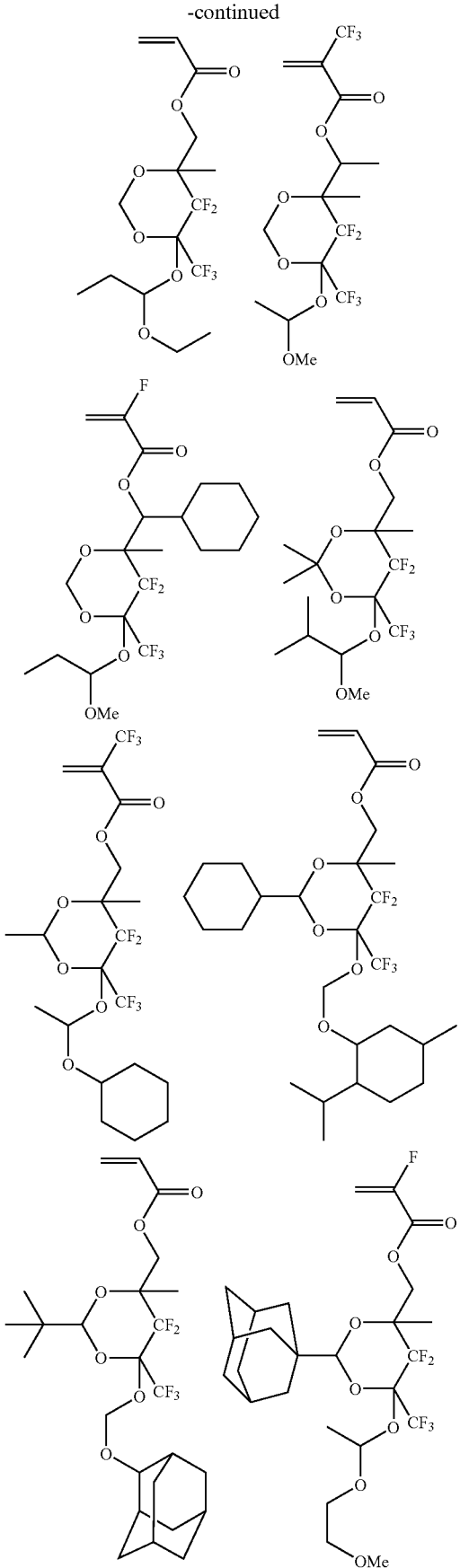
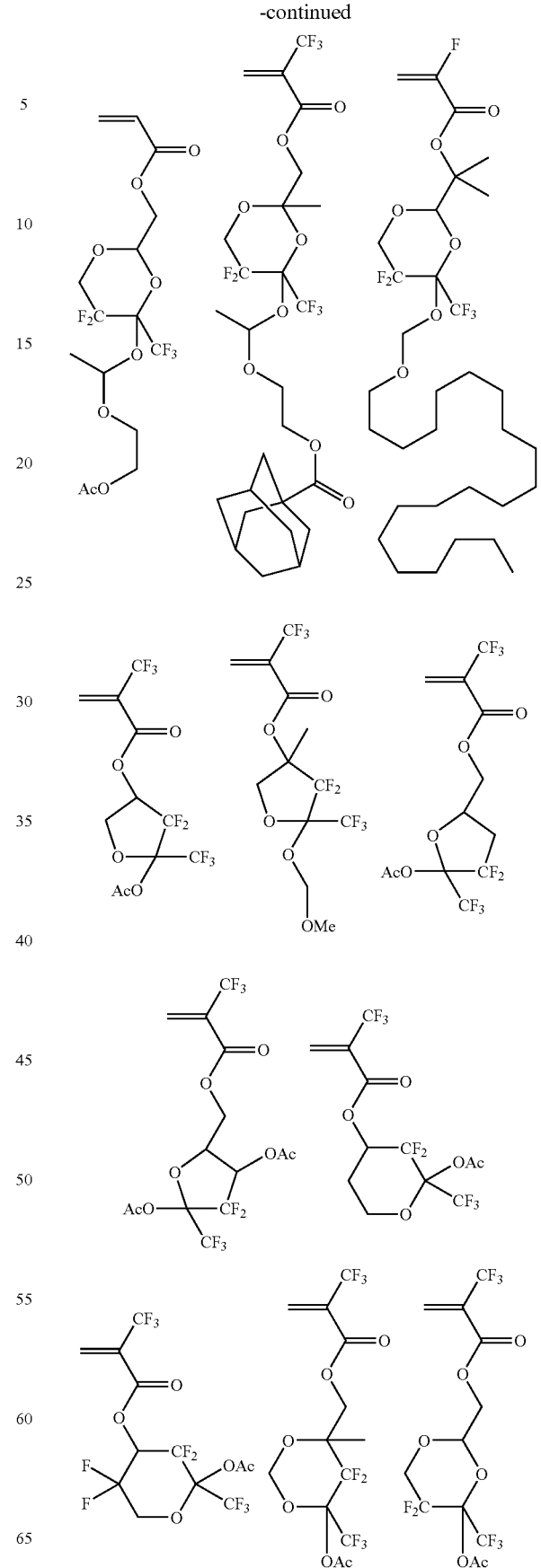

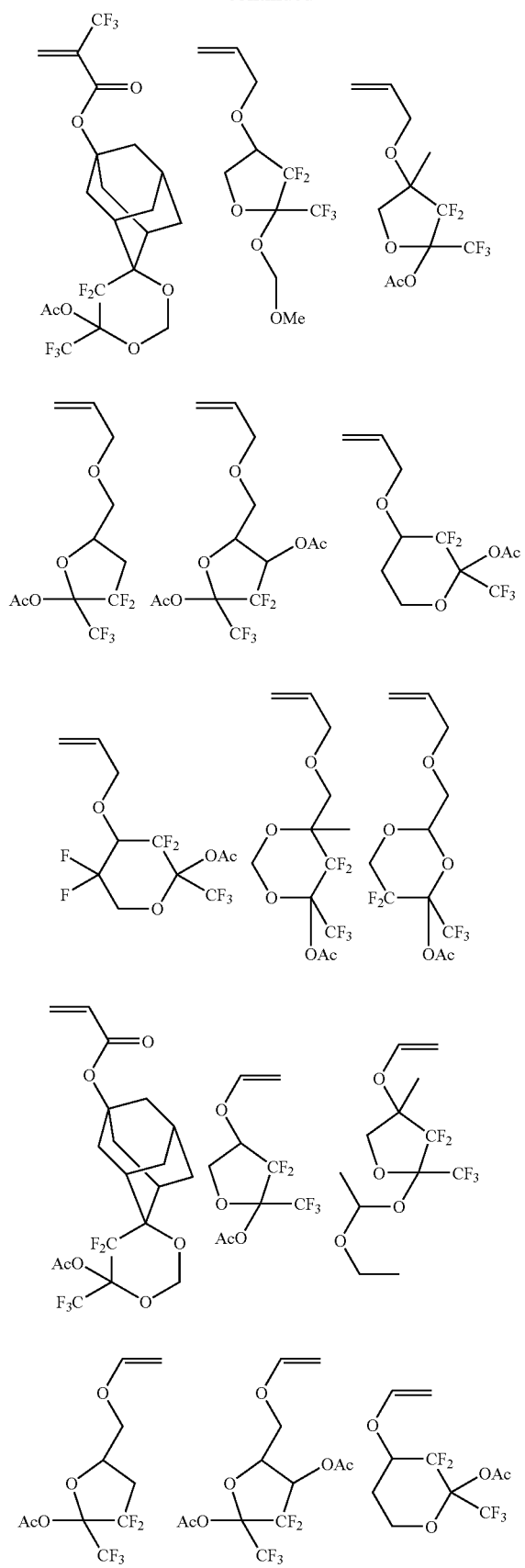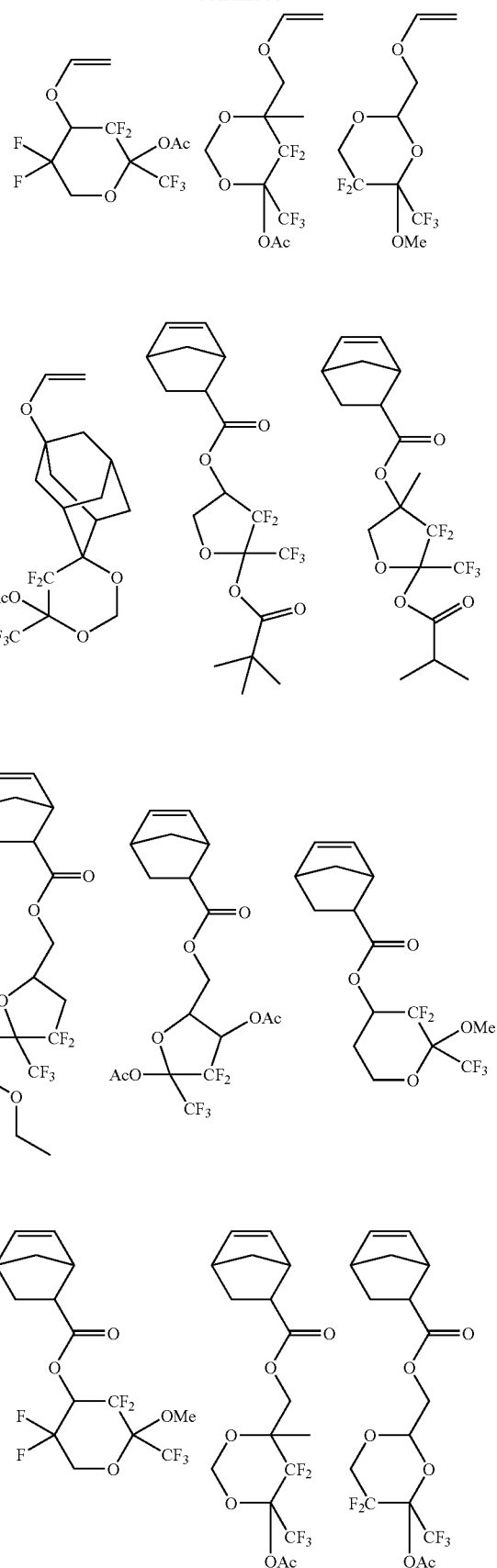

51
-continued
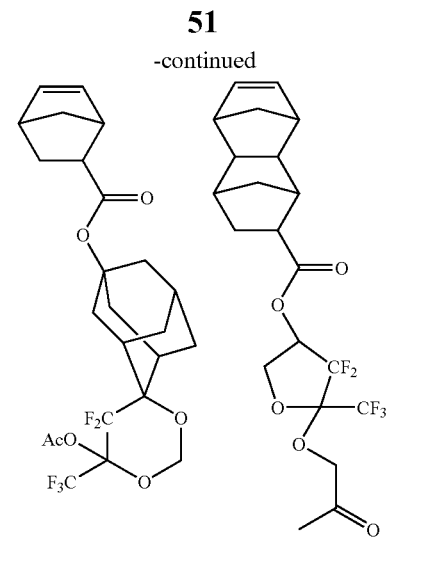
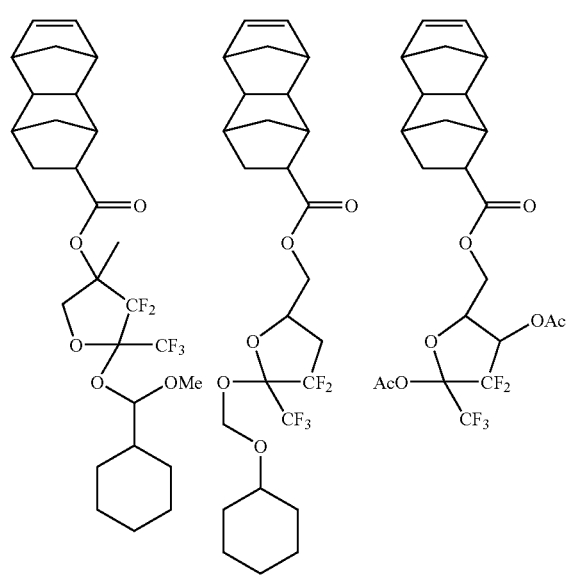
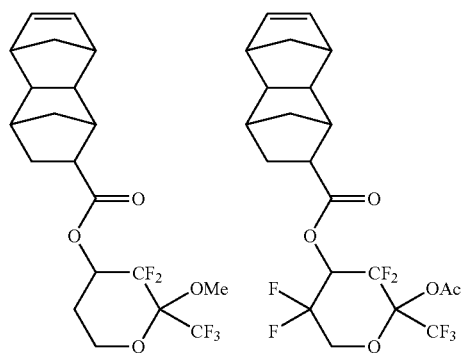
52
-continued
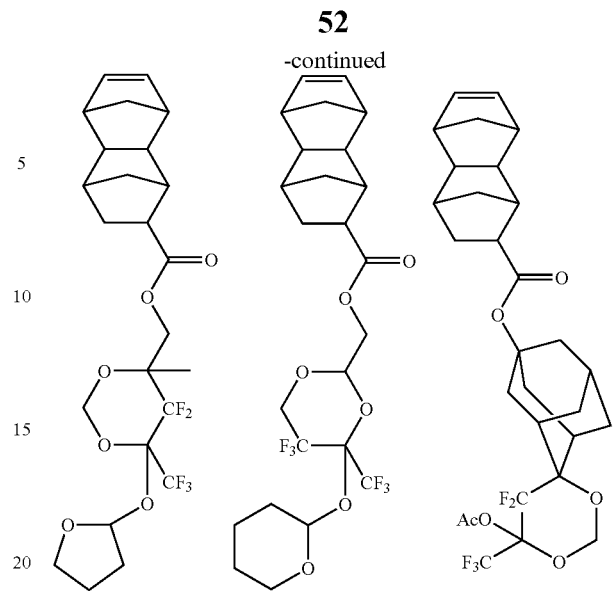
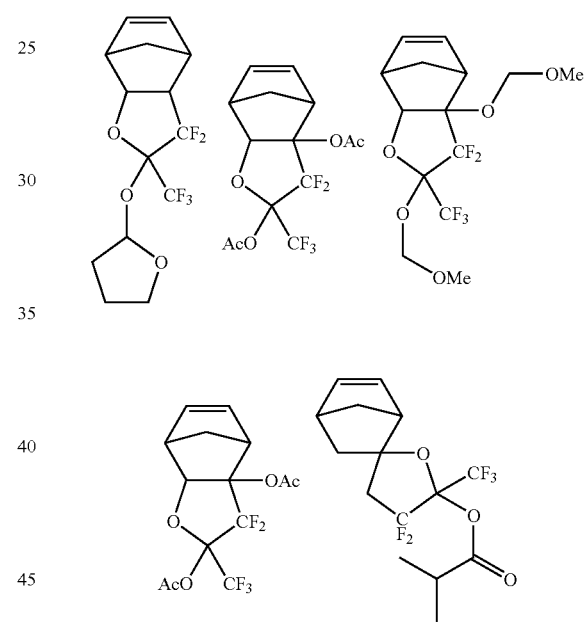
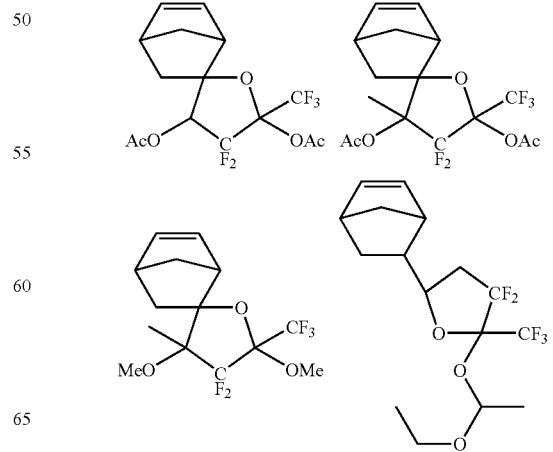

-continued
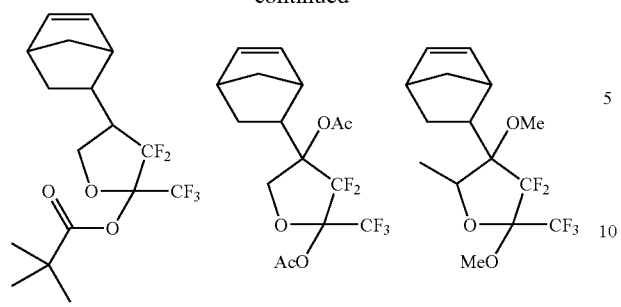
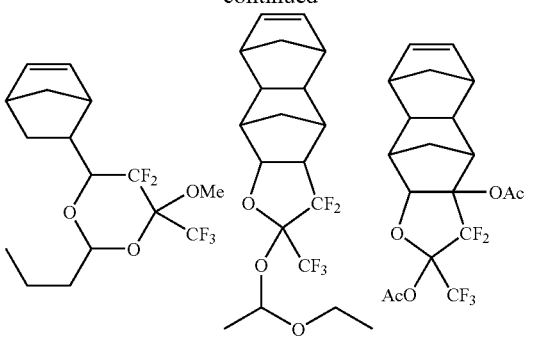
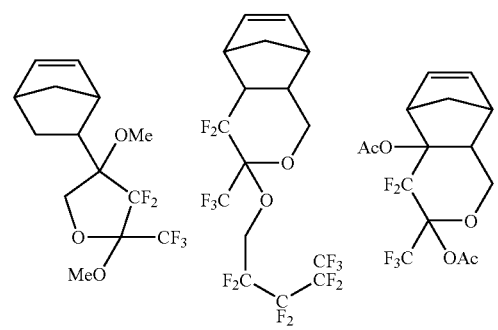
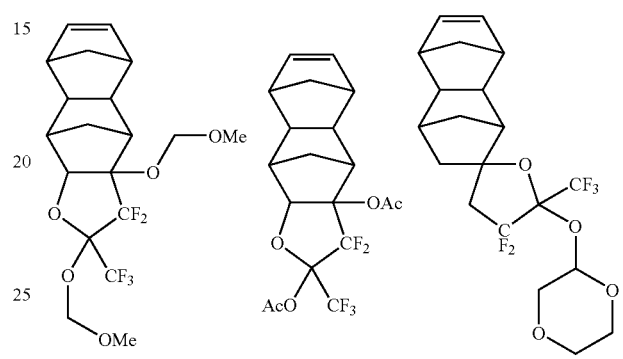
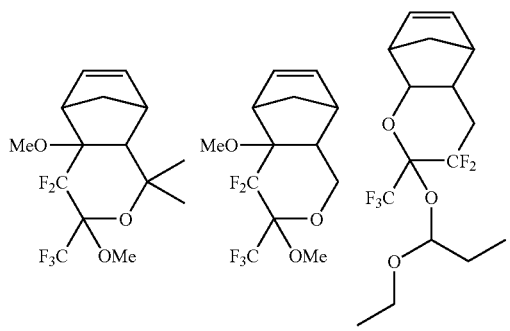
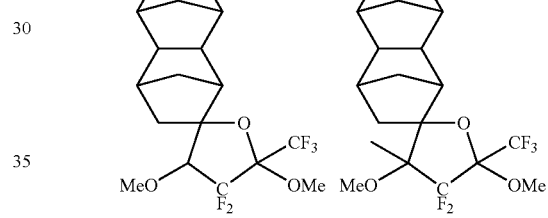
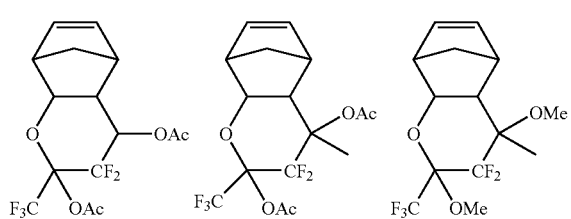
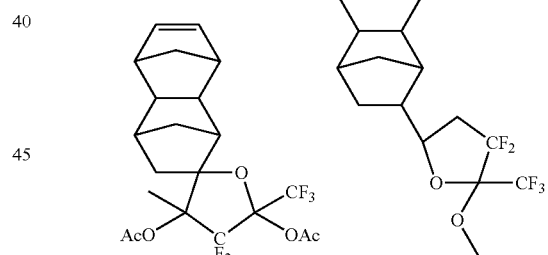
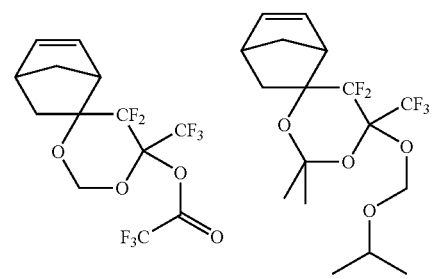
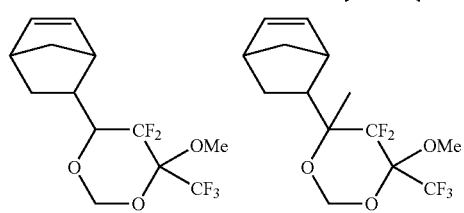
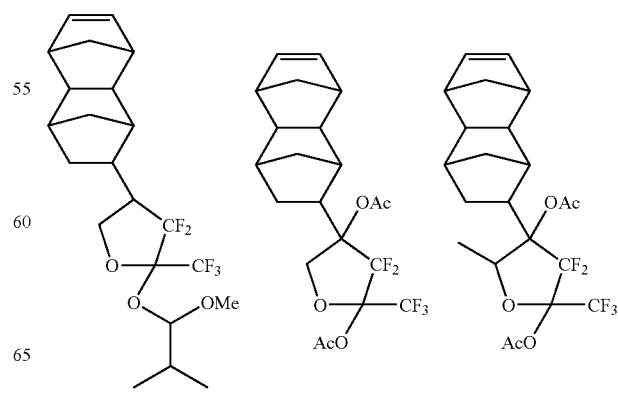

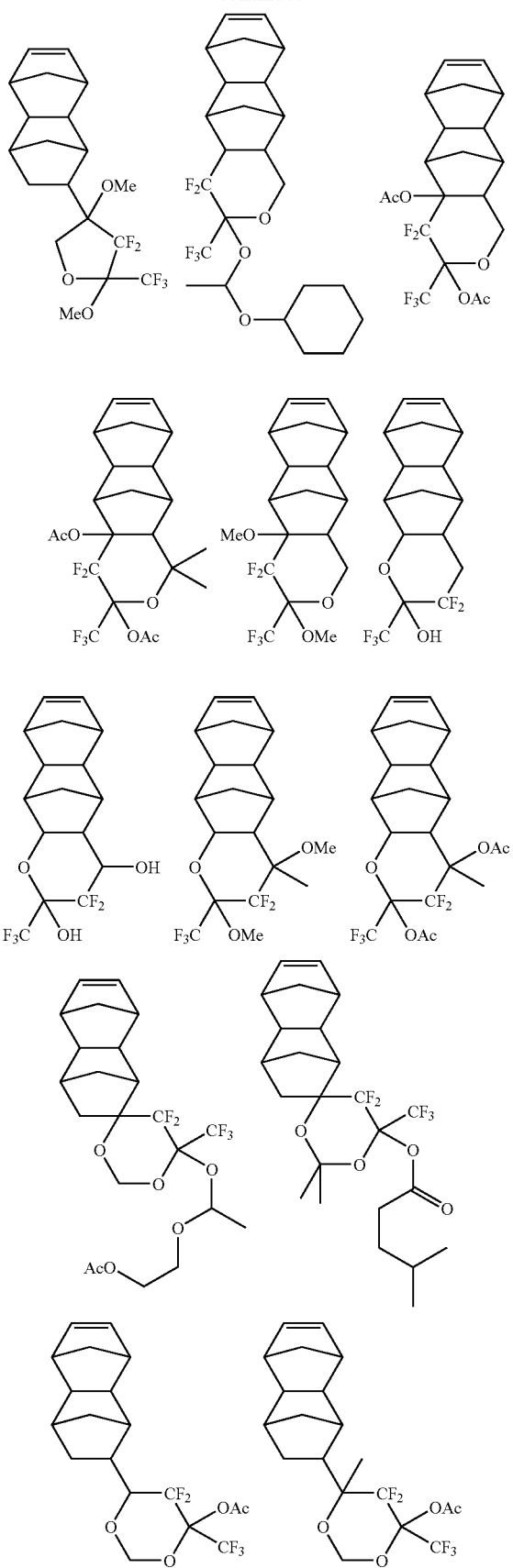

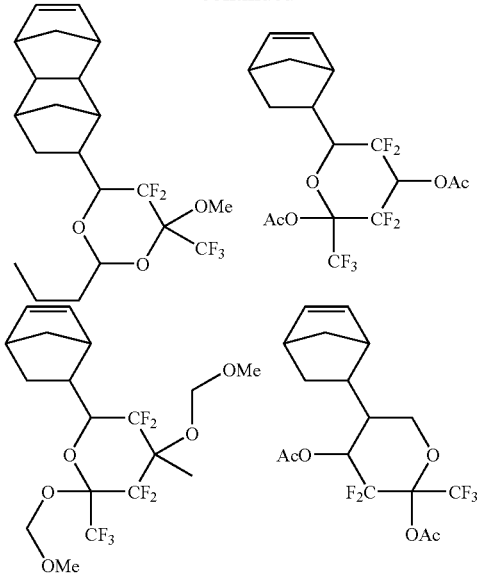

Below described is how to prepare the fluorinated monomers of the invention. The fluorinated monomers of cyclic acetal structure represented by formulae (1), (2), (3), (4), (2-1), (3-1), (4-1), (2-2), (3-2), and (4-2) are preferably prepared by an appropriate method selected in accordance with a particular structure of monomer. One exemplary method is O-alkylation or O-acylation of a corresponding hemiacetal compound although the invention is not limited thereto. The synthesis of an acetal compound (1) from a hemiacetal compound (1') according to the following scheme is described in detail as a typical example.

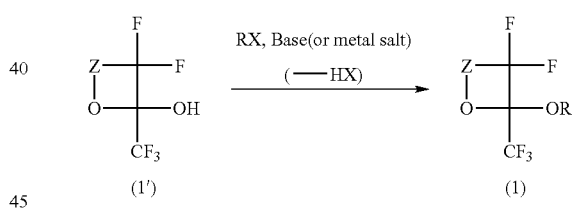

Herein Z and R are as defined above, and X is a leaving group.

The hemiacetal compound (1') used as the starting reactant may be commercially prepared by a method known from JP-A 2006-152255. In the formula, X is a leaving group, examples of which include halogen atoms such as chlorine, bromine and iodine, alkanesulfonyloxy groups such as methanesulfonyloxy, arenesulfonyloxy groups such as p-toluenesulfonyloxy, acyloxy groups such as acetoxy, aryloxy groups such as pentafluorophenoxy, and nitrogen-containing leaving groups such as imidazoyl. When R is alkyl, RX is an alkylating agent and the reaction is O-alkylation. When R is acyl, RX is an acylating agent and the reaction is O-acylation. An amount of RX used is desirably 0.3 to 10 moles, and more desirably 0.8 to 5 moles per mole of hemiacetal compound (1').

The reaction may be carried out in a solventless system or in a solvent. Suitable solvents include alcohols such as methanol, ethanol, isopropyl alcohol, t-butyl alcohol and ethylene glycol; hydrocarbons such as hexane, heptane, benzene, toluene and xylene; ethers such as diethyl ether, dibutyl ether, tetrahydrofuran, 1,4-dioxane, and diglyme; chlorinated solvents such as methylene chloride, chloroform, and 1,2-dichloroethylene; aprotic polar solvents such as N,N-dimethylformamide, N,N-dimethylacetamide, dimethyl sulfoxide, and N-methylpyrrolidone; carboxylic acids such as formic acid and acetic acid; esters such as ethyl acetate and butyl acetate; ketones such as acetone and 2-butanone; nitriles such as acetonitrile; amines such as pyridine and triethylamine; and water. Depending on reaction conditions, any of the foregoing solvents may be selected and used alone or in admixture.

The reaction temperature may be selected in the range of −40° C. to the reflux temperature of the solvent, depending on the desired reaction rate. To the reaction system, a base or transition metal salt is preferably added in order to increase the conversion. Suitable bases include amines such as pyridine, triethylamine, diisopropylethylamine, 4-dimethylaminopyridine, and imidazole; metal alkoxides such as sodium methoxide, sodium ethoxide, and potassium t-butoxide; carbonates such as sodium carbonate, potassium carbonate, and cesium carbonate; hydroxides such as sodium hydroxide, potassium hydroxide, and tetramethylammonium hydroxide; metal hydrides such as sodium hydride and potassium hydride; organometallic compounds such as butyllithium and ethyl magnesium bromide; and metal amides such as lithium diisopropylamide. Depending on reaction conditions, any of the foregoing bases may be selected and used alone or in admixture. An amount of the base used is desirably 0.3 to 20 moles, and more desirably 0.8 to 10 moles per mole of hemiacetal compound (1′). Examples of the transition metal salt used herein include lead carbonate, cadmium carbonate, silver carbonate, lead oxide, cadmium oxide, silver oxide, and silver nitrate. Depending on reaction conditions, any of the foregoing salts may be selected and used alone or in admixture. The base and transition metal salt may be used alone or in admixture.

To the reaction system, a catalyst may be added in order to accelerate the reaction rate. Suitable catalysts include iodides such as sodium iodide, lithium iodide, and tetrabutylammonium iodide, and bromides such as sodium bromide, lithium bromide and tetrabutylammonium bromide. When used, an amount of the catalyst added is desirably 0.001 to 2 moles, and more desirably 0.005 to 0.5 mole per mole of hemiacetal compound (1′).

It is desirable from the standpoint of yield that the reaction time is determined so as to drive the reaction to completion by monitoring the reaction process by gas chromatography (GC) or thin-layer chromatography (TLC). Usually, the reaction time is about 0.1 to 100 hours. From the reaction mixture, the desired acetal compound (1) is recovered through an ordinary aqueous workup. If necessary, the compound may be purified by a standard technique such as distillation, chromatography or recrystallization. Alternatively, without aqueous workup, the reaction solution may be purified directly or after the salt resulting from reaction is filtered off. Although the above description refers to compound (1) as a typical example, the synthesis method described herein is applicable to the preparation of any of compounds (2), (3), (4), (2-1), (3-1), (4-1), (2-2), (3-2), and (4-2).

For example, compounds of formulae (2), (3) and (4) are synthesized as follows.

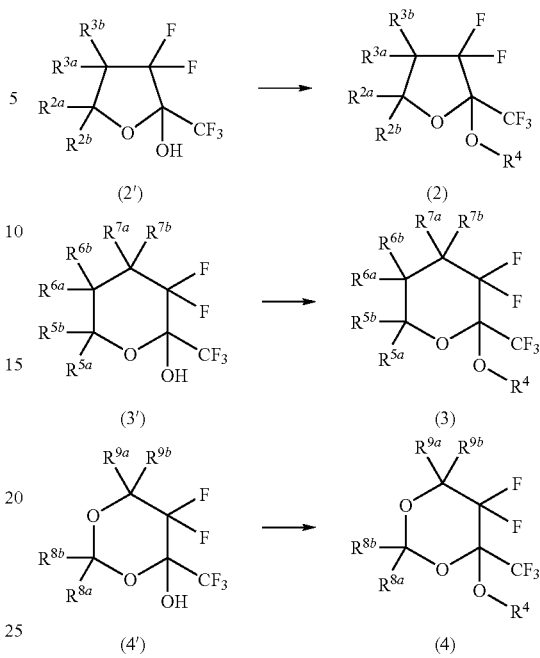

Herein, $R^1$, $R^{2a}$, $R^{2b}$, $R^{3a}$, $R^{3b}$, $R^4$, $R^{5a}$, $R^{5b}$, $R^{6a}$, $R^{6b}$, $R^{7a}$, $R^{7b}$, $R^{8a}$, $R^{8b}$, $R^{9a}$ and $R^{9b}$ are as defined above.

From the fluorinated monomers of cyclic acetal structure represented by formulae (1), (2), (3), (4), (2-1), (3-1), (4-1), (2-2), (3-2), and (4-2), homopolymers may be prepared or copolymers may be prepared through copolymerization with one or more other polymerizable monomers, both by a standard polymerization technique such as radical polymerization, anionic polymerization or cationic polymerization. As to the preparation, any well-known method and conditions for the polymerization of a polymerizable unsaturated bond, especially polymerizable double bond may be selected.

The fluorinated monomer of the invention is useful as a monomer for producing an additive polymer in immersion lithography resist compositions, and a polymer in a protective coating material to be formed on a resist film of immersion lithography resist compositions.

Polymer

The invention also provides a polymer or high-molecular-weight compound comprising recurring units represented by one of the general formulae (5) to (7).

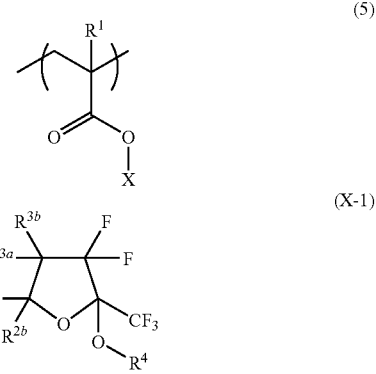

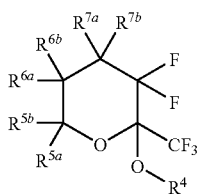 (X-2)

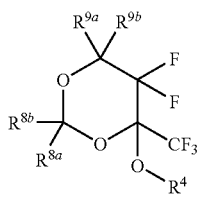 (X-3)

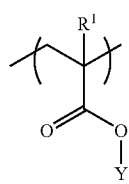 (6)

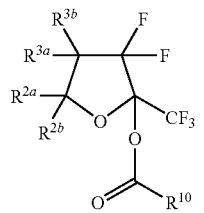 (Y-1)

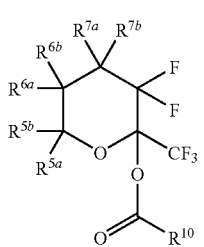 (Y-2)

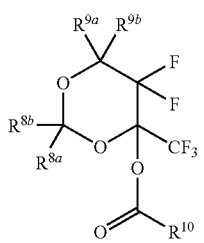 (Y-3)

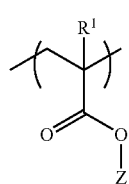 (7)

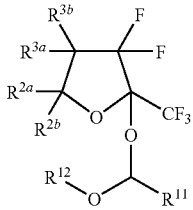 (Z-1)

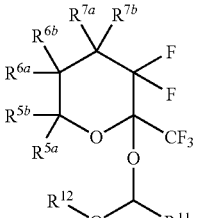 (Z-2)

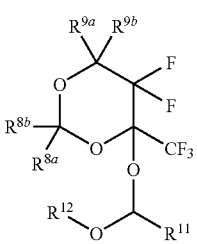 (Z-3)

Herein $R^1$ is hydrogen, methyl or trifluoromethyl. X is a structure having the general formula (X-1), (X-2) or (X-3), Y is a structure having the general formula (Y-1), (Y-2) or (Y-3), and Z is a structure having the general formula (Z-1), (Z-2) or (Z-3).

In formula (X-1), (Y-1) and (Z-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached. The structure (X-1), (Y-1) or (Z-1) is linked to the —(C=O)—O— linkage in recurring unit (5), (6) or (7) via any one of $R^{2a}$, $R^{2b}$, $R^{3a}$, and $R^{3b}$.

In formula (X-2), (Y-2) and (Z-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached. The structure (X-2), (Y-2) or (Z-2) is linked to the —(C=O)—O— linkage in recurring unit (5), (6) or (7) via any one of $R^{5a}$, $R^{5b}$, $R^{6a}$, $R^{6b}$, $R^{7a}$, and $R^{7b}$.

In formula (X-3), (Y-3) and (Z-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached. The structure (X-3), (Y-3) or (Z-3) is linked to the —(C=O)—O— linkage in recurring unit (5), (6) or (7) via any one of $R^{8a}$, $R^{8b}$, $R^{9a}$, and $R^{9b}$.

$R^4$ is a straight, branched or cyclic $C_1$-$C_{20}$ alkyl group in which at least one hydrogen atom may be substituted by a halogen atom or at least one methylene moiety may be substituted by an oxygen atom or carbonyl group. $R^{10}$ is a straight, branched or cyclic $C_1$-$C_{19}$ alkyl group in which at least one hydrogen atom may be substituted by a halogen atom or at least one methylene moiety may be substituted by an oxygen atom or carbonyl group. $R^{11}$ is hydrogen or a straight, branched or cyclic $C_1$-$C_{18}$ alkyl group in which at least one hydrogen atom may be substituted by a halogen atom or at least one methylene moiety may be substituted by an oxygen atom or carbonyl group, $R^{12}$ is a straight, branched or cyclic $C_1$-$C_{19}$ alkyl group in which at least one hydrogen atom may be substituted by a halogen atom or at least one methylene moiety may be substituted by an oxygen atom or carbonyl group, or $R^{11}$ and $R^{12}$ may bond together to form a cyclic structure with the carbon and oxygen atoms to which they are attached.

It is noted that when the structure of X, Y or Z is linked to the —(C=O)—O— linkage in recurring unit (5), (6) or (7) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

More specifically, examples of the straight, branched or cyclic $C_1$-$C_{15}$ monovalent organic groups represented by $R^{2a}$, $R^{2b}$, $R^{3a}$ and $R^{3b}$ in formulae (X-1), (Y-1) and (Z-1) are as illustrated above, and $R^{5a}$ through $R^{9b}$ are also as illustrated above.

Examples of $R^4$ are as illustrated above although preferred examples are —CO—$R^{10}$ and —CH($R^{11}$)—O$R^{12}$. Examples of the alkyl groups of $R^{10}$, $R^{11}$ and $R^{12}$ are as illustrated above.

Illustrative examples of recurring units of formulae (5), (6) and (7) are given below, but not limited thereto.

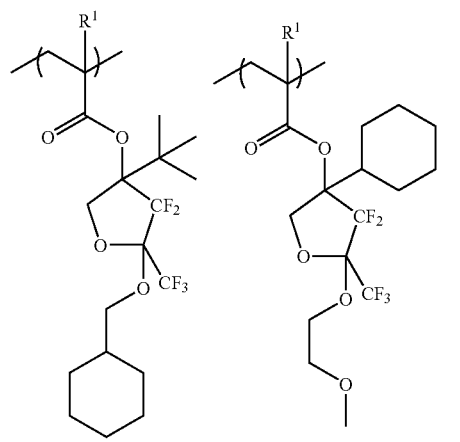

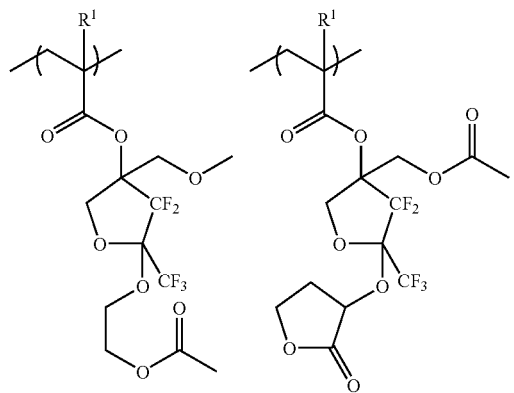

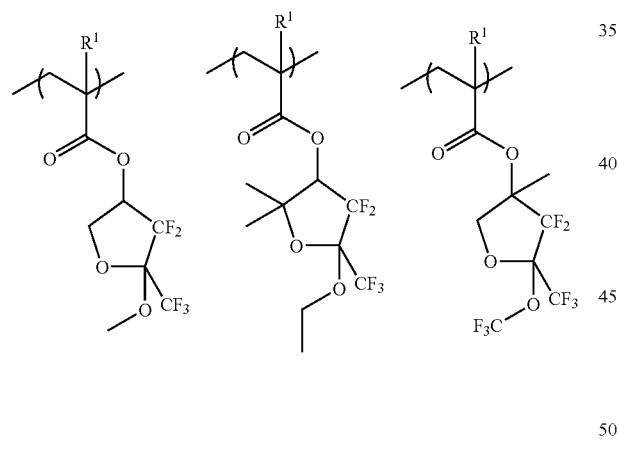

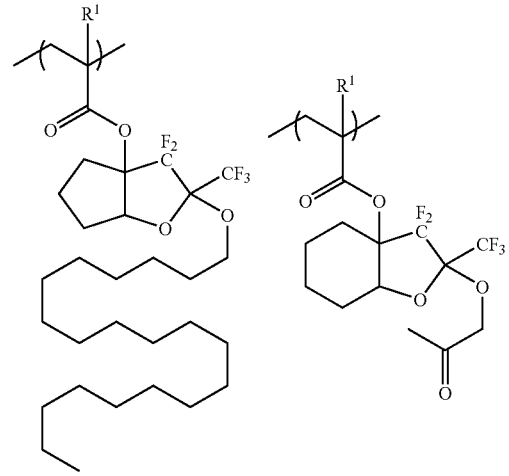

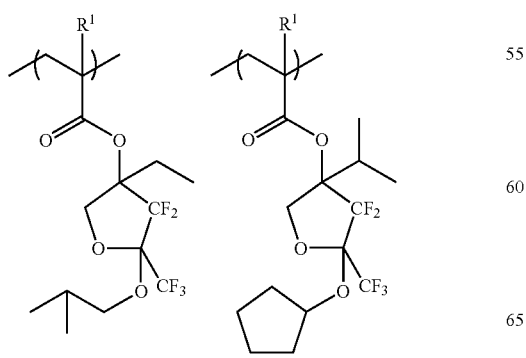

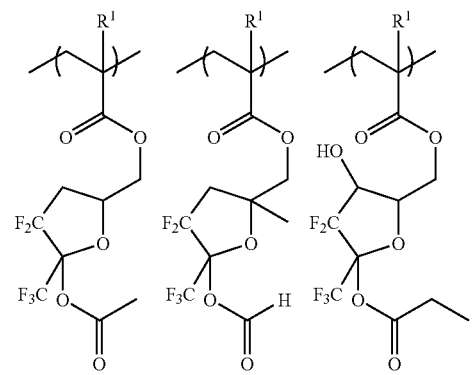

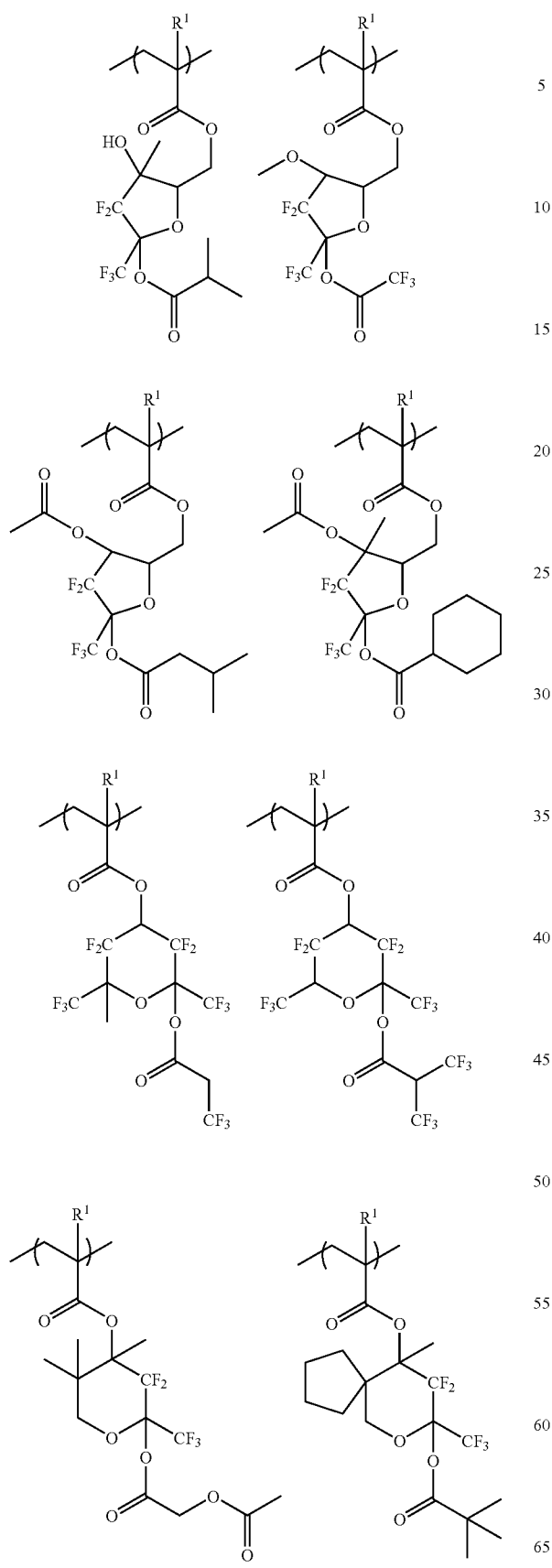
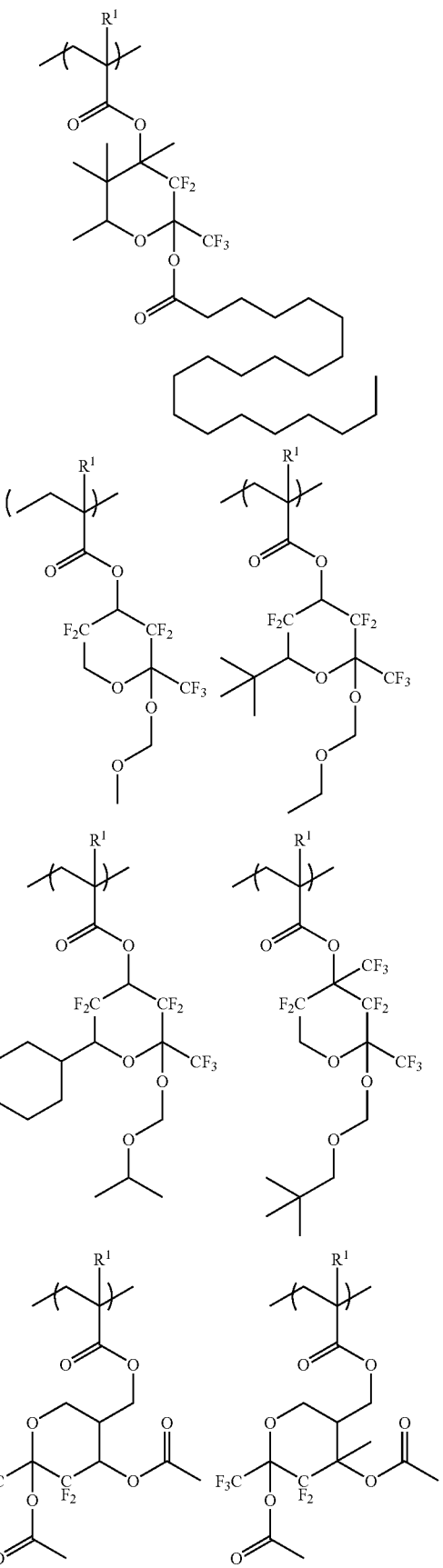

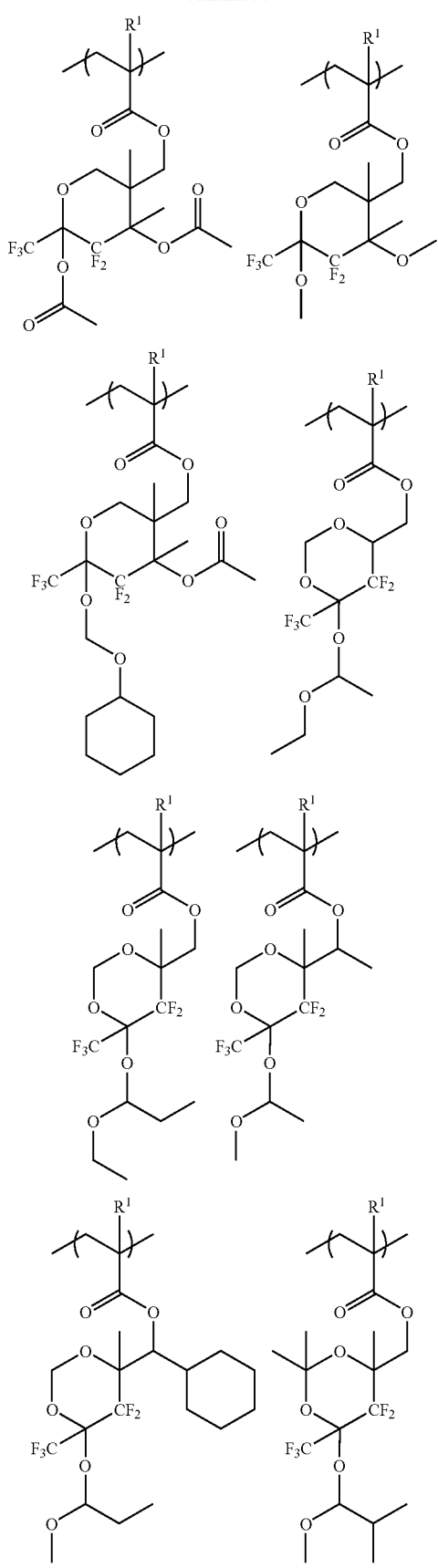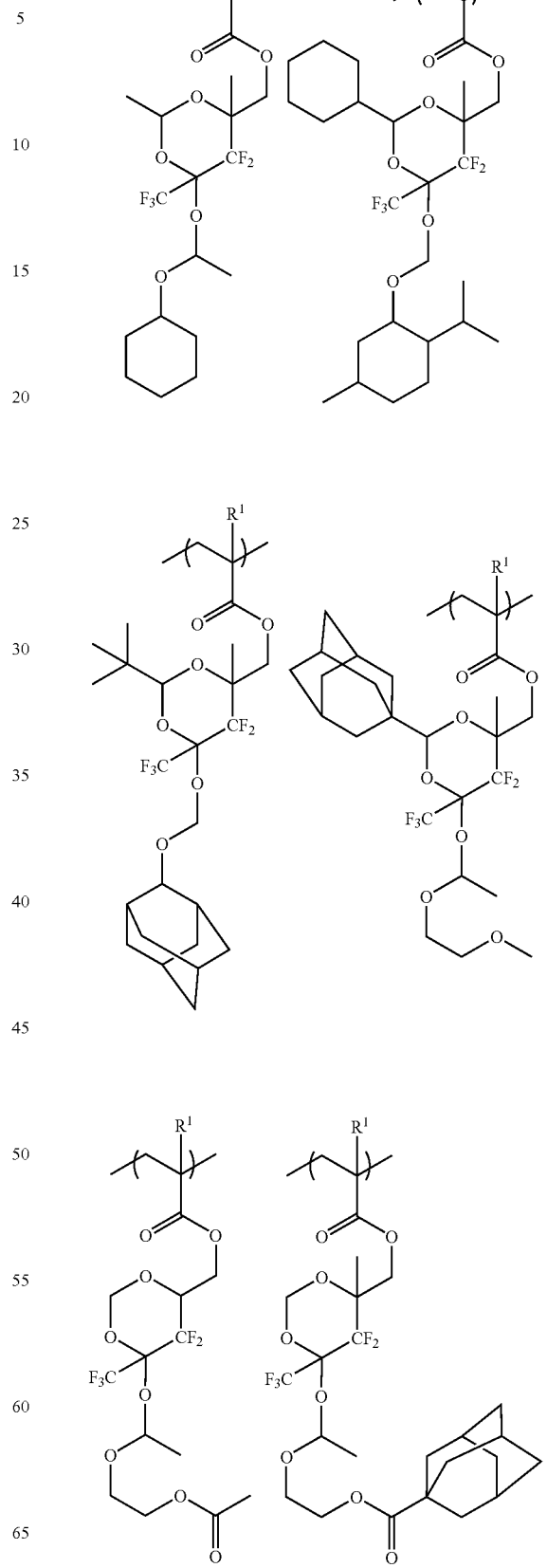

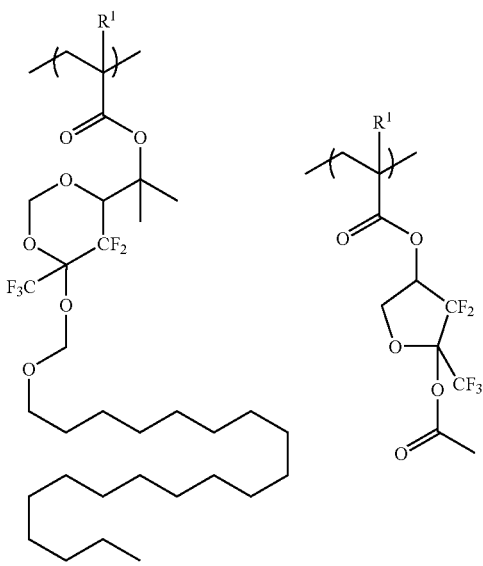
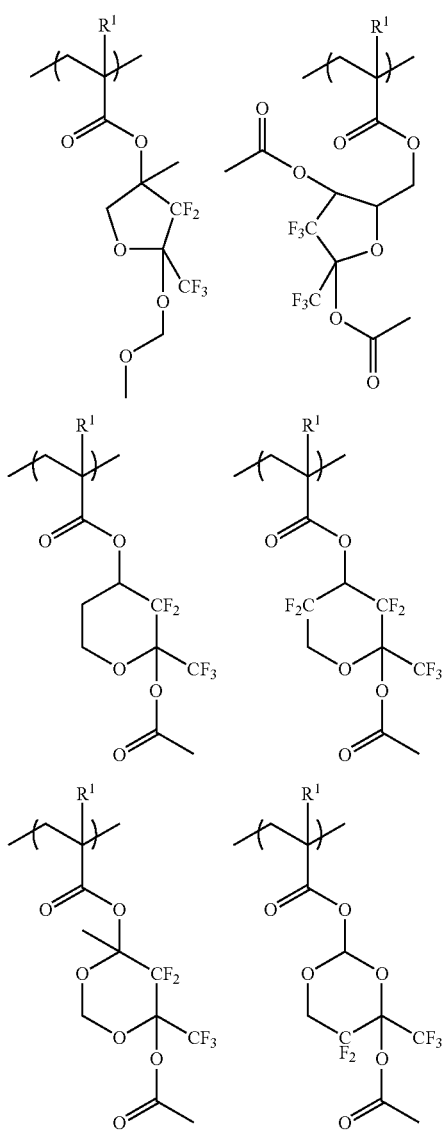
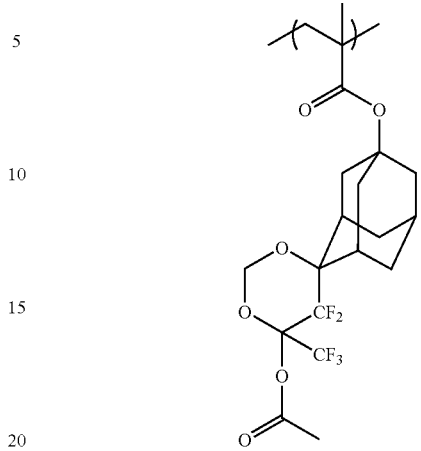

Herein $R^1$ is as illustrated above.

In the polymers, recurring units of formula (5), (6) or (7) exert an effect in water repellency and water sliding property. In the polymer comprising recurring units of formula (5), (6) or (7), it is easy to control structural parameters including carbon chain length, branching degree and fluorine number in $R^4$ in formula (5), $R^{10}$ in formula (6), or $R^{11}$ and $R^{12}$ in formula (7). This ensures preparation of a polymer having appropriate water repellency and water sliding property as required of the resist protective coating material.

The polymer may be endowed with alkaline hydrolyzability if necessary. In such a case, inclusion of recurring units of formula (6) is preferred. Hemiacetal hydroxyl group has a higher acidity than alcoholic hydroxyl group. Since the ester bond in formula (6) is an ester between a carboxylic acid and a hemiacetal hydroxyl group having a further higher acidity as a result of five fluorine atoms bonding to vicinal carbon atoms, and thus regarded as mixed acid anhydride, this ester is highly susceptible to alkaline hydrolysis as compared with esters of carboxylic acid with ordinary alcohol. It is thus believed that this ester is readily hydrolyzed with an alkaline developer, for example.

Also the polymer may be endowed with acid lability if necessary. In such a case, inclusion of recurring units of formula (7) is preferred. It is believed that the acid labile acetal structure (—O—CH($R^{11}$)—O$R^{12}$) included in formula (7) will be readily decomposed if an acid generated by an acid generator is present in proximity thereto.

When the ester bond in formula (6) is hydrolyzed or the acetal structure in formula (7) is decomposed, a highly hydrophilic hemiacetal structure forms whereby the contact angle at polymer surface is reduced, especially the contact angle at polymer surface after development is reduced, contributing to a reduction of blob defects.

In the embodiment wherein the polymer is for use in protective coating material, a polymer having improved water repellency, water sliding property, alkaline solubility and contact angle after development can be produced by incorporating recurring units of one or more type selected from formulae (8a) to (8f) in addition to the recurring units of formula (5), (6) or (7).

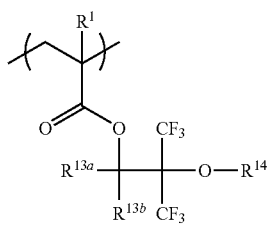
(8a)

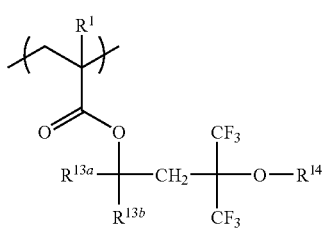
(8b)

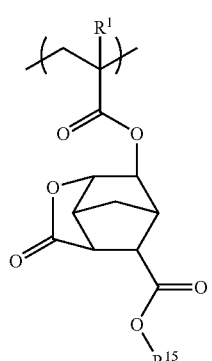
(8c)

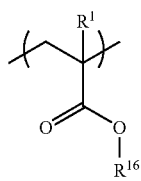
(8d)

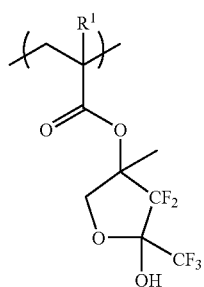
(8e)

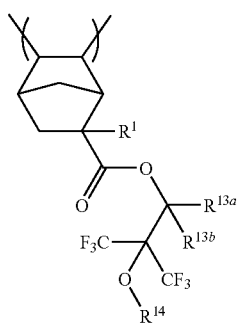
(8f)

Herein $R^1$ is hydrogen, methyl or trifluoromethyl. $R^{13a}$ and $R^{13b}$ each are hydrogen or a straight, branched or cyclic $C_1$-$C_{15}$ alkyl group, or $R^{13a}$ and $R^{13b}$ may bond together to form a ring with the carbon atom to which they are attached. $R^{14}$ is hydrogen, a straight, branched or cyclic $C_1$-$C_{15}$ alkyl or fluoroalkyl group, or an acid labile group. $R^{15}$ is a straight, branched or cyclic $C_1$-$C_{15}$ fluoroalkyl group. $R^{16}$ is an acid labile group.

In formulae (8a) to (8f), examples of the straight, branched or cyclic $C_1$-$C_{15}$ alkyl groups represented by $R^{13a}$, $R^{13b}$ and $R^{14}$ include methyl, ethyl, n-propyl, isopropyl, n-butyl, sec-butyl, tert-butyl, tert-amyl, n-pentyl, n-hexyl, n-heptyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, cyclohexylbutyl, and adamantyl. $R^{13a}$ and $R^{13b}$ may bond together to form a non-aromatic ring with the carbon atom to which they are attached. In this case, $R^{13a}$ and $R^{13b}$ each are an alkylene group, examples of which are the foregoing alkyl groups with one hydrogen atom eliminated, and exemplary rings include cyclopentyl and cyclohexyl.

The $C_1$-$C_{15}$ fluoroalkyl group represented by $R^{14}$ and $R^{15}$ are the foregoing alkyl groups in which some or all hydrogen atoms are substituted by fluorine atoms. Examples include trifluoromethyl, 2,2,2-trifluoroethyl, 3,3,3-trifluoropropyl, 1,1,2,2,3,3,3-heptafluoropropyl, 1H,1H,3H-tetrafluoropropyl, 1H,1H,5H-octafluoropentyl, 1H,1H,7H-dodecafluoroheptyl, 2-(perfluorobutyl)ethyl, 2-(perfluorohexyl)ethyl, 2-(perfluorooctyl)ethyl, and 2-(perfluorodecyl)ethyl.

The acid labile group represented by $R^{14}$ and $R^{16}$ may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

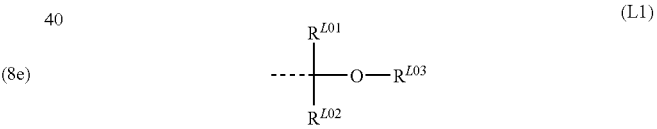
(L1)

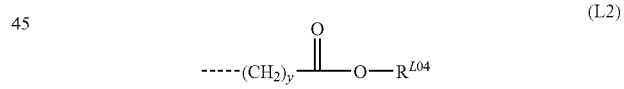
(L2)

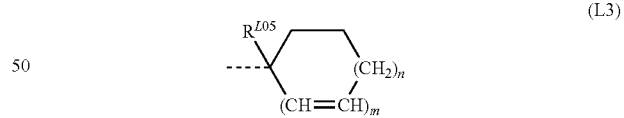
(L3)

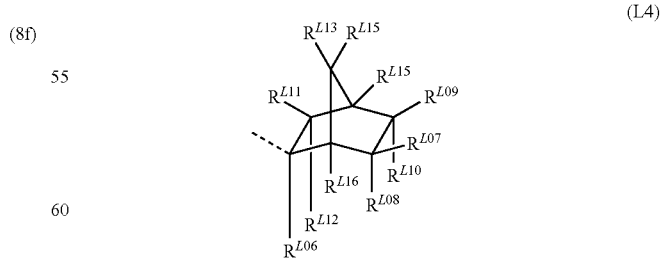
(L4)

Herein $R^{L01}$ and $R^{L02}$ are hydrogen or straight, branched or cyclic alkyl groups of 1 to 18 carbon atoms, preferably 1 to 10 carbon atoms. $R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). $R^{L05}$ is an optionally substituted, straight, branched or cyclic $C_1$-$C_{10}$ alkyl group or an optionally substituted $C_6$-$C_{20}$ aryl group. $R^{L06}$ is an optionally substituted, straight, branched or cyclic $C_1$-$C^{10}$ alkyl group or an optionally substituted $C_6$-$C_{20}$ aryl group. $R^{L07}$ to $R^{L16}$ independently represent hydrogen or monovalent hydrocarbon groups of 1 to 15 carbon atoms. Letter y is an integer of 0 to 6, m is equal to 0 or 1, n is equal to 0, 1, 2 or 3, and 2m+n is equal to 2 or 3. The broken line denotes a valence bond.

In formula (L1), exemplary groups of $R^{L01}$ and $R^{L02}$ include methyl, ethyl, propyl, isopropyl, n-butyl, sec-butyl, tert-butyl, cyclopentyl, cyclohexyl, 2-ethylhexyl, n-octyl, and adamantyl. $R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples of the straight, branched or cyclic alkyl groups are as exemplified above for $R^{L01}$ and $R^{L02}$, and examples of the substituted alkyl groups are as shown below.

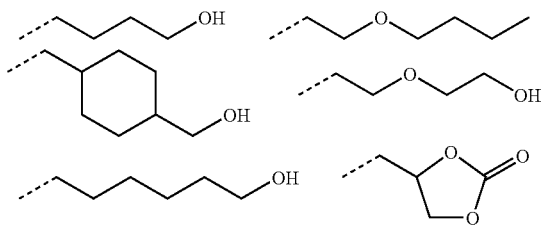

A pair of $R^{L01}$ and $R^{L02}$, $R^{L01}$ and $R^{L03}$, or $R^{L02}$ and $R^{L03}$ may bond together to form a ring with carbon and oxygen atoms to which they are attached. Each of ring-forming $R^{L01}$, $R^{L02}$ and $R^{L03}$ is a straight or branched alkylene group of 1 to 18 carbon atoms, preferably 1 to 10 carbon atoms when they form a ring.

In formula (L2), exemplary tertiary alkyl groups of $R^{L04}$ are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, and the like. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl.

In formula (L3), examples of the optionally substituted alkyl groups of $R^{L05}$ include straight, branched or cyclic alkyl groups such as methyl, ethyl, propyl, isopropyl, n-butyl, sec-butyl, tert-butyl, tert-amyl, n-pentyl, n-hexyl, cyclopentyl, cyclohexyl, and bicyclo[2.2.1]heptyl, and substituted forms of such groups in which some hydrogen atoms are replaced by hydroxyl, alkoxy, carboxy, alkoxycarbonyl, oxo, amino, alkylamino, cyano, mercapto, alkylthio, sulfo or other groups or in which some methylene groups are replaced by oxygen or sulfur atoms. Examples of optionally substituted $C_6$-$C_{20}$ aryl groups include phenyl, methylphenyl, naphthyl, anthryl, phenanthryl, and pyrenyl.

In formula (L4), examples of optionally substituted, straight, branched or cyclic $C_1$-$C_{10}$ alkyl groups and optionally substituted $C_6$-$C_{20}$ aryl groups of $R^{L06}$ are the same as exemplified for $R^{L05}$. Exemplary $C_1$-$C_{15}$ hydrocarbon groups of $R^{L07}$ to $R^{L16}$ are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom(s) to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are those exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

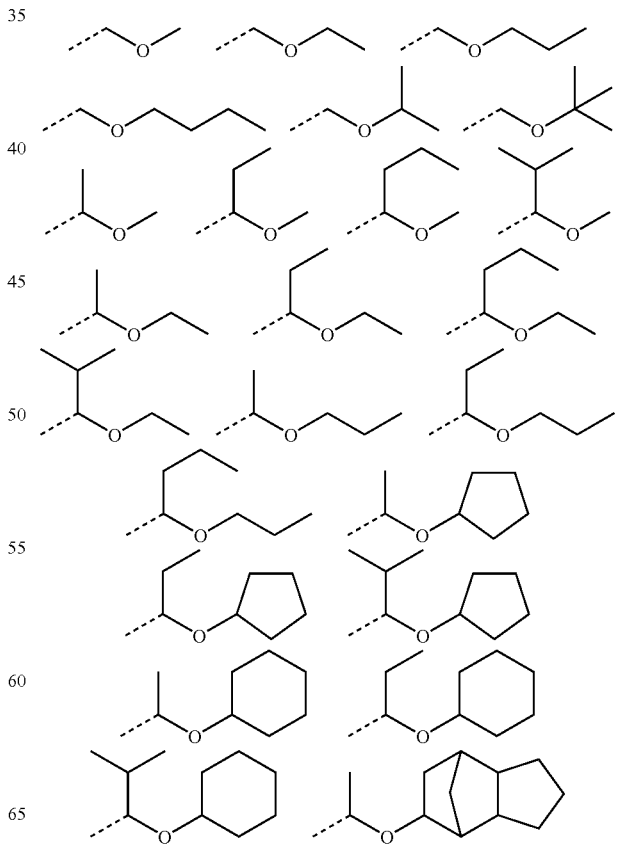

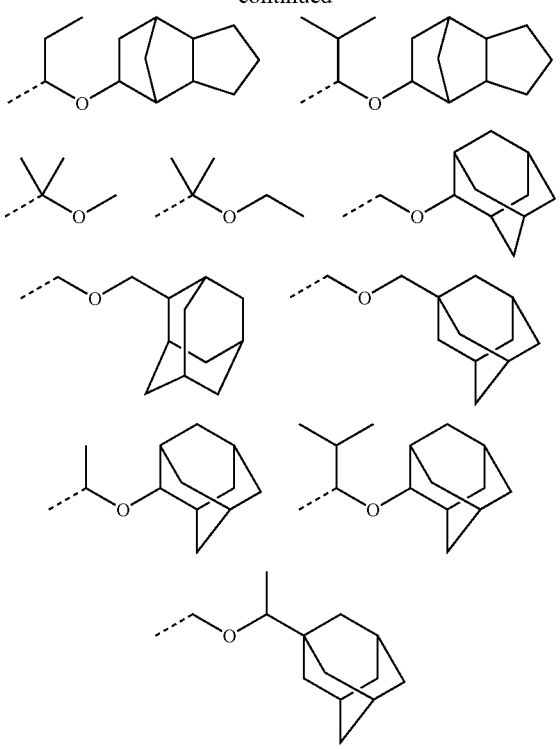

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-(bicyclo[2.2.1]heptan-2-yl)cyclopentyl, 1-(7-oxabicyclo[2.2.1]heptan-2-yl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are preferred.

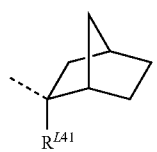
(L4-1)

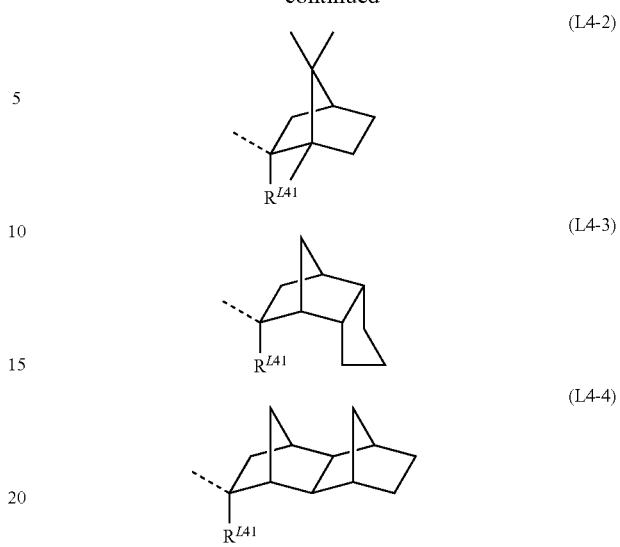

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

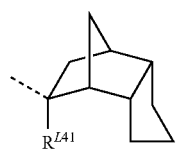
(L4-3-1)

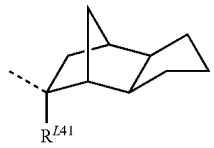
(L4-3-2)

Note that $R^{L41}$ is as defined above.

Similarly, the general formula (L4-4) represents one or a mixture of two or more selected from groups having the following general formulas (L4-4-1) to (L4-4-4).

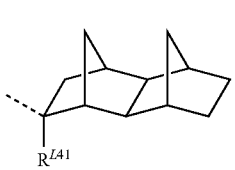
(L4-4-1)

-continued

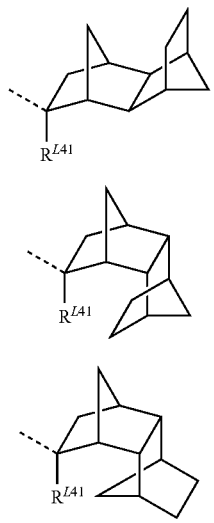

Note that $R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane structure as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

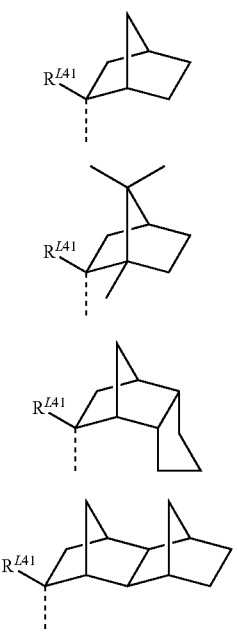

Note that $R^{L41}$ is as defined above.

Illustrative examples of the acid labile group of formula (L4) are given below.

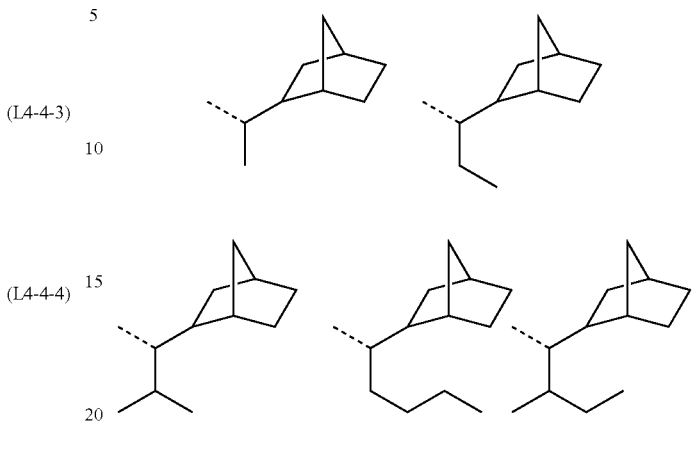

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups, represented by $R^3$, are as exemplified for $R^{L04}$ and the like.

Illustrative examples of the recurring units of formulae (8a) to (8f) are given below, but not limited thereto.

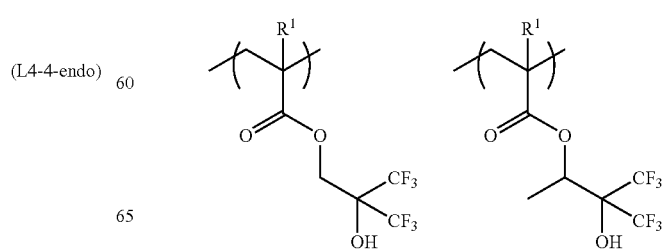

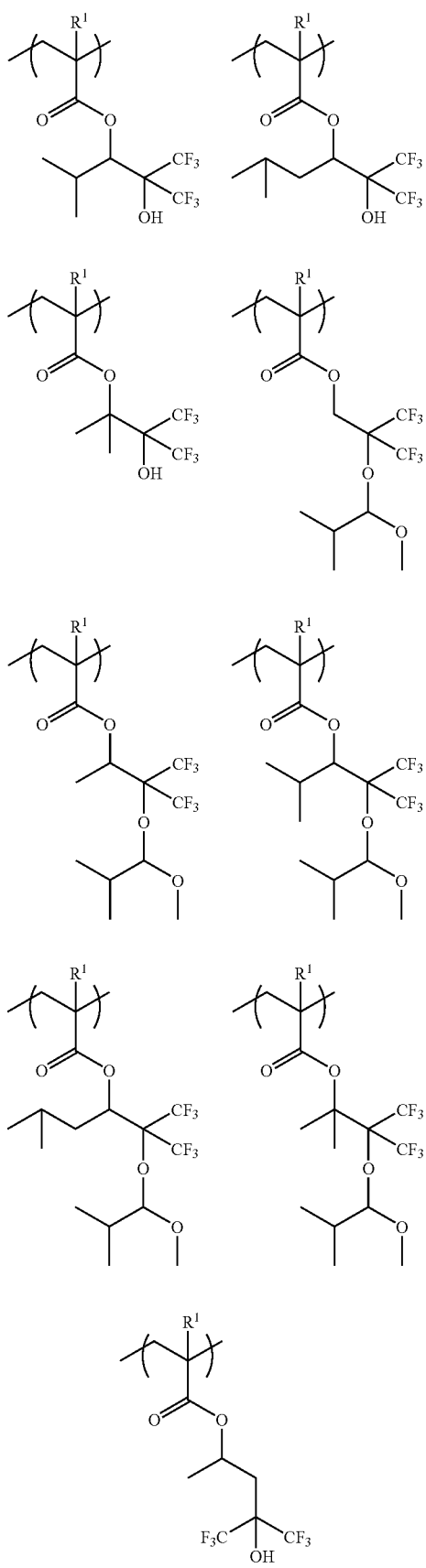
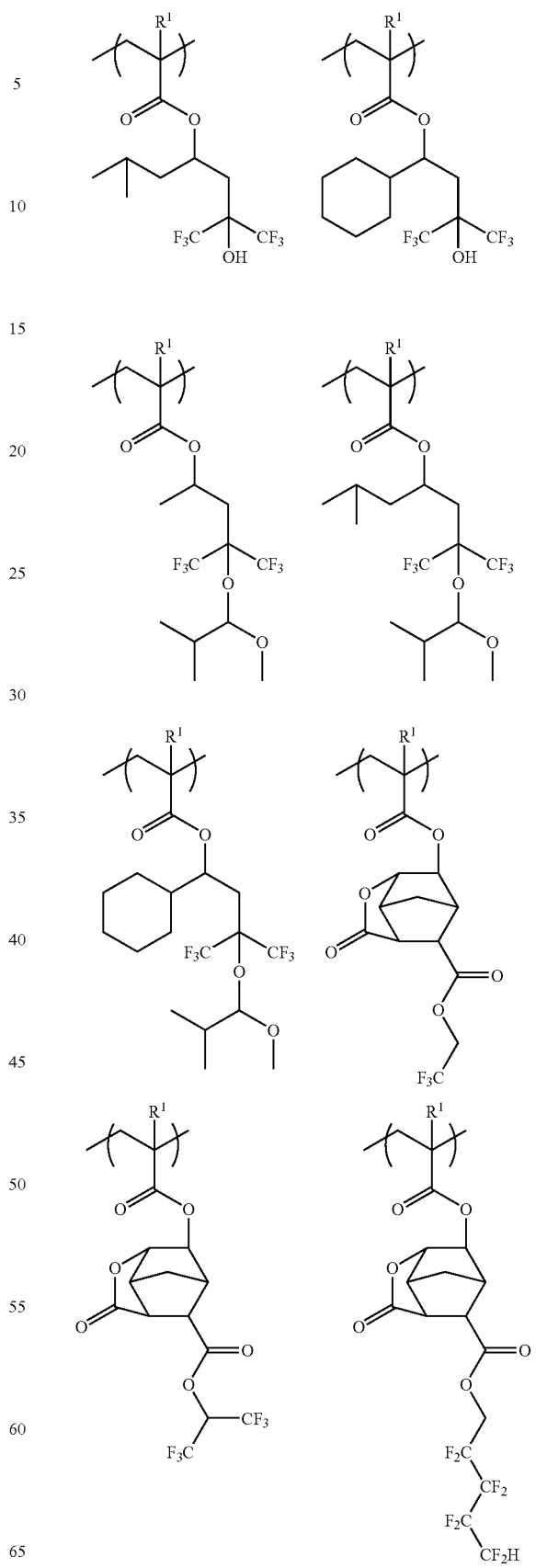

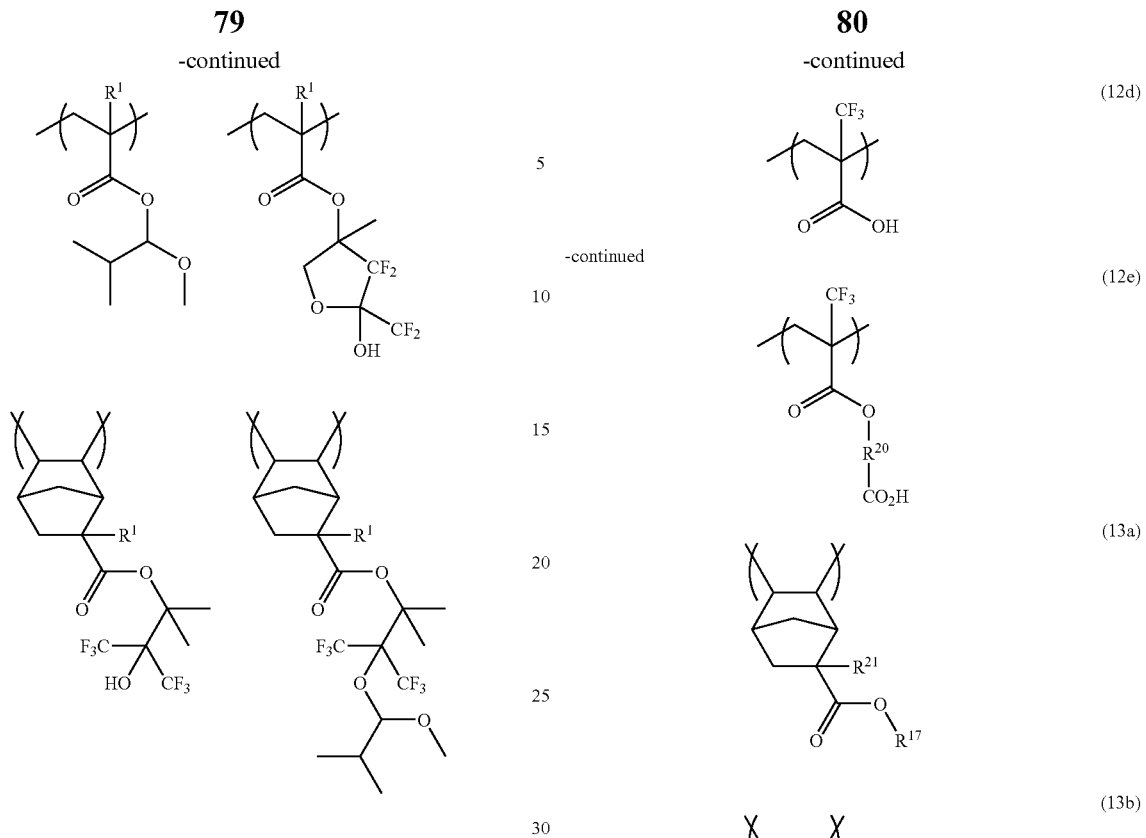

Herein $R^1$ is as defined above.

Although the polymer comprising recurring units of formulae (5) to (7) in combination with recurring units of formulae (8a) to (8f) exerts satisfactory performance, recurring units of one or more types selected from formulae (12a) to (12e), (13a) to (13e), (14a) to (14c), and (15a) to (15c) may be further incorporated therein for the purposes of imparting further water repellency and water sliding property, and controlling alkaline solubility and developer affinity.

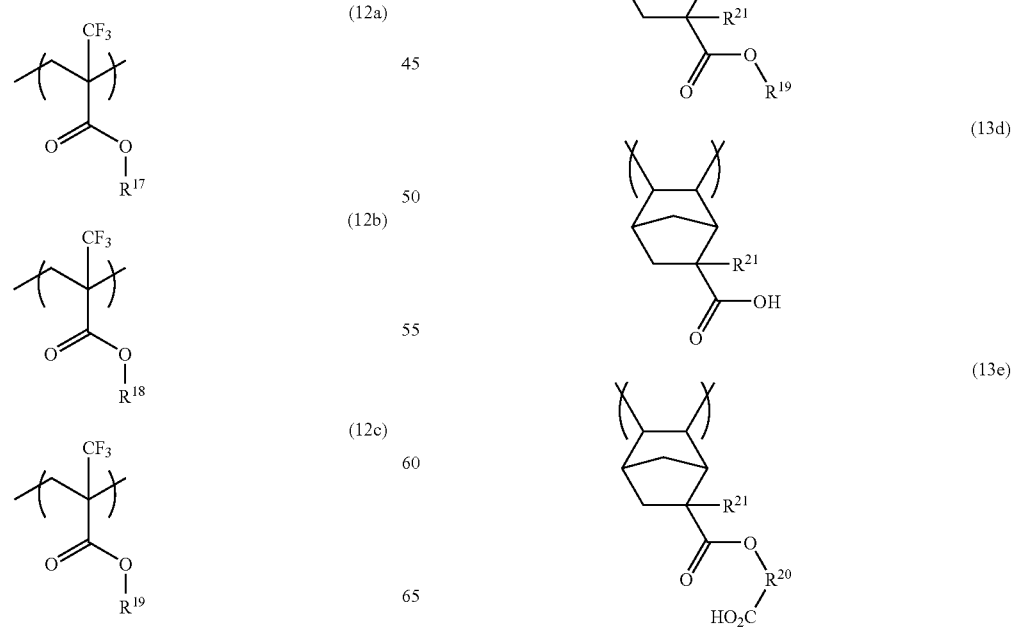

(14a) 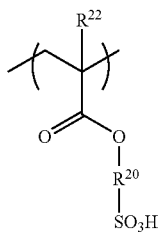

(14b) 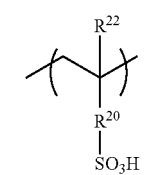

(14c) 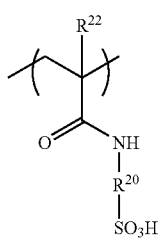

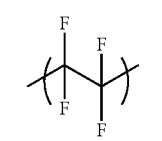

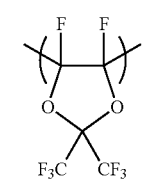

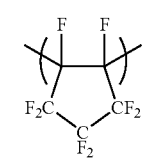

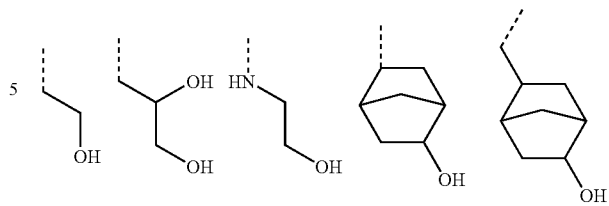

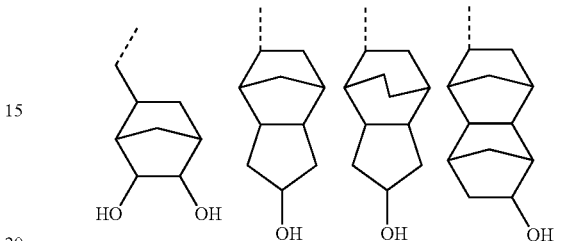

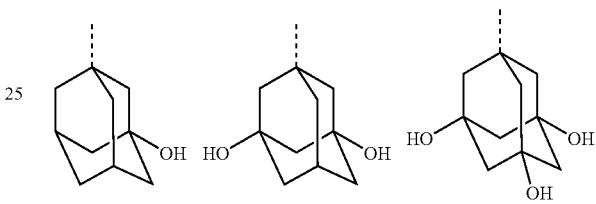

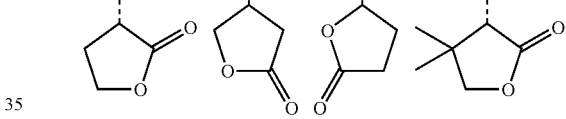

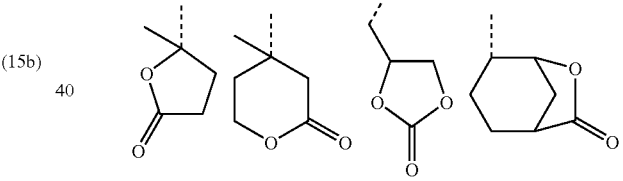

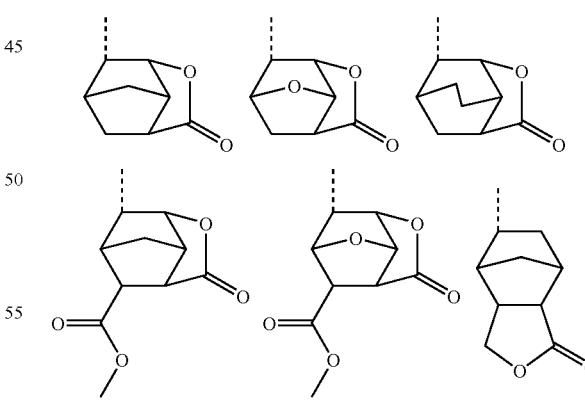

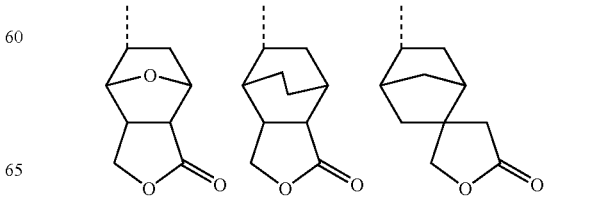

Herein $R^{17}$ is a $C_1$-$C_{15}$ alkyl or fluoroalkyl group, $R^{18}$ is an adhesive group, $R^{19}$ is an acid labile group, $R^{20}$ is a single bond or divalent $C_1$-$C_{15}$ organic group, and $R^{21}$ and $R^{22}$ each are hydrogen, methyl or trifluoromethyl.

Examples of the $C_1$-$C_{15}$ alkyl or fluoroalkyl group represented by $R^{17}$ are the same as illustrated for formulae (8a) to (8f).

The adhesive group represented by $R^{18}$ may be selected from a variety of such groups, typically those groups shown below.

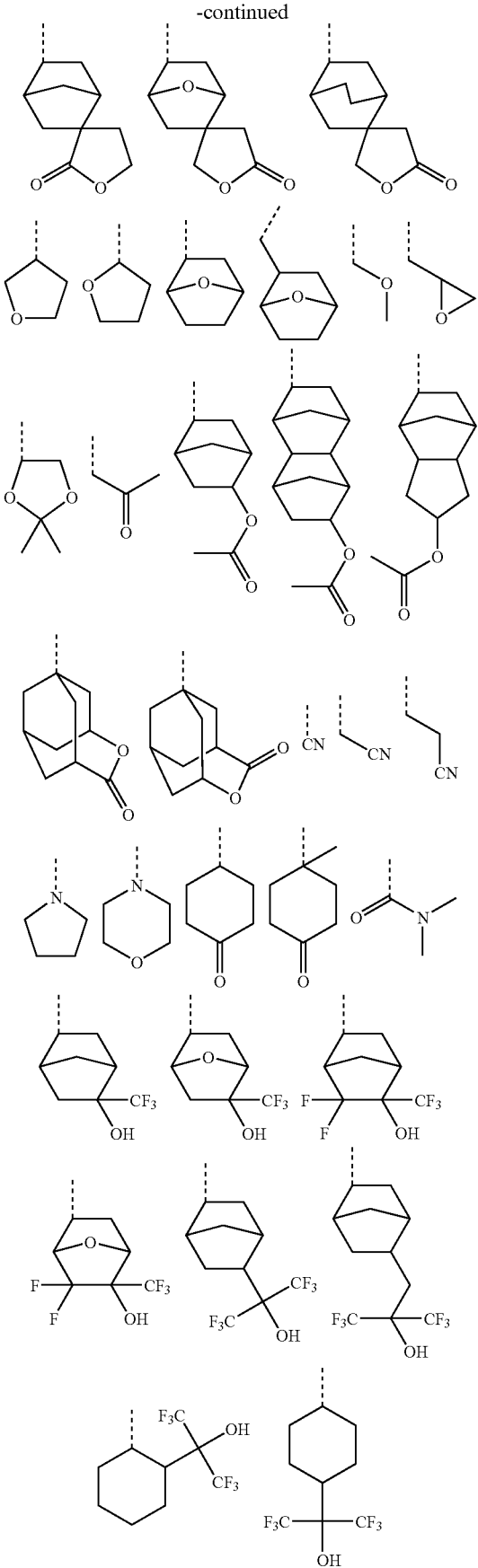

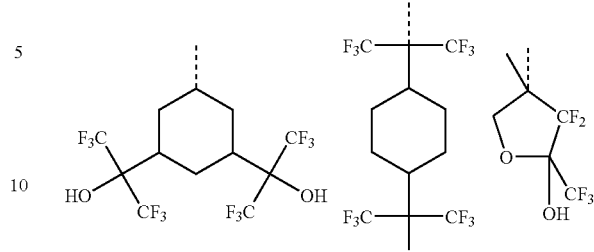

Herein, the broken line designates a valence bond.

The acid labile group represented by $R^{19}$ may be selected from those groups illustrated for $R^{14}$ and $R^{16}$.

Suitable divalent $C_1$-$C_{15}$ organic groups represented by $R^{20}$ include the above-illustrated alkyl groups with one hydrogen atom eliminated (e.g., methylene and ethylene) and groups of the following formulae.

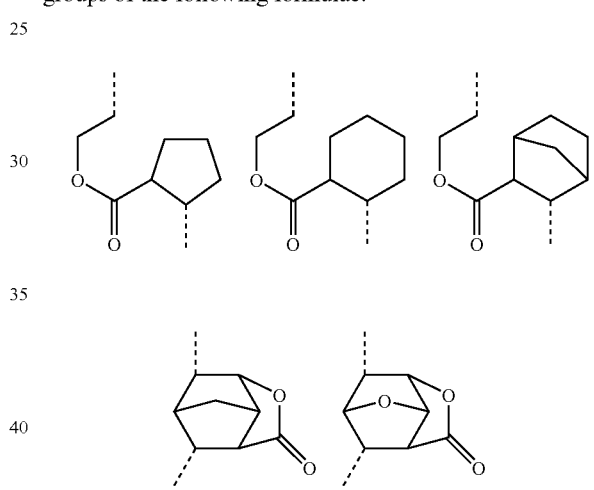

Herein, the broken line designates a valence bond.

The polymer of the invention exerts satisfactory performance even when used alone. In a preferred embodiment, a second polymer comprising recurring units of at least one type selected from formulae (9) to (11) may be used in blend with the inventive polymer for the purposes of imparting further water repellency and water sliding property, and controlling alkaline solubility and developer affinity.

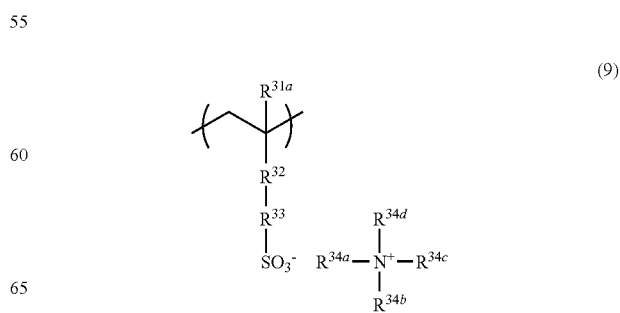

(9)

-continued

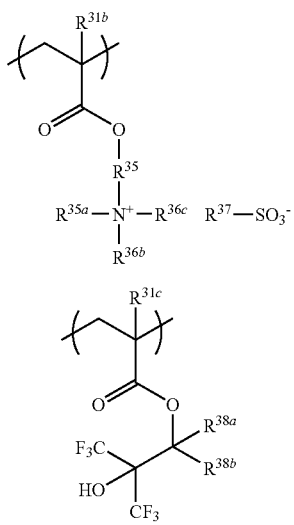

(10)

(11)

Herein $R^{31a}$ to $R^{31c}$ are hydrogen or methyl. $R^{32}$ is a single bond, $C_1$-$C_4$ alkylene, phenylene, —C(=O)—O—, or —C(=O)—NH—. $R^{33}$ is a single bond or a straight, branched or cyclic $C_1$-$C_8$ alkylene group. $R^{34a}$ to $R^{34d}$ and $R^{36a}$ to $R^{36c}$ are each independently hydrogen, a straight, branched or cyclic $C_1$-$C_{12}$ alkyl, alkenyl, oxoalkyl or oxoalkenyl group, $C_6$-$C_{20}$ aryl group, or $C_7$-$C_{12}$ aralkyl or aryloxoalkyl group, in which some or all hydrogen atoms may be substituted by alkoxy groups, $R^{34a}$ to $R^{34d}$ and $R^{36a}$ to $R^{36c}$ may contain a nitrogen atom, ether group, ester group, hydroxyl group or carboxyl group therein, any two of $R^{34a}$ to $R^{34d}$ and $R^{36a}$ to $R^{36c}$ may bond together to form a ring with the nitrogen atom to which they are attached, and when they form a ring, they are each independently a $C_3$-$C_{15}$ alkylene or a hetero-aromatic ring having the nitrogen atom therein. $R^{35}$ is a straight, branched or cyclic $C_1$-$C_8$ alkylene group. $R^{37}$ is a straight, branched or cyclic $C_1$-$C_{20}$ alkyl group which may contain carbonyl, ester, ether or halogen, or a $C_6$-$C_{15}$ aryl group which may contain carbonyl, ester, ether, halogen, or $C_1$-$C_{15}$ alkyl or fluoroalkyl. $R^{38a}$ and $R^{38b}$ are hydrogen or a straight, branched or cyclic $C_1$-$C_{15}$ alkyl group, or $R^{38a}$ and $R^{38b}$ may bond together to form a ring with the carbon atom to which they are attached.

Examples of the $C_1$-$C_4$ alkylene group represented by $R^{32}$ include methyl, ethyl, n-propyl, isopropyl, n-butyl, sec-butyl and tert-butyl groups, with one hydrogen atom eliminated.

Examples of the straight, branched or cyclic $C_1$-$C_8$ alkylene group represented by $R^{33}$ and $R^{35}$ include methyl, ethyl, n-propyl, isopropyl, n-butyl, sec-butyl, tert-butyl, tert-amyl, n-pentyl, n-hexyl, n-heptyl, n-octyl, cyclopentyl, cyclohexyl, cyclopentylmethyl, cyclopentylethyl, cyclohexylmethyl and cyclohexylethyl groups, with one hydrogen atom eliminated.

In formula (9), the ammonium salt (cationic moiety) formed by $R^{34a}$ to $R^{34d}$ is obtained from neutralization reaction of a corresponding amine compound. Suitable amine compounds include primary, secondary and tertiary aliphatic amines, mixed amines, aromatic amines, heterocyclic amines, nitrogen-containing compound having carboxyl group, nitrogen-containing compound having sulfonyl group, nitrogen-containing compound having hydroxyl group, nitrogen-containing compound having hydroxyphenyl group, amides, imides, and carbamates. Illustrative examples of the amine compound which can be used herein include those described in JP-A 2008-111103, paragraphs [0146] to [0164].

Examples of $R^{36a}$ to $R^{36c}$ and $R^{37}$ will become apparent from illustrative examples of formula (10).

Examples of the $C_1$-$C_{15}$ alkyl group represented by $R^{38a}$ and $R^{39b}$ are the same as illustrated for formulae (8a) to (8f).

Illustrative examples of the recurring units of formula (9) are given below, but not limited thereto.

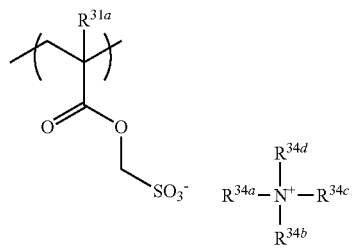

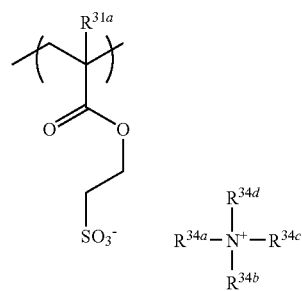

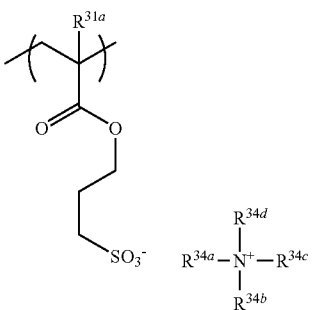

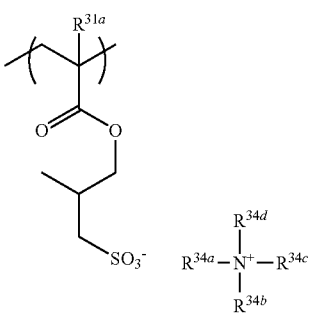

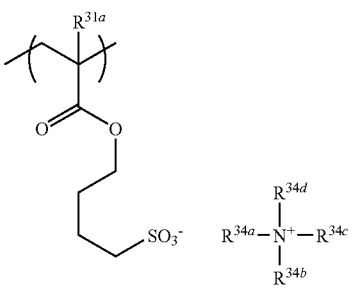

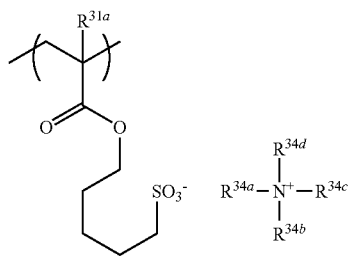
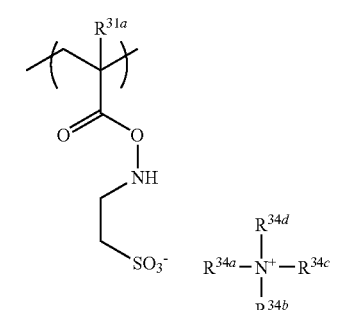
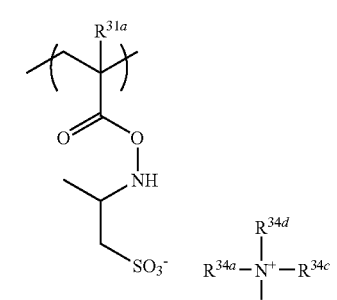
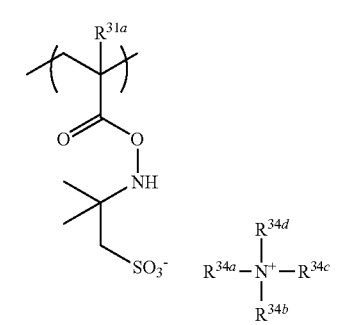
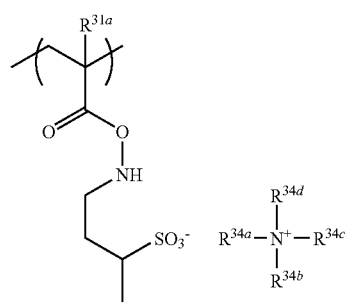
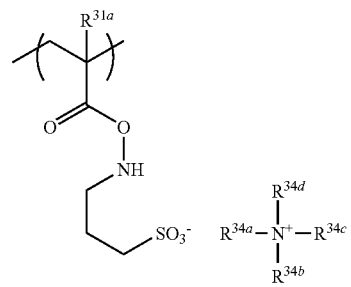
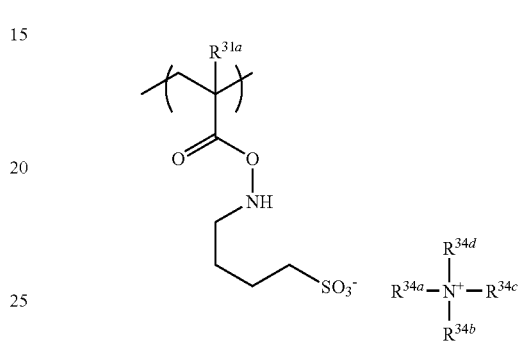
Herein $R^{31a}$ and $R^{34a}$ to $R^{34d}$ are as defined above.
Illustrative examples of the recurring units of formula (10) are given below, but not limited thereto.
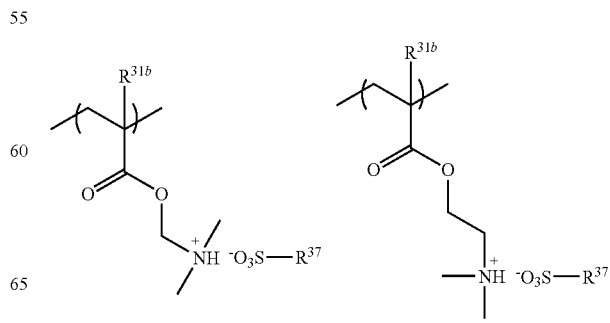

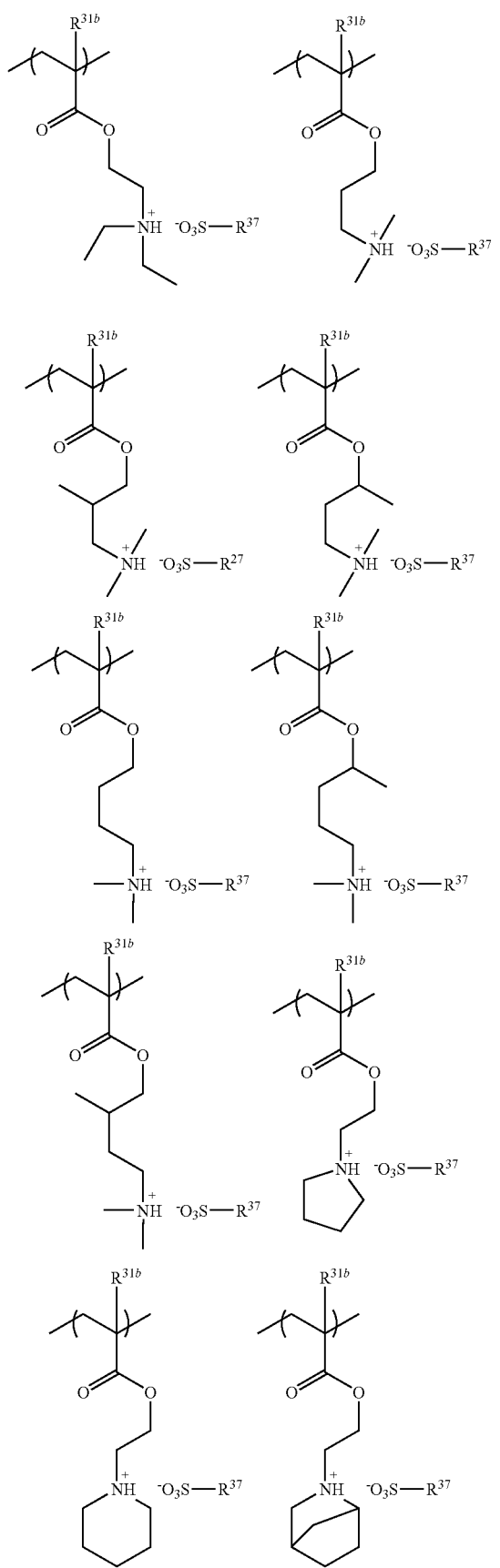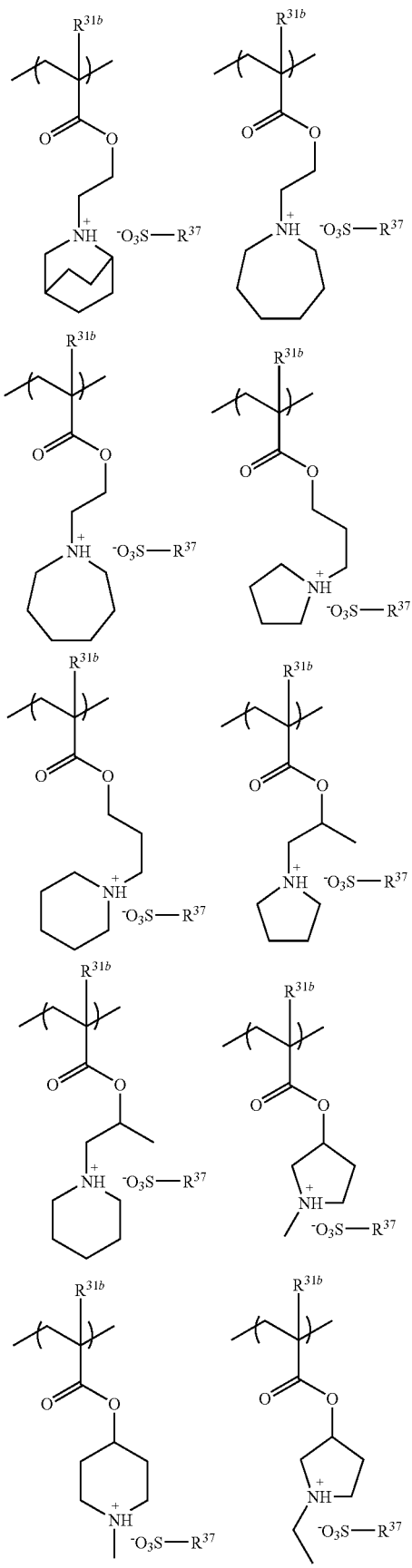

-continued

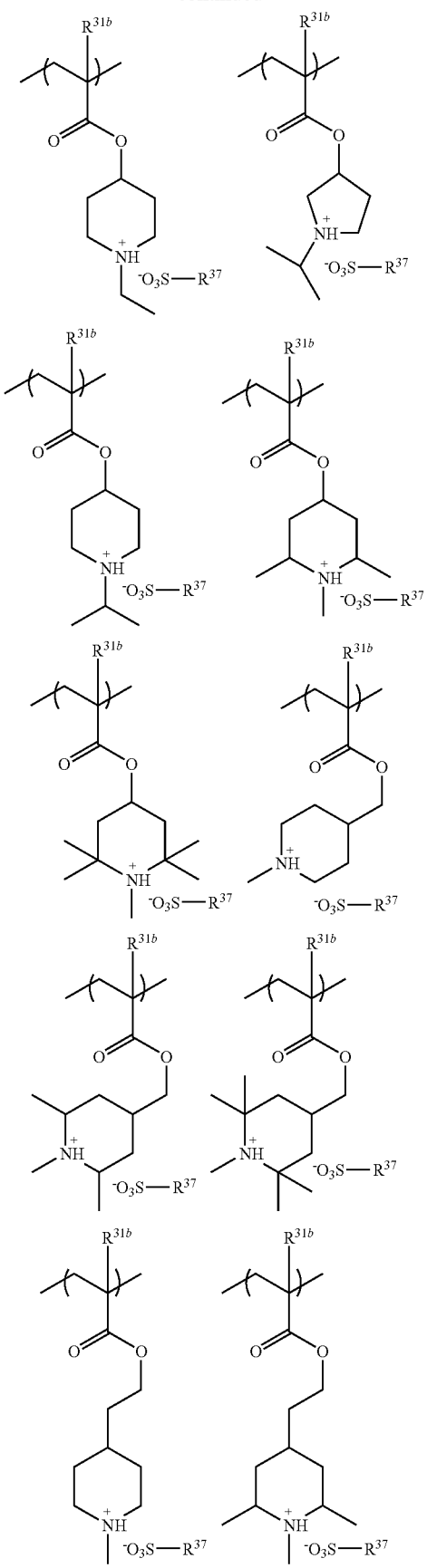
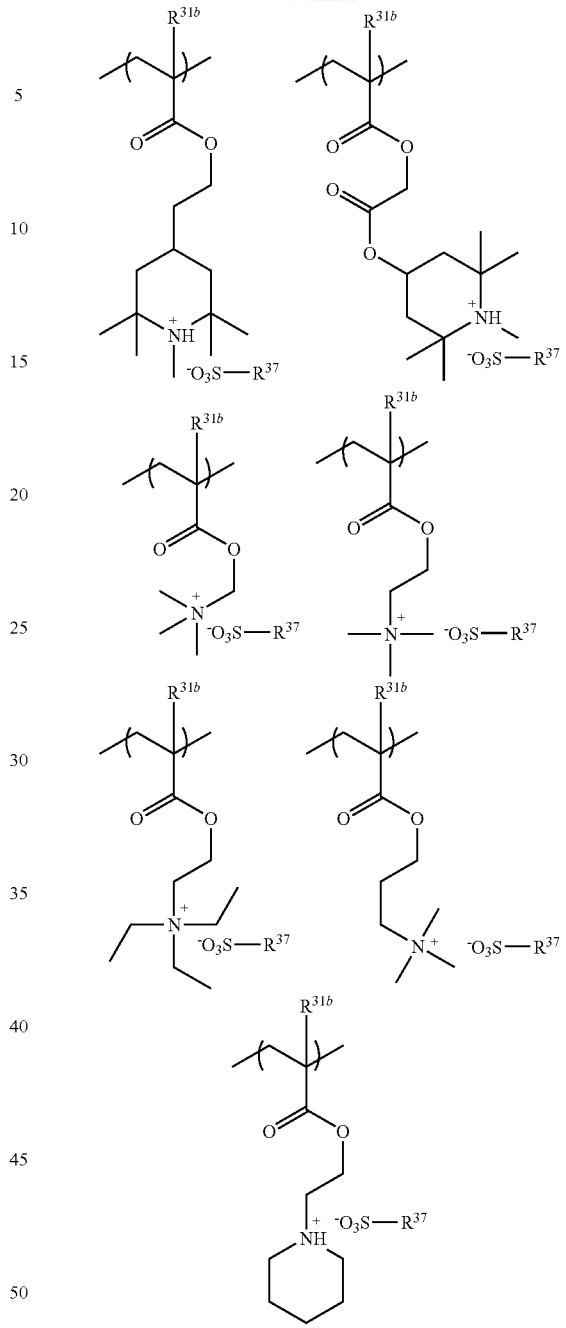

Herein $R^{31b}$ and $R^{37}$ are as defined above.

Examples of the sulfonic acid salt used in the recurring units of formula (10) include fluoroalkylsulfonates such as triflate, 1,1,1-trifluoroethanesulfonate and nonafluorobutanesulfonate; arylsulfonates such as tosylate, benzenesulfonate, 4-fluorobenzenesulfonate, 1,2,3,4,5-pentafluorobenzenesulfonate, xylenesulfonate, mesitylenesulfonate, p-t-butylbenzenesulfonate, naphthalenesulfonate, anthracenesulfonate, and pyrenesulfonate; and alkylsulfonates such as mesylate, butanesulfonate, octanesulfonate, camphorsulfonate, adamantanesulfonate, norbornanesulfonate, cyclohexylsulfonate, cyclopentanesulfonate, cyclobutanesulfonate, cyclopropanesulfonate, and dodecylbenzenesulfonate.

Illustrative, non-limiting examples of the recurring units of formula (11) are given below.

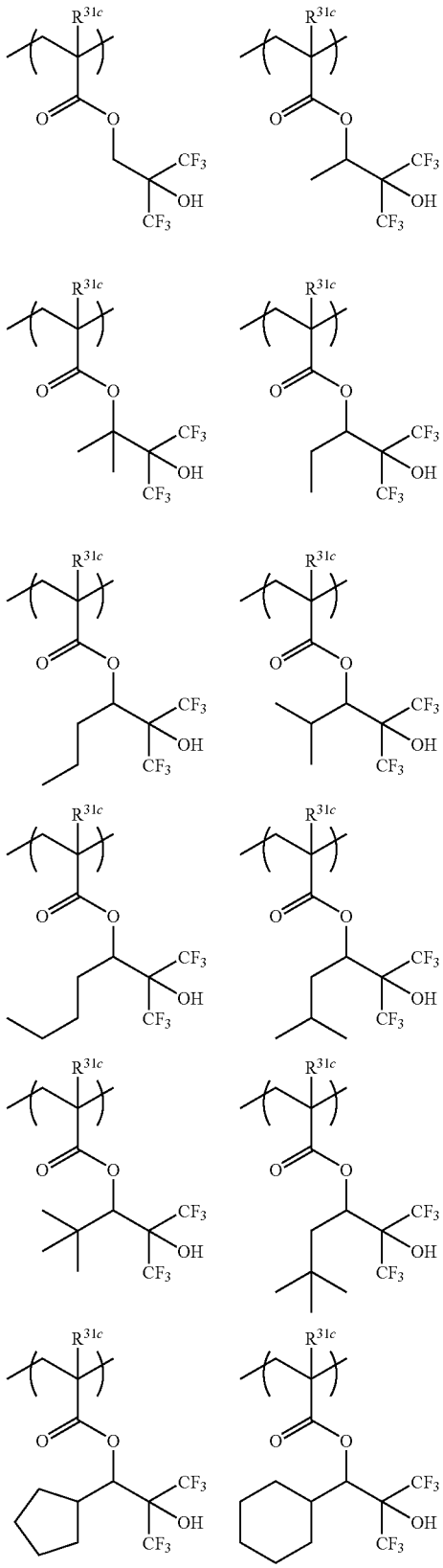

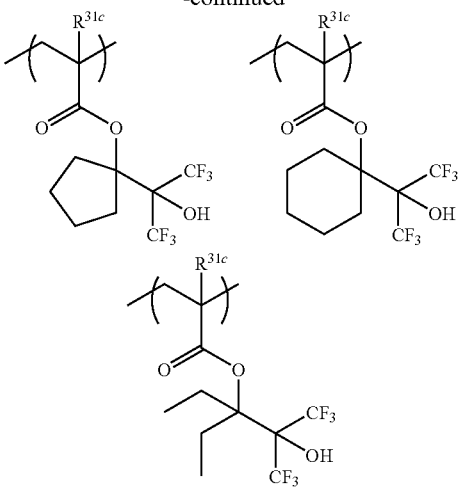

Herein $R^{31c}$ is as defined above.

Although the polymer comprising recurring units of formulae (9) to (11) exerts satisfactory performance even when it has only a combination of recurring units of formulae (9) to (11), recurring units of one or more types selected from formulae (12a) to (12e), (13a) to (13e), (14a) to (14c), and (15a) to (15c) may be further incorporated therein for the purposes of imparting further water repellency and water sliding property, and controlling alkaline solubility and developer affinity.

Polymer Synthesis

For convenience of description, the polymer comprising recurring units of formulae (5) to (7) and optionally recurring units of formulae (8a) to (8f) is referred to as polymer P1, and the second or blending polymer comprising recurring units of formulae (9) to (11) is referred to as polymer P2.

The polymers P1 and P2 used herein may be synthesized by general polymerization processes including radical polymerizataion using initiators such as 2,2'-azobisisobutyronitrile (AIBN), and ionic (or anionic) polymerization using alkyllithium or the like. The polymerization may be carried out by a standard technique. Preferably the polymers are prepared by radical polymerization while the polymerization conditions may be determined in accordance with the type and amount of initiator, temperature, pressure, concentration, solvent, additives, and the like.

Examples of the radical polymerization initiator used herein include azo compounds such as 2,2'-azobisisobutyronitrile (AIBN), 2,2'-azobis(4-methoxy-2,4-dimethylvaleronitrile), 2,2'-azobis(2,4-dimethylvaleronitrile), 2,2'-azobis(2,4,4-trimethylpentane), and dimethyl 2,2'-azobis(isobutyrate); peroxides such as tert-butylperoxypivalate, lauroyl peroxide, benzoyl peroxide, and tert-butylperoxylaurate; water-soluble polymerization initiators such as potassium persulfate; and redox initiators comprising a peroxide (e.g., potassium persulfate or hydrogen peroxide) combined with a reducing agent (e.g., sodium sulfite). Although the amount of polymerization initiator used may vary with its type and other polymerization conditions, it is generally used in an amount of 0.001 to 10 mol %, and preferably 0.01 to 6 mol % based on the total moles of monomers to be polymerized.

During the synthesis of polymer P1 or P2, any known chain transfer agent such as dodecyl mercaptan or 2-mercaptoethanol may be added for molecular weight control purpose. The amount of chain transfer agent added is preferably 0.01 to 10 mol % based on the total moles of monomers to be polymerized.

Polymer P1 may be synthesized by combining suitable monomers selected from polymerizable monomers corresponding to recurring units of formulae (5) to (7), (8a) to (8f), (12a) to (12e), (13a) to (13e), (14a) to (14c), and (15a) to (15c), adding an initiator and chain transfer agent to the monomer mixture, and effecting polymerization. Similarly, polymer P2 may be synthesized by combining suitable monomers selected from polymerizable monomers corresponding to recurring units of formulae (9) to (11), adding an initiator and chain transfer agent to the monomer mixture, and effecting polymerization.

In polymer P1 wherein U11 stands for a total molar number of a monomer or monomers corresponding to units of formulae (5) to (7), U12 stands for a total molar number of a monomer or monomers corresponding to units of formulae (8a) to (8f), and U13 stands for a total molar number of a monomer or monomers corresponding to units of formulae (12a) to (12e), (13a) to (13e), (14a) to (14c), and (15a) to (15c), with the proviso that U11+U124-U13=U1, values of U11, U12, and U13 are preferably determined so as to meet:

0<U11/U1<1, more preferably 0.1≦U11/U1≦0.7, even more preferably 0.2≦U11/U1≦0.6, 0≦U12/U1<1, more preferably 0.3≦U12/U1≦0.9, even more preferably 0.4≦U12/U1≦0.8, and 0≦U13/U1<1, more preferably 0≦U13/U1≦0.5, even more preferably 0≦U13/U1≦0.3, with the proviso that U1≦100 mol %.

In polymer P2 wherein U21 stands for a total molar number of a monomer(s) corresponding to units of formula (9), U22 stands for a total molar number of a monomer(s) corresponding to units of formula (10), U23 stands for a total molar number of a monomer(s) corresponding to units of formula (11), and U24 stands for a total molar number of a monomer(s) corresponding to units of formulae (12a) to (12e), (13a) to (13e), (14a) to (14c), and (15a) to (15c), with the proviso that U21+U22+U23+U24=U2, values of U21, U22, U23, and U24 are preferably determined so as to meet:

0≦U21/U2<1, more preferably 0≦U21/U2≦0.5, even more preferably 0≦U21/U2≦0.3,

0≦U22/U2<1, more preferably 0≦U22/U2≦0.5, even more preferably 0≦U22/U2≦0.3,

0<U23/U2<1, more preferably 0.5≦U23/U2<1, even more preferably 0.7≦U23/U2<1, and 0≦U24/U2<1, more preferably 0≦U24/U2<0.5, even more preferably 0≦U24/U2<0.3, with the proviso that U2≦100 mol %.

In conducting polymerization, a solvent may be used if necessary. Any solvent may be used as long as it does not interfere with the desired polymerization reaction. Typical solvents used herein include esters such as ethyl acetate, n-butyl acetate, and γ-butyrolactone; ketones such as acetone, methyl ethyl ketone, and methyl isobutyl ketone; aliphatic or aromatic hydrocarbons such as toluene, xylene and cyclohexane; alcohols such as isopropyl alcohol and ethylene glycol monomethyl ether; and ether solvents such as diethyl ether, dioxane, and tetrahydrofuran, which may be used alone or in admixture. Although the amount of solvent used may vary with the desired degree of polymerization (or molecular weight), the amount of initiator added, and other polymerization conditions such as polymerization temperature, it is generally used in such an amount as to provide a concentration of 0.1 to 95% by weight, preferably 5 to 90% by weight of monomers to be polymerized.

Although the temperature of the polymerization reaction may vary with the identity of polymerization initiator or the boiling point of solvent, it is preferably in the range of 20 to 200° C., and more preferably 50 to 140° C. Any desired reactor or vessel may be used for the polymerization reaction.

From the solution or dispersion of the polymer thus synthesized, the organic solvent or water serving as the reaction medium is removed by any well-known techniques. Suitable techniques include, for example, re-precipitation followed by filtration, and heat distillation under vacuum.

Desirably polymers P1 and P2 have a weight average molecular weight (Mw) of 1,000 to 500,000, and especially 2,000 to 30,000, as determined by gel permeation chromatography (GPC) using polystyrene standards. This is because a polymer with too low a Mw may be miscible with the resist material or more dissolvable in water whereas too high a Mw may interfere with film formation after spin coating and lead to a decline of alkali solubility.

In polymers P1 and P2, $R^4$ in formula (5), $R^{14}$ in formulae (8a), (8b), and (8e), and $R^{19}$ in formula (12c) and (13c) may be introduced by post-protection reaction. Specifically, a polymer may be synthesized by polymerizing a monomer wherein $R^4$, $R^{14}$ and $R^{19}$ are hydrogen to synthesize an intermediate polymer, then effecting post-protection reaction to substitute $R^4$, $R^{14}$ and $R^{19}$ (as defined above) for some or all hydroxyl groups in the intermediate polymer.

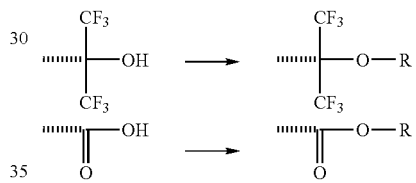

The desired (post-protected) polymer is obtainable through post-protection reaction by reacting the intermediate polymer with a base in an amount of 1 to 2 equivalents relative to the desired degree of substitution of hydroxyl groups, and then with R—X (wherein R is $R^4$, $R^{14}$ and $R^{19}$ as mentioned above and X is chlorine, bromine or iodine) in an amount of 1 to 2 equivalents relative to the base.

The post-protection reaction may be effected in a solvent, which is selected from hydrocarbons such as benzene and toluene, and ethers such as dibutyl ether, diethylene glycol diethyl ether, diethylene glycol dimethyl ether, tetrahydrofuran and 1,4-dioxane, alone or in admixture. Suitable bases used herein include, but are not limited to, sodium hydride, n-butyllithium, lithium diisopropylamide, triethylamine, and pyridine.

In polymer P2, the ammonium salt in recurring units of formula (9) may be obtained from neutralization reaction of a (meth)acrylate having a sulfo pendant group with a corresponding amine or ion exchange reaction thereof with an ammonium salt having the following general formula.

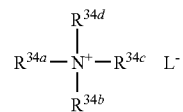

Herein $R^{34a}$ to $R^{34d}$ are as defined above, $L^-$ is $OH^-$, $Cl^-$, $Br^-$, $I^-$, $R^{39}CO_2^-$, or $NO_3^-$, and $R^{39}$ is hydrogen or a monovalent organic group.

In polymer P2, recurring units of formula (9) may be introduced by effecting neutralization reaction or ion exchange reaction at the monomer stage or after polymer synthesis. In the latter case, if the amount of amine added is small, an amine salt is not uniformly formed within polymer units which may cause local bridge defects upon pattern formation. To avoid such inconvenience, it is preferred that neutralization or ion exchange reaction be carried out in a monomer form, and this be followed by polymerization using the resulting monomer having a sulfonic acid amine salt uniformly distributed.

In polymer P2 wherein recurring units of formula (10) are introduced, those units containing a tertiary or lower ammonium salt may be obtained from neutralization reaction of a (meth)acrylate having an amino pendant group with a corresponding sulfonic acid. Those units containing a quaternary ammonium salt may be obtained from ion exchange reaction as described above. As in the case of recurring units of formula (9), neutralization reaction or ion exchange reaction may be effected either at the monomer stage or after polymer synthesis.

With respect to the recurring units of formula (9), a degree of neutralization between sulfo group and amine compound in an overall polymer may be such that with a less amine equivalent, sulfonic acid residues are present or inversely, amine is in excess. Where sulfonic acid residues are available, the protective coating, when combined with a photoresist, is effective for preventing bridges between features of a resist pattern after development. On the other hand, where an excess of amine is available, the protective coating is effective for improving the rectangularity of a resist pattern. With these considerations, the amounts of sulfo group and amine may be adjusted as appropriate while monitoring a resist pattern after development. The same applies to the recurring units of formula (10).

Protective Coating Composition

In one embodiment, the invention provides a resist protective coating composition comprising the polymer P1 defined above. Polymer P1 comprises recurring units of formula (5), (6) or (7) which contain a fluorinated hemiacetal structure having a protected hydroxyl group. By a choice of resin structure, it is possible to tailor any of properties including water repellency, water sliding property, lipophilicity, acid lability, hydrolyzability, and alkaline solubility.

Since polymer P2 contains a hydrophilic sulfonic acid amine salt in recurring units, it tends to segregate on the resist side after spin coating. As a result, the resist surface after development becomes hydrophilic, inhibiting blob defects. If a polymer having only sulfo groups is used as a protective coating material, part of the quencher in the resist film migrates to the protective coating layer. In case quencher migration occurs, the quencher concentration at the outermost surface of the resist film lowers, and the resist pattern after development may be concomitantly thinned and as a result, weakened in etch resistance. In contrast, a protective coating layer of polymer P2 in which a sulfonic acid amine salt is present prohibits quencher migration as mentioned above and ensures to form a rectangular resist pattern.

When a blend of polymers P1 and P2 is used, layer separation occurs during spin coating such that polymer featuring water repellency and water sliding property segregates in a protective coating upper layer and polymer P2 featuring hydrophilicity segregates in a protective coating lower layer on top of the resist film. This results in a protective coating having improved water repellency and water sliding property on the resist surface and effective in inhibiting blob defects.

While polymers P1 and P2 may be mixed at any desired ratio, polymer P1 is typically present in a weight ratio of 5 to 95%, preferably 20 to 93%, and more preferably 30 to 90% based on the entire resin.

Typically a blend of polymers P1 and P2 is used as a base resin in a protective coating composition while another polymer may be mixed therewith for the purpose of altering some properties of a protective coating such as dynamic physical properties, thermal properties, alkaline solubility, water repellency, and water sliding property. The other polymer which is mixed is not particularly limited, and any of well-known polymers useful in the protective topcoat application may be chosen and mixed in any desired ratio.

Most often, the polymers are dissolved in a suitable solvent to form a solution which is ready for use as the resist protective coating composition. For film formation by spin coating technique, the solvent is preferably used in such amounts to provide a concentration of 0.1 to 20% by weight, more preferably 0.5 to 10% by weight of the entire resin.

Although the solvent used herein is not particularly limited, those solvents in which resist layers are not dissolvable are preferred. Suitable solvents in which resist layers are not dissolvable include nonpolar solvents, for example, higher alcohols of at least 4 carbon atoms, toluene, xylene, anisole, hexane, cyclohexane, decane, and ethers. Of these, higher alcohols of at least 4 carbon atoms and ether compounds of 8 to 12 carbon atoms are most desirable. Examples of suitable solvents include, but are not limited to, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2,2-diethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, and cyclohexanol as well as diisopropyl ether, diisobutyl ether, diisopentyl ether, di-n-pentyl ether, methylcyclopentyl ether, methylcyclohexyl ether, di-n-butyl ether, di-sec-butyl ether, diisopentyl ether, di-sec-pentyl ether, di-t-amyl ether, and di-n-hexyl ether. These solvents may be used alone or in admixture.

Fluorinated solvents are also preferred because resist layers are not dissolvable therein. Examples include, but are not limited to, 2-fluoroanisole, 3-fluoroanisole, 4-fluoroanisole, 2,3-difluoroanisole, 2,4-difluoroanisole, 2,5-difluoroanisole, 5,8-difluoro-1,4-benzodioxane, 2,3-difluorobenzyl alcohol, 1,3-difluoro-2-propanol, 2',4'-difluoropropiophenone, 2,4-difluorotoluene, trifluoroacetaldehyde ethyl hemiacetal, trifluoroacetamide, trifluoroethanol, 2,2,2-trifluoroethyl butyrate, ethyl heptafluorobutyrate, ethyl heptafluorobutylacetate, ethyl hexafluoroglutarylmethyl, ethyl 3-hydroxy-4,4,4-trifluorobutyrate, ethyl 2-methyl-4,4,4-trifluoroacetoacetate, ethyl pentafluorobenzoate, ethyl pentafluoropropionate, ethyl pentafluoropropynylacetate, ethyl perfluorooctanoate, ethyl 4,4,4-trifluoroacetoacetate, ethyl 4,4,4-trifluorobutyrate, ethyl 4,4,4-trifluorocrotonate, ethyl trifluorosulfonate, ethyl 3-(trifluoromethyl)butyrate, ethyl trifluoropyruvate, S-ethyl trifluoroacetate, fluorocyclohexane, 2,2,3,3,4,4,4-heptafluoro-1-butanol, 1,1,1,2,2,3,3-heptafluoro-7,7-dimethyl-4,6-octanedione, 1,1,1,3,5,5,5-heptafluoropentane-2,4-dione, 3,3,4,4,5,5,5-heptafluoro-2-pentanol, 3,3,4,4,5,5,5-heptafluoro-2-pentanone, isopropyl 4,4,4-trifluoroacetoacetate, methyl perfluorodecanoate, methyl perfluoro(2-methyl-3-oxahexanoate), methyl perfluorononanoate, methyl perfluorooctanoate, methyl 2,3,3,3- tetrafluoropropionate, methyl trifluoroacetoacetate, 1,1,1,2,2,6,6,6-octafluoro-2,4-hexanedione, 2,2,3,3,4,4,5,5-octafluoro-1-pentanol, 1H,1H,2H,2H-perfluoro-1-decanol, perfluoro(2,5-dimethyl-3,6-dioxane anionic) acid methyl ester, 2H-perfluoro-5-methyl-3,6-dioxanonane, 1H,1H,2H,3H,3H-perfluorononane-1,2-diol, 1H,1H,9H-perfluoro-1-nonanol, 1H,1H-perfluorooctanol, 1H,1H,2H,2H-perfluorooctanol, 2H-perfluoro-5,8,11,14-tetramethyl-3,6,9,12,15-pentaoxa-octadecane, perfluorotributylamine, perfluorotrihexylamine, methyl perfluoro-2,5,8-trimethyl-3,6,9-trioxadodecanoate, perfluorotripentylamine, perfluorotripropylamine, 1H,1H,2H,3H,3H-perfluoroundecane-1,2-diol, trifluorobutanol, 1,1,1-trifluoro-5-methyl-2,4-hexanedione, 1,1,1-trifluoro-2-propanol, 3,3,3-trifluoro-1-propanol, 1,1,1-trifluoro-2-propyl acetate, perfluorobutyltetrahydrofuran, perfluorodecalin, perfluoro(1,2-dimethylcyclohexane), perfluoro(1,3-dimethylcyclohexane), propylene glycol trifluoromethyl ether acetate, propylene glycol methyl ether trifluoromethyl acetate, butyl trifluoromethylacetate, methyl 3-trifluoromethoxypropionate, perfluorocyclohexanone, propylene glycol trifluoromethyl ether, butyl trifluoroacetate, 1,1,1-trifluoro-5,5-dimethyl-2,4-hexanedione, 1,1,1,3,3,3-hexafluoro-2-propanol, 1,1,1,3,3,3-hexafluoro-2-methyl-2-propanol, 2,2,3,4,4,4-hexafluoro-1-butanol, 2-trifluoromethyl-2-propanol, 2,2,3,3-tetrafluoro-1-propanol, 3,3,3-trifluoro-1-propanol, and 4,4,4-trifluoro-1-butanol, which may be used alone or in admixture.

In the resist protective coating composition, a basic compound may be used for the purpose of performance amelioration such as pattern profile correction. For example, polymer P1 has acidic hydroxyl groups in recurring units with a possibility that part of the quencher in the resist film migrates to the protective coating layer. As discussed above, in case quencher migration occurs, the quencher concentration at the outermost surface of the resist film lowers, and the resist pattern after development is concomitantly thinned. A basic compound is previously added to the protective coating composition to avoid such quencher migration, preventing any degradation of pattern profile.

Preferred basic compounds are nitrogen-containing organic compounds which may be used alone or in admixture. Suitable nitrogen-containing organic compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, amide, imide and carbamate derivatives. Illustrative examples are described in JP-A 2008-111103, paragraphs [0149] to [0163]. The basic compound is preferably used in an amount of 0.001 to 2 parts, more preferably 0.01 to 1 part by weight per 100 parts by weight of the base resin.

Pattern Forming Process

The pattern forming process in a preferred embodiment involves at least the steps of forming a photoresist film on a substrate, forming a protective coating on the photoresist film from the resist protective coating composition of the invention, exposing the layer structure to light, and development with a developer.

First a photoresist material is applied onto a substrate and prebaked to form a photoresist film thereon. The protective coating solution is then applied onto the photoresist film by spin coating, and prebaked on a hot plate at 50 to 150° C. for 1 to 10 minutes, preferably at 70 to 140° C. for 1 to 5 minutes, to form a protective coating. The protective coating preferably has a thickness of 10 to 500 nm.

If the protective coating solution is spin coated onto the surface of the resist film which has been wetted with a suitable solvent, the amount of the protective coating solution dispensed can be reduced. The means of wetting the resist surface include spin coating and vapor priming, with the spin coating technique being often employed. The solvent used for wetting may be selected from the aforementioned higher alcohols, ethers, and fluorinated solvents in which the resist is not dissolved.

A mask having the desired pattern is then placed over the photoresist film, and the film exposed through the mask to an electron beam or to high-energy radiation such as deep-UV, excimer laser or x-ray in a dose of 1 to 200 mJ/cm$^2$, and preferably 10 to 100 mJ/cm$^2$. Light exposure is preferably by immersion lithography of providing a liquid between the protective coating and the projection lens, though not limited thereto. The exposure may be either dry exposure in air or nitrogen atmosphere or vacuum exposure as in the case of EB or EUV lithography. In the immersion lithography, a light source producing emission having a wavelength in the range of 180 to 250 nm is preferred, and water is preferably used as the liquid between the protective coating and the lens.

In the immersion lithography, whether or not the wafer edge and rear side are cleaned and the cleaning technique are important in preventing flowing of water to the wafer rear side and leaching from the substrate. For example, after spin coating, the resist protective coating is baked at a temperature of 40 to 130° C. for 10 to 300 seconds for evaporating off the solvent. In the case of resist layer formation and dry lithography, edge cleaning is performed during the spin coating. In the case of immersion lithography, however, such edge cleaning is undesirable because water may be left on the hydrophilic substrate surface at the edge. It is then recommended to omit edge cleaning during the spin coating of the resist protective coating.

Exposure is followed by post-exposure bake (PEB) on a hot plate at 60 to 150° C. for 1 to 5 minutes, preferably at 80 to 140° C. for 1 to 3 minutes. Sometimes water is left on the protective coating prior to PEB. If PEB is performed in the presence of residual water, water can penetrate through the protective coating to suck up the acid in the resist, impeding pattern formation. Such inconvenience must be avoided by fully removing the water on the protective coating prior to PEB. The water on the protective coating should be dried or recovered by suitable means, for example, spin drying, purging of the protective coating surface with dry air or nitrogen, or optimizing the water recovery nozzle configuration on a stage or water recovery process. Additionally, the design and utilization of a material having high water repellency and water sliding property, typically the protective coating composition of the invention, offers the advantage of efficient water removal.

After PEB, development is carried out using as the developer an aqueous alkaline solution, such as a 0.1 to 5 wt %, preferably 2 to 3 wt %, aqueous solution of tetramethylammonium hydroxide (TMAH), this being done by a conventional method such as dip, puddle, or spray development for a period of 10 to 300 seconds, and preferably 0.5 to 2 minutes. A typical developer is a 2.38 wt % TMAH aqueous solution. These steps result in the formation of the desired pattern on the substrate. Where the resist protective coating composition is used, the protective coating composition itself exhibits alkaline solubility so that the protective coating can be stripped at the same time as development.

Where a pattern is formed using the protective coating composition, the resist material of which the underlying resist layer is made is not particularly limited. The resist type may be either positive or negative working and also either a monolayer resist of conventional hydrocarbon or a bilayer (or multilayer) resist containing silicon atoms or the like.

For KrF lithography resist materials, the preferred base resins are polyhydroxystyrene or polyhydroxystyrene-(meth) acrylate copolymers in which some or all hydrogen atoms of hydroxyl or carboxyl groups are replaced by acid labile groups.

For ArF lithography resist materials, the preferred base resin has an aromatic-free structure. Illustrative polymers include (meth)acrylic derivative copolymers, norbornene derivative/maleic anhydride alternating copolymers, norbornene derivative/maleic anhydride/(meth)acrylic derivative copolymers, tetracyclododecene derivative/maleic anhydride alternating copolymers, tetracyclododecene derivative/maleic anhydride/(meth)acrylic derivative copolymers, norbornene derivative/maleimide alternating copolymers, norbornene derivative/maleimide/(meth)acrylic derivative copolymers, tetracyclododecene derivative/maleimide derivative alternating copolymers, tetracyclododecene derivative/maleimide derivative/(meth)acrylic derivative copolymers, polynorbornene derivatives, and ring-opening metathesis polymerization (ROMP) polymers, and a combination of any.

A polymer comprising recurring units containing aromatic ring could not be used initially as the ArF lithography resist since it has absorption at wavelength 193 nm. As the resist film becomes thinner, the influence of absorption is mitigated, indicating the potential of such a polymer being applied to the ArF lithography. Also, since the reflection of oblique incident light from the substrate increases when a projection lens has a NA in excess of 1, it is proposed to positively utilize the absorptive aromatic ring for suppressing reflection from the substrate. Polymers useful in this case include copolymers of hydroxyvinylnaphthalene, methacrylates containing naphthalene and naphthol structures on side chains, fluorinated hydroxystyrene, fluoroalkylhydroxystyrene, fluorinated styrene, fluoroalkylstyrene, hexafluoroisopropanolstyrene, and hexafluoroisopropanolindene.

A further aspect of the invention provides a pattern forming process involving the steps of forming a photoresist layer on a mask blank, forming a protective coating on the photoresist layer from the resist protective coating composition of the invention, effecting electron beam exposure in vacuum, and development.

Where the polymer is used as a resist protective coating for use with mask blanks, a photoresist is coated on a mask blank substrate of $SiO_2$, Cr, CrO, CrN, MoSi or the like before the protective coating composition is applied to form a protective coating on the resist film. By further forming a SOG film and an organic undercoat film between the photoresist and the blank substrate, there is provided a three-layer structure which is also acceptable herein. Once the protective coating film is formed, the structure is exposed to EB in vacuum using an EB image-writing system. The exposure is followed by post-exposure baking (PEB) and development in an alkaline developer for 10 to 300 seconds.

For the resit material used with mask blanks, novolac resins and hydroxystyrene are often used as the base resin. Those resins in which alkali-soluble hydroxyl groups are substituted by acid labile groups are used for positive resists while these resins in combination with crosslinking agents are used for negative resists. Base polymers which can be used herein include copolymers of hydroxystyrene with one or more of (meth)acrylic derivatives, styrene, vinyl naphthalene, vinyl anthracene, vinyl pyrene, hydroxyvinyl naphthalene, hydroxyvinyl anthracene, indene, hydroxyindene, acenaphthylene, norbornadiene, coumarone, and chromone.

Resist Composition

In a further aspect, the invention provides a resist composition comprising (A) a polymer P1 comprising recurring units of formula (5), (6) or (7), (B) a base polymer having a structure derived from lactone ring, hydroxyl group and/or maleic anhydride, the base polymer becoming soluble in alkaline developer under the action of acid, (C) a compound capable of generating an acid upon exposure to high-energy radiation, and (D) an organic solvent.

Polymer(s) P1 as component (A) is added to the resist composition preferably in a total amount of 0.1 to 50 parts, more preferably 0.5 to 10 parts by weight per 100 parts by weight of the base resin (B). At least 0.1 phr of polymer P1 is effective in improving the receding contact angle with water of photoresist film surface, whereas up to 50 phr of polymer P1 forms a photoresist film having a low dissolution rate in alkaline developer and capable of maintaining the height of a fine pattern formed therein.

Since polymer P1 comprises recurring units of formula (5), (6) or (7) which contain a fluorinated hemiacetal structure having a protected hydroxyl group, a choice of resin structure makes it possible to tailor any of properties including water repellency, water sliding property, lipophilicity, acid lability, hydrolyzability, and alkaline solubility.

When polymer P1 is used in admixture with base resin (B) to form a resist film, layer separation occurs during spin coating such that polymer P1 segregates in a resist film upper layer. The resulting resist film displays improved water repellency and water sliding property on its surface and prevents water-soluble components from being leached out of the resist material.

The resist composition contains (B) a base resin or polymer which has a structure derived from lactone ring and/or hydroxyl group and/or maleic anhydride and becomes soluble in alkaline developer under the action of acid. The polymers which can serve as the base resin (B) include (meth)acrylates, (α-trifluoromethyl)acrylate/maleic anhydride copolymers, cycloolefin/maleic anhydride alternating copolymers, polynorbornene, cycloolefin ring-opening metathesis polymerization (ROMP) polymers, hydrogenated cycloolefin ROMP polymers, examples of which are described in JP-A 2008-111103, paragraphs [0072] to [0120]. The polymer serving as base resin (B) is not limited to one type and a mixture of two or more polymers may be added. The use of plural polymers allows for easy adjustment of resist properties.

In order that the resist composition function as a chemically amplified resist composition, (C) a compound capable of generating an acid upon exposure to high-energy radiation, referred to as "photoacid generator" or PAG, may be compounded. The photoacid generator may be any compound capable of generating an acid upon exposure of high-energy radiation. Suitable photoacid generators include sulfonium salts, iodonium salts, sulfonyldiazomethane, N-sulfonyloxyimide, and oxime-O-sulfonate acid generators. Exemplary acid generators are described in JP-A 2008-111103, paragraphs [0123] to [0138].

The preferred PAGs are those compounds of the general formula (C)-1.

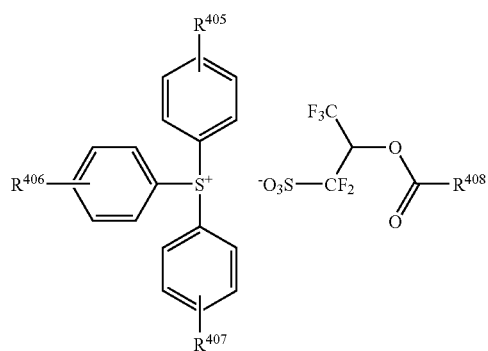

(C)-1

Herein $R^{405}$, $R^{406}$, and $R^{407}$ are each independently hydrogen or a straight, branched or cyclic, monovalent $C_1$-$C_{20}$ hydrocarbon group which may contain a heteroatom, typically an alkyl or alkoxy group. $R^{408}$ is a straight, branched or cyclic, monovalent $C_7$-$C_{30}$ hydrocarbon group which may contain a heteroatom.

Examples of the hydrocarbon groups optionally containing a heteroatom, represented by $R^{405}$, $R^{406}$, and $R^{407}$, include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional group such as —OH, —NH$_2$, —CHO, or —CO$_2$H. Examples of the straight, branched or cyclic, monovalent $C_7$-$C_{30}$ hydrocarbon groups optionally containing a heteroatom, represented by $R^{408}$, are shown below, but not limited thereto.

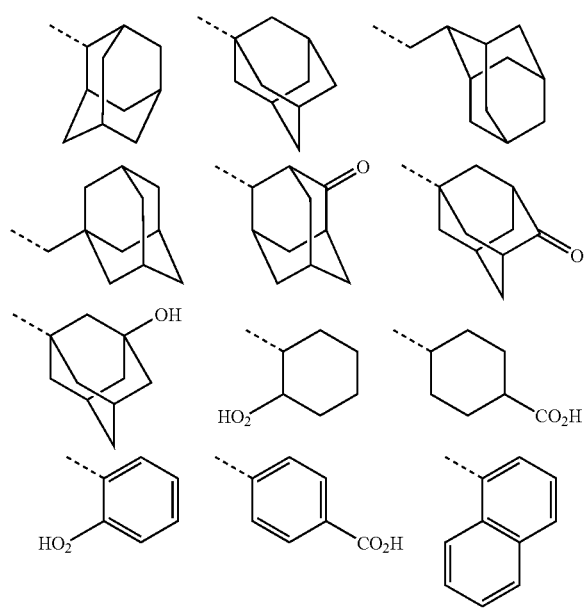

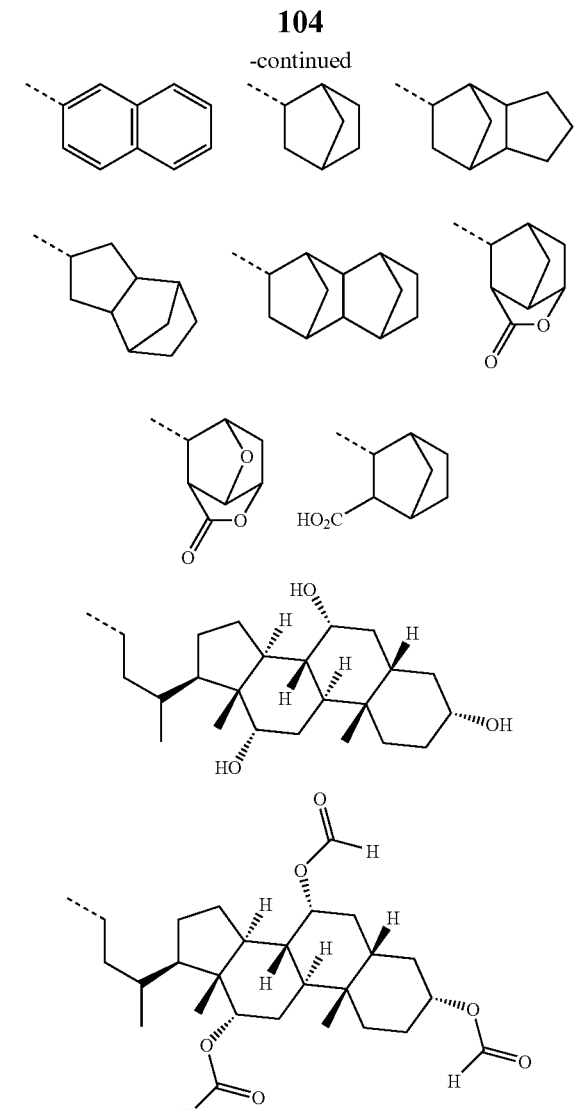

Illustrative examples of acid generators (C)-1 are shown below, but not limited thereto.

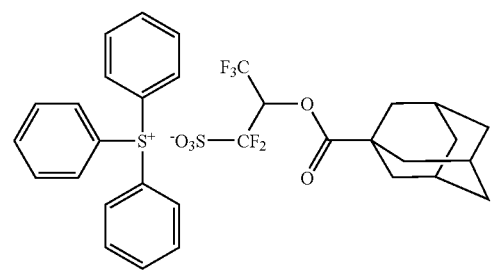

105
-continued
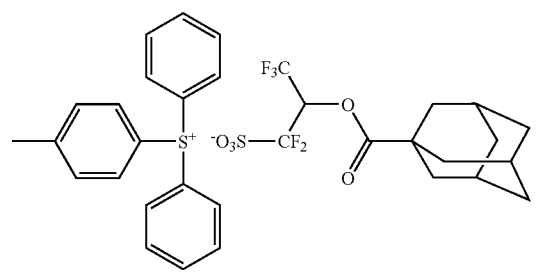
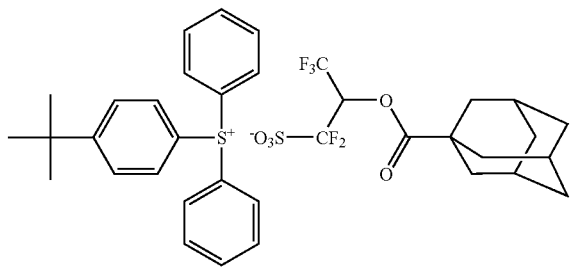
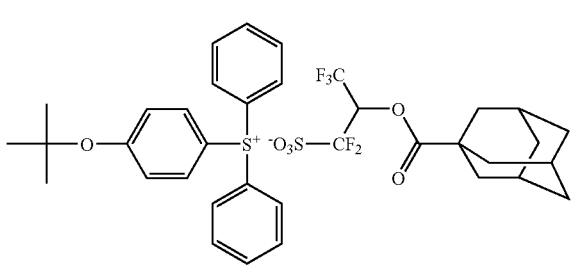
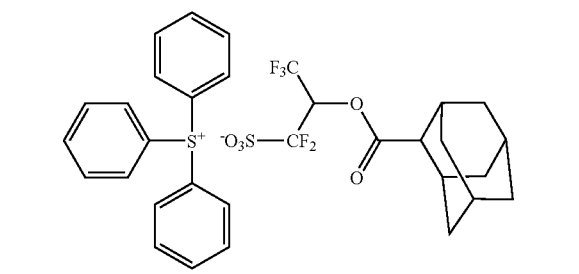
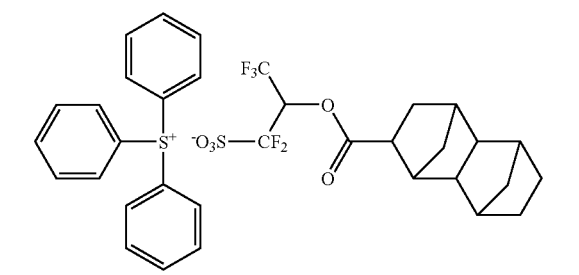
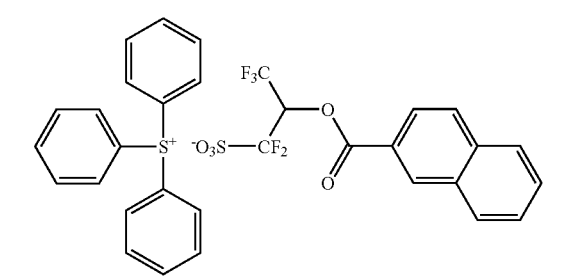
106
-continued
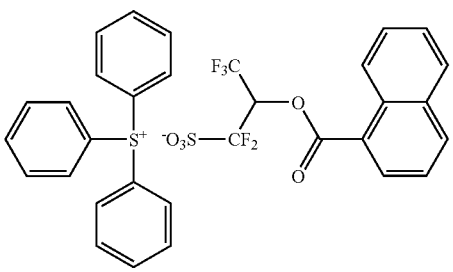
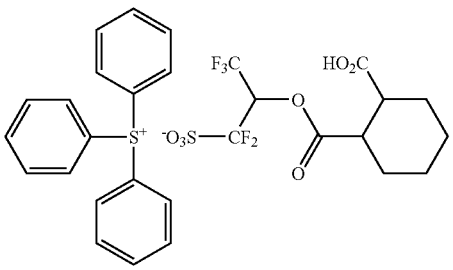
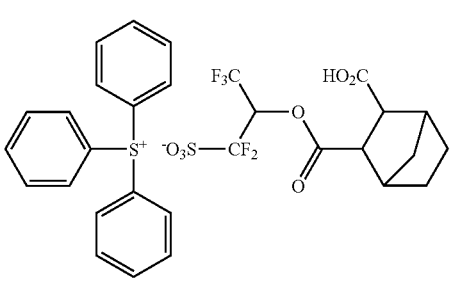
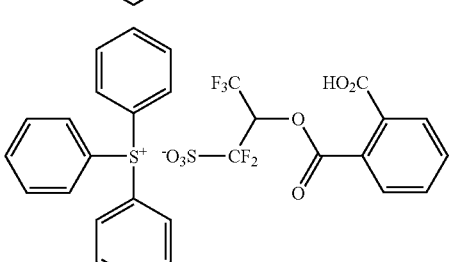
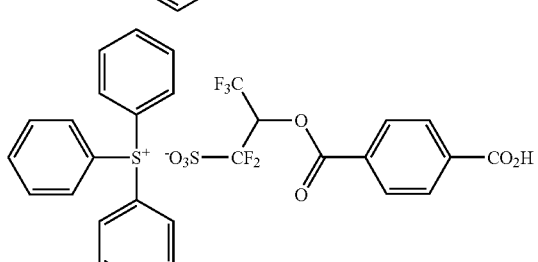
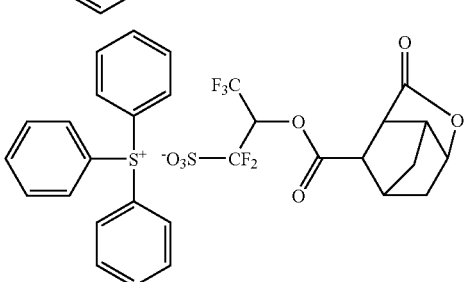

-continued

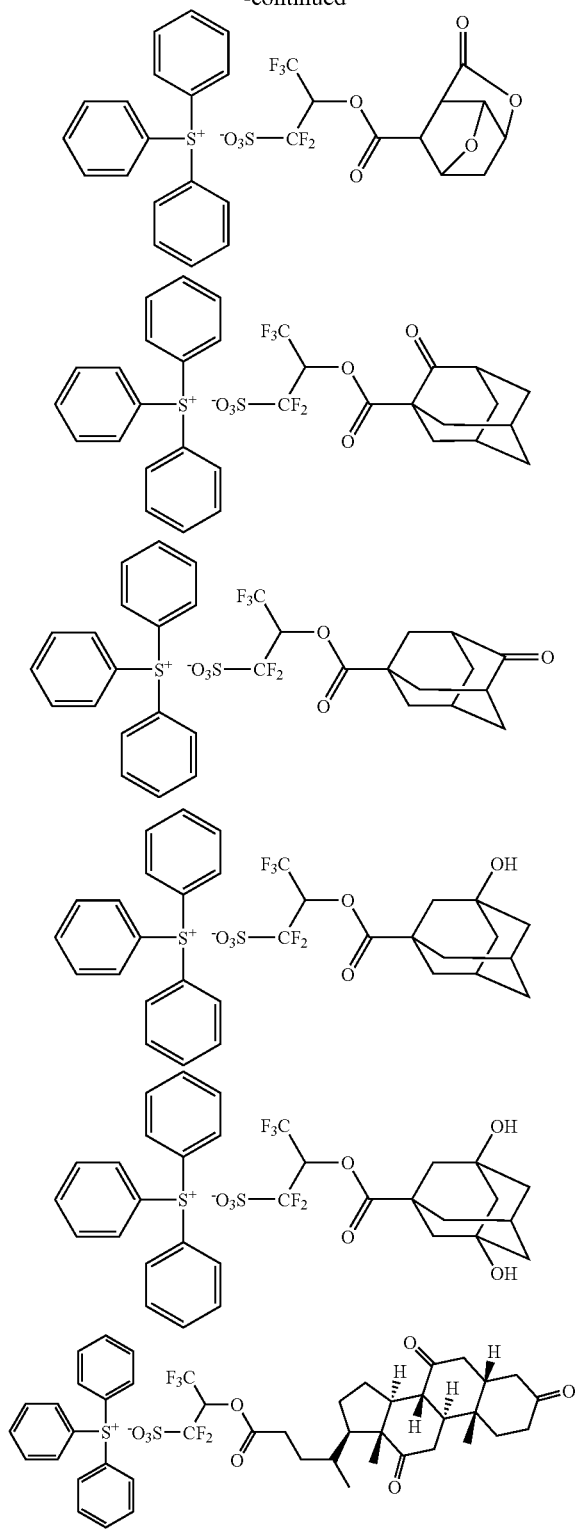

In the resist composition, specifically chemically amplified resist composition, PAG may be added in any desired amount as long as the objects of the invention are not compromised. An appropriate amount of PAG is 0.1 to 10 parts, and more preferably 0.1 to 5 parts by weight per 100 parts by weight of the base resin in the composition. Too large an amount of PAG may give rise to problems of degraded resolution and foreign matter upon development and resist film peeling. The PAG may be used alone or in admixture of two or more. The transmittance of the resist film can be controlled by using a PAG having a low transmittance at the exposure wavelength and adjusting the amount of the PAG added.

It is noted that an acid diffusion controlling function may be provided when two or more PAGs are used in admixture provided that one PAG is an onium salt capable of generating a weak acid. Specifically, in a system using a mixture of a PAG capable of generating a strong acid (e.g., fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the PAG capable of generating a strong acid is also an onium salt, an exchange from the strong acid (generated upon exposure to high-energy radiation) to a weak acid as above can take place, but it never happens that the weak acid (generated upon exposure to high-energy radiation) collides with the unreacted onium salt capable of generating a strong acid to induce a salt exchange. This is because of a likelihood of an onium cation forming an ion pair with a stronger acid anion.

An appropriate amount of PAG added is 0.1 to 20 parts, and more preferably 0.1 to 10 parts by weight per 100 parts by weight of the base resin (B) in the composition. As long as PAG is up to 20 phr, the resulting photoresist film has a fully high transmittance and a minimal likelihood of degraded resolution. The PAG may be used alone or in admixture of two or more. The transmittance of the resist film can be controlled by using a PAG having a low transmittance at the exposure wavelength and adjusting the amount of the PAG added.

The resist composition may further comprise one or more of (D) an organic solvent, (E) a basic compound, (F) a dissolution regulator, (G) a surfactant, and (H) an acetylene alcohol derivative.

The organic solvent (D) used herein may be any organic solvent in which polymer P1, the base resin, PAG, and other components are soluble. Exemplary solvents are described in JP-A 2008-111103, paragraph [0144]. The organic solvents may be used alone or in combinations of two or more thereof. An appropriate amount of the organic solvent used is 200 to 3,000 parts, especially 400 to 2,500 parts by weight per 100 parts by weight of the base resin (B). It is recommended to use diethylene glycol dimethyl ether, 1-ethoxy-2-propanol, PGMEA, and mixtures thereof because the acid generator is most soluble therein.

As the basic compound (E), nitrogen-containing organic compounds are preferred and may be used alone or in admixture. Those compounds capable of suppressing the rate of diffusion when the acid generated by the acid generator diffuses within the resist film are useful. The inclusion of nitrogen-containing organic compound holds down the rate of acid diffusion within the resist film, resulting in better resolution. In addition, it suppresses changes in sensitivity following exposure and reduces substrate and environment dependence, as well as improving the exposure latitude and the pattern profile.

Suitable nitrogen-containing organic compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, amide, imide and carbamate derivatives. Illustrative examples are described in JP-A 2008-111103, paragraphs [0149] to [0163]. The basic compound is preferably used in an amount of 0.001 to 2 parts, more preferably 0.01 to 1 part by weight per 100 parts by weight of the base resin (B). At least 0.001 phr achieves the desired addition effect whereas up to 2 phr minimizes the risk of reducing sensitivity.

Tertiary amines are especially preferred as the basic compound. Examples include tri-n-butylamine, tri-n-pentylamine, tri-n-hexylamine, tri-n-octylamine, N,N-dimethylaniline, triethanolamine, triisopropanolamine, tris(2-methoxymethoxyethyl)amine, tris(2-methoxyethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, tris(2-benzoyloxyethyl)amine, tris[2-(4-methoxybenzoyloxy)ethyl]amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tri(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Illustrative examples of the basic compounds include 1-[2-(methoxymethoxy)ethyl]pyrrolidine, 1-[2-(methoxymethoxy)ethyl]piperidine, 4-[2-(methoxymethoxy)ethyl]morpholine, 1-[2-(methoxymethoxy)ethyl]imidazole, 1-[2-(methoxymethoxy)ethyl]benzimidazole, 1-[2-(methoxymethoxy)ethyl]-2-phenylbenzimidazole, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 1-[2-[(2-methoxyethoxy)methoxy]ethyl]imidazole, 1-[2-[(2-methoxyethoxy)methoxy]ethyl]benzimidazole, 1-[2-[(2-methoxyethoxy)methoxy]ethyl]-2-phenylbenzimidazole, 1-[2-[2-(2-methoxyethoxy)ethoxy]ethyl]pyrrolidine, 1-[2-[2-(2-methoxyethoxy)ethoxy]ethyl]piperidine, 4-[2-[2-(2-methoxyethoxy)ethoxy]ethyl]morpholine, 1-[2-[2-(2-methoxyethoxy)ethoxy]ethyl]imidazole, 1-[2-[2-(2-methoxyethoxy)ethoxy]ethyl]benzimidazole, 1-[2-[2-(2-methoxyethoxy)ethoxy]ethyl]-2-phenylbenzimidazole, 1-[2-[2-(2-butoxyethoxy)ethoxy]ethyl]pyrrolidine, 1-[2-[2-(2-butoxyethoxy)ethoxy]ethyl]piperidine, 4-[2-[2-(2-butoxyethoxy)ethoxy]ethyl]morpholine, 1-[2-[2-(2-butoxyethoxy)ethoxy]ethyl]imidazole, 1-[2-[2-(2-butoxyethoxy)ethoxy]ethyl]benzimidazole, 1-[2-[2-(2-butoxyethoxy)ethoxy]ethyl]-2-phenylbenzimidazole, 1-[2-[2-[2-(2-methoxyethoxy)ethoxy]ethoxy]ethyl]pyrrolidine, 1-[2-[2-[2-(2-methoxyethoxy)ethoxy]ethoxy]ethyl]piperidine, 4-[2-[2-[2-(2-methoxyethoxy)ethoxy]ethoxy]ethyl]morpholine, 1-[2-[2-[2-(2-methoxyethoxy)ethoxy]ethoxy]ethyl]imidazole, 1-[2-[2-[2-(2-methoxyethoxy)ethoxy]ethoxy]ethyl]benzimidazole, 1-[2-[2-[2-(2-methoxyethoxy)ethoxy]ethoxy]ethyl]-2-phenyl-benzimidazole, 4-[2-{2-[2-(2-butoxyethoxy)ethoxy]ethoxy}ethyl]morpholine, 2-(1-pyrrolidinyl)ethyl acetate; 2-piperidinoethyl acetate, 2-morpholinoethyl acetate, 2-(1-imidazolyl)ethyl acetate, 2-(1-benzimidazolyl)ethyl acetate, 2-(2-phenyl-1-benzimidazolyl)ethyl acetate, 2-methoxyethyl morpholinoacetate, 2-(1-pyrrolidinyl)ethyl 2-methoxyacetate, 2-piperidinoethyl 2-methoxyacetate, 2-morpholinoethyl 2-methoxyacetate, 2-(1-imidazolyl)ethyl 2-methoxyacetate, 2-(1-benzimidazolyl)ethyl 2-methoxyacetate, 2-(2-phenyl-1-benzimidazolyl)ethyl 2-methoxyacetate, 2-(1-pyrrolidinyl)ethyl 2-(2-methoxyethoxy)acetate, 2-piperidinoethyl 2-(2-methoxyethoxy)acetate, 2-morpholinoethyl 2-(2-methoxyethoxy)acetate, 2-(1-imidazolyl)ethyl 2-(2-methoxyethoxy)acetate, 2-(1-benzimidazolyl)ethyl 2-(2-methoxyethoxy)acetate, 2-(2-phenyl-1-benzimidazolyl)ethyl 2-(2-methoxyethoxy)acetate, 2-(1-pyrrolidinyl)ethyl 2-[2-(2-methoxyethoxy)ethoxy]acetate, 2-piperidinoethyl 2-[2-(2-methoxyethoxy)ethoxy]acetate, 2-morpholinoethyl 2-[2-(2-methoxyethoxy)ethoxy]acetate, 2-(1-imidazolyl)ethyl 2-[2-(2-methoxyethoxy)ethoxy]acetate, 2-(1-benzimidazolyl)ethyl 2-[2-(2-methoxyethoxy)ethoxy]acetate, 2-(2-phenyl-1-benzimidazolyl)ethyl 2-[2-(2-methoxyethoxy)ethoxy]acetate, 2-morpholinoethyl butyrate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl behenate, 2-morpholinoethyl cholate, 2-morpholinoethyl tris(O-acetyl) cholate, 2-morpholinoethyl tris(O-formyl)cholate, 2-morpholinoethyl dehydrocholate, 2-morpholinoethyl cyclopentanecarboxylate, 2-morpholinoethyl cyclohexanecarboxylate, 2-(1-pyrrolidinyl)ethyl 7-oxanorbornane-2-carboxylate, 2-piperidinoethyl 7-oxanorbornane-2-carboxylate, 2-morpholinoethyl 7-oxanorbornane-2-carboxylate, 2-(1-imidazolyl)ethyl 7-oxanorbornane-2-carboxylate, 2-(1-benzimidazolyl)ethyl 7-oxanorbornane-2-carboxylate, 2-(2-phenyl-1-benzimidazolyl)ethyl 7-oxanorbornane-2-carboxylate, 2-morpholinoethyl adamantanecarboxylate, 2-(1-pyrrolidinyl)ethyl formate, 2-piperidinoethyl propionate, 2-morpholinoethyl acetoxyacetate, 2-(1-pyrrolidinyl)ethyl methoxyacetate, 2-(1-pyrrolidinyl) ethyl benzoate, 2-piperidinoethyl benzoate, 2-morpholinoethyl benzoate, 2-(1-imidazolyl)ethyl benzoate, 2-(1-benzimidazolyl)ethyl benzoate, 2-(2-phenyl-1-benzimidazolyl)ethyl benzoate, 2-(1-pyrrolidinyl)ethyl 4-methoxybenzoate, 2-piperidinoethyl 4-methoxybenzoate, 2-morpholinoethyl 4-methoxybenzoate, 2-(1-imidazolyl)ethyl 4-methoxybenzoate, 2-(1-benzimidazolyl)ethyl 4-methoxybenzoate, 2-(2-phenyl-1-benzimidazolyl)ethyl 4-methoxybenzoate, 2-(1-pyrrolidinyl)ethyl 4-phenylbenzoate, 2-piperidinoethyl 4-phenylbenzoate, 2-morpholinoethyl 4-phenylbenzoate, 2-(1-imidazolyl)ethyl 4-phenylbenzoate, 2-(1-benzimidazolyl)ethyl 4-phenylbenzoate, 2-(2-phenyl-1-benzimidazolyl)ethyl 4-phenylbenzoate, 2-(1-pyrrolidinyl)ethyl 1-naphthalenecarboxylate, 2-piperidinoethyl 1-naphthalenecarboxylate, 2-morpholinoethyl 1-naphthalenecarboxylate, 2-(1-imidazolyl)ethyl 1-naphthalenecarboxylate, 2-(1-benzimidazolyl)ethyl 1-naphthalenecarboxylate, 2-(2-phenyl-1-benzimidazolyl)ethyl 1-naphthalenecarboxylate, 2-(1-pyrrolidinyl)ethyl 2-naphthalenecarboxylate, 2-piperidinoethyl 2-naphthalenecarboxylate, 2-morpholinoethyl 2-naphthalenecarboxylate, 2-(1-imidazolyl)ethyl 2-naphthalenecarboxylate, 2-(1-benzimidazolyl)ethyl 2-naphthalenecarboxylate, 2-(2-phenyl-1-benzimidazolyl)ethyl 2-naphthalenecarboxylate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino) propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl) propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, etc.

The dissolution regulator or inhibitor (F) which can be added to the resist composition is a compound having on the molecule at least two phenolic hydroxyl groups which are protected with an acid labile group, or a compound having on the molecule at least one carboxyl group which is protected with an acid labile group. Exemplary regulators are described in JP-A 2008-122932, paragraphs [0155] to [0178].

Optionally, the resist composition may further comprise (G) a surfactant which is commonly used for facilitating the coating operation. Exemplary surfactants are described in JP-A 2008-111103, paragraph [0166].

Optionally, the resist composition may further comprise (H) an acetylene alcohol derivative. Exemplary compounds are described in JP-A 2008-122932, paragraphs to [0181].

Pattern Forming Process

It is now described how to form a pattern using the resist composition of the invention. A pattern may be formed from the resist composition of the invention using any well-known lithography process. The preferred method includes at least the steps of forming a photoresist coating on a substrate, exposing it to high-energy radiation, and developing it with a developer.

The resist composition is applied onto a substrate, typically a silicon wafer by a suitable coating technique such as spin coating. The coating is prebaked on a hot plate at a temperature of 60 to 150° C. for 1 to 10 minutes, preferably 80 to 140° C. for 1 to 5 minutes, to form a photoresist film of 0.1 to 2.0 µm thick. It is noted in conjunction with spin coating that if the resist composition is coated onto the surface of a substrate which has been wetted with the resist solvent or a solution miscible with the resist solvent, then the amount of the resist composition dispensed can be reduced (see JP-A 9-246173).

A patterning mask having the desired pattern is then placed over the photoresist film, and the film exposed through the mask to an electron beam or to high-energy radiation such as deep-UV, excimer laser or x-ray in a dose of 1 to 200 mJ/cm$^2$, and preferably 10 to 100 mJ/cm$^2$. The high-energy radiation used herein preferably has a wavelength in the range of 180 to 250 nm.

Light exposure may be dry exposure in air or nitrogen atmosphere, EB or EUV exposure in vacuum, or immersion lithography of providing a liquid, typically water between the photoresist film and the projection lens.

The immersion lithography involves prebaking a resist film and exposing the resist film to light through a projection lens, with pure water or similar liquid interposed between the resist film and the projection lens. Since this allows projection lenses to be designed to a NA of 1.0 or higher, formation of finer patterns is possible. The immersion lithography is important for the ArF lithography to survive to the 45-nm node. The liquid used herein may be a liquid with a refractive index of at least 1 which is highly transparent at the exposure wavelength, typically pure water or alkane.

The photoresist film formed from the resist composition of the invention has such barrier properties to water that it may inhibit resist components from being leached out in water and as a consequence, eliminate a need for a protective coating in immersion lithography and reduce the cost associated with protective coating formation or the like. The photoresist film has so high a receding contact angle with water that few liquid droplets may be left on the surface of the photoresist film after immersion lithography scanning, minimizing pattern formation failures induced by liquid droplets left on the film surface.

In another version of immersion lithography, a protective coating may be formed on top of the resist film. The resist protective coating used in the immersion lithography may be formed from a coating solution, for example, a topcoat solution of a polymer having acidic units such as 1,1,1,3,3,3-hexafluoro-2-propanol, carboxyl or sulfo groups which is insoluble in water and soluble in an alkaline developer liquid, in a solvent selected from alcohols of at least 4 carbon atoms, ethers of 8 to 12 carbon atoms, and mixtures thereof. The resist protective coating is not limited thereto.

The resist protective coating may be formed by spin coating a topcoat solution onto a prebaked photoresist film, and prebaking on a hot plate at 50 to 150° C. for 1 to 10 minutes, preferably at 70 to 140° C. for 1 to 5 minutes. Preferably the protective coating has a thickness in the range of 10 to 500 nm. As in the case of resist compositions, the amount of the protective coating material dispensed in forming a protective coating by spin coating may be reduced by previously wetting the resist film surface with a suitable solvent and applying the protective coating material thereto.

After exposure to high-energy radiation through a photomask, the resist film is post-exposure baked (PEB) on a hot plate at 60 to 150° C. for 1 to 5 minutes, and preferably at 80 to 140° C. for 1 to 3 minutes.

Where a resist protective coating is used, sometimes water is left on the protective coating prior to PEB. If PEB is performed in the presence of residual water, water can penetrate through the protective coating to suck up the acid in the resist during PEB, impeding pattern formation. To fully remove the water on the protective coating prior to PEB, the water on the protective coating should be dried or recovered by suitable means, for example, spin drying, purging the protective coating surface with dry air or nitrogen, or optimizing the shape of a water recovery nozzle on the relevant stage or a water recovery process.

After exposure, development is carried out using as the developer an aqueous alkaline solution, such as a 0.1 to 5 wt %, preferably 2 to 3 wt %, aqueous solution of tetramethylammonium hydroxide (TMAH), this being done by a conventional method such as dip, puddle, or spray development for a period of 10 to 300 seconds, and preferably 0.5 to 2 minutes. A typical developer is a 2.38 wt % TMAH aqueous solution. These steps result in the formation of the desired pattern on the substrate.

Where polymer P1 is used as an additive to a resist material for use with mask blanks, a resist solution is prepared by adding polymer P1 to any one of the aforementioned base resins and dissolving them in an organic solvent. The resist solution is coated on a mask blank substrate of $SiO_2$, Cr, CrO, CrN, MoSi or the like. By further forming a SOG film and an organic undercoat film between the photoresist and the blank substrate, there is provided a three-layer structure which is also acceptable herein.

As the base resin of the resist composition for use with mask blanks, novolac resins and hydroxystyrene are often used, Those resins in which alkali soluble hydroxyl groups are substituted by acid labile groups are used for positive resists while these resins in combination with crosslinking agents are used for negative resists. Base polymers which can be used herein include copolymers of hydroxystyrene with one or more of (meth)acrylic derivatives, styrene, vinyl naphthalene, vinyl anthracene, vinyl pyrene, hydroxyvinyl naphthalene, hydroxyvinyl anthracene, indene, hydroxyindene, acenaphthylene, and norbornadiene.

Once the resist coating is formed, the structure is exposed to EB in vacuum using an EB image-writing system. The exposure is followed by post-exposure baking (PEB) and development in an alkaline developer for 10 to 300 seconds, thereby forming a pattern.

EXAMPLE

Examples are given below by way of illustration and not by way of limitation. The abbreviations Mw and Mn are weight and number average molecular weights, respectively, as measured by GPC using polystyrene standards, and Mw/Mn is a polydispersity index. Me stands for methyl, Et for ethyl, and PGMEA for propylene glycol monomethyl ether acetate.

[Monomer Synthesis]

Fluorinated monomers within the scope of the invention were synthesized.

Example 1

Synthesis of Monomer 1

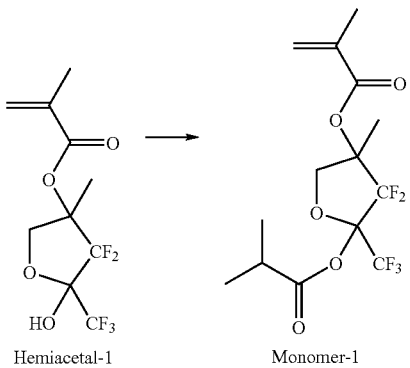 [SMILES: C=C(C)C(=O)OC1(C)COC(O)(C(F)(F)F)C1(F)F ; C=C(C)C(=O)OC1(C)COC(OC(=O)C(C)C)(C(F)(F)F)C1(F)F]

Hemiacetal-1          Monomer-1

While a mixture of 50.0 g of Hemiacetal-1, 40.8 g of pyridine, and 100 g of acetonitrile was stirred under ice cooling in a nitrogen atmosphere, 22.0 g of isobutyric acid chloride was added dropwise over 30 minutes. After 30 minutes, the reaction solution was diluted by adding 100 g of hexane, and 400 g of water was then added to the reaction solution, which was stirred for 30 minutes to quench the reaction and decompose the excess reactants. After ordinary aqueous work-up, the reaction product was purified by vacuum distillation, obtaining 60.8 g of the target compound (yield 98%). Colorless liquid, boiling point 63-67° C./13 Pa. On NMR analysis, it was a mixture of diastereomers in a molar ratio 67:33.

IR (thin film): ν=2981, 2940, 2883, 1774, 1727, 1639, 1471, 1452, 1388, 1336, 1303, 1282, 1218, 1155, 1112, 1081, 1039, 1004, 939, 927 $cm^{-1}$ $^1$H-NMR (300 MHz in DMSO-$d_6$) of mixture of 67:33 (mole) diastereomers: δ=1.11 (0.99H, d, J=6.9 Hz), 1.12 (0.99H, d, J=7.1 Hz), 1.14 (4.02H, d, J=6.9 Hz), 1.66-1.70 (3H, m), 1.85-1.90 (3H, m), 2.70 (0.33H, qq, J=7.1, 6.9 Hz), 2.74 (0.67H, sep, J=6.9 Hz), 4.65 (0.67H, br.d, J=11.1 Hz), 4.68 (0.33H, dd, J=9.8, 1.5 Hz), 4.79 (0.33H, br.d, J=9.8 Hz), 4.85 (0.67H, dd, J=11.1, 2.7 Hz), 5.80 (0.67H, m), 5.82 (0.33H, m), 6.08 (0.67H, m), 6.09 (0.33H, m) ppm $^{19}$F-NMR (283 MHz in DMSO-$d_6$) of mixture of 67:33 (mole) diastereomers: δ=−124.32 (0.67F, dq, J=250, 17 Hz), −119.75 (0.33F, dqd, J=246, 17.4 Hz), −110.80 (0.33F, d, J=246 Hz), −109.49 (0.67F, d, J=250 Hz), −80.19 (0.67F, d, J=17 Hz), −79.92 (0.33F, d, J=17 Hz) ppm

Example 2

Synthesis of Monomer 2

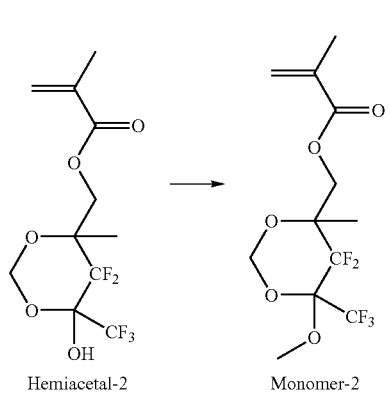 [SMILES: C=C(C)C(=O)OCC1(C)OCOC(O)(C(F)(F)F)C1(F)F ; C=C(C)C(=O)OCC1(C)OCOC(OC)(C(F)(F)F)C1(F)F]

Hemiacetal-2 → Monomer-2

A mixture of 32.0 g of Hemiacetal-2, 28.4 g of methyl iodide, 27.8 g of silver(I) oxide, and 150 g of ethyl acetate was stirred at 40° C. for 24 hours. After the insoluble was filtered off, the reaction mixture was vacuum concentrated and purified by silica gel column chromatography, obtaining 27.1 g of the target compound (yield 81%).

Example 3

Synthesis of Monomer 3

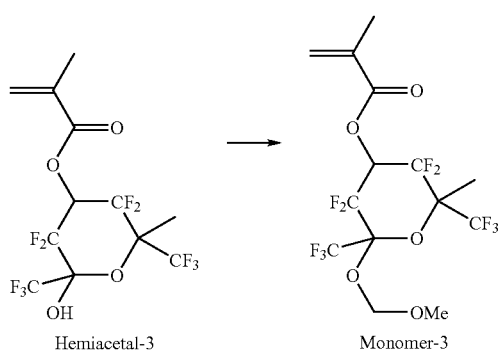 [SMILES: C=C(C)C(=O)OC1C(F)(F)C(C)(C(F)(F)F)OC(O)(C(F)(F)F)C1(F)F ; C=C(C)C(=O)OC1C(F)(F)C(C)(C(F)(F)F)OC(OCOC)(C(F)(F)F)C1(F)F]

Hemiacetal-3 → Monomer-3

To a mixture of 40.8 g of Hemiacetal-3, 15.2 g of triethylamine, 1.5 g of sodium iodide, and 200 g of acetonitrile was added 10.5 g of chloromethyl methyl ether. The mixture was stirred at 50° C. for 16 hours. After ordinary aqueous work-up, the reaction product was purified by silica gel column chromatography, obtaining 43.0 g of the target compound (yield 95%).

Example 4

Synthesis of Monomer 4

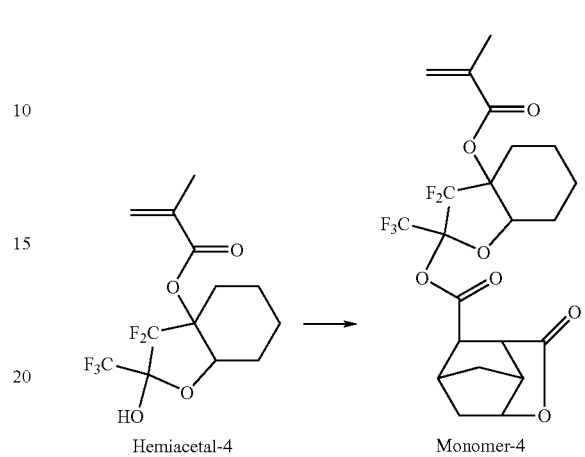

Hemiacetal-4 → Monomer-4

Monomer 4 was synthesized by the same procedure as in Example 1 aside from using Hemiacetal-4 instead of Hemiacetal-1, and 2,6-norbornanecarbolactone-3-carbonyl chloride instead of isobutyric acid chloride.

Example 5

Synthesis of Monomer 5

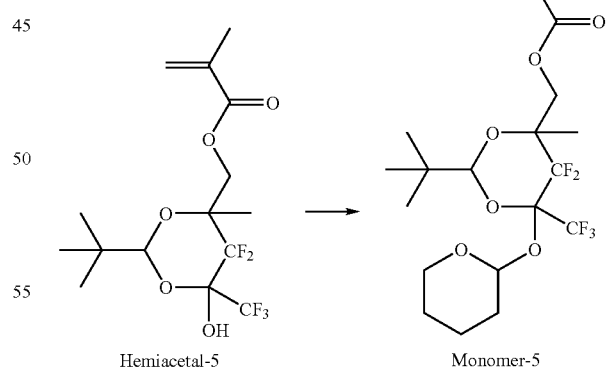

Hemiacetal-5 → Monomer-5

Monomer 5 was synthesized by the same procedure as in Example 3 aside from using Hemiacetal-5 instead of Hemiacetal-3, and 2-chlorotetrahydropyran instead of chloromethyl methyl ether.

Example 6

Synthesis of Monomer 6

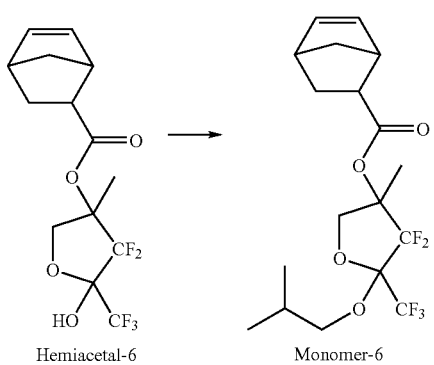 [SMILES: CC1(OC(=O)C2CC3C=CC2C3)COC(O)(C(F)(F)F)C1(F)F ; CC(C)COC1(C(F)(F)F)OCC(C)(OC(=O)C2CC3C=CC2C3)C1(F)F]

Hemiacetal-6 → Monomer-6

Monomer 6 was synthesized by the same procedure as in Example 2 aside from using Hemiacetal-6 instead of Hemiacetal-2, and isobutyl iodide instead of methyl iodide.

Example 7

Synthesis of Monomer 7

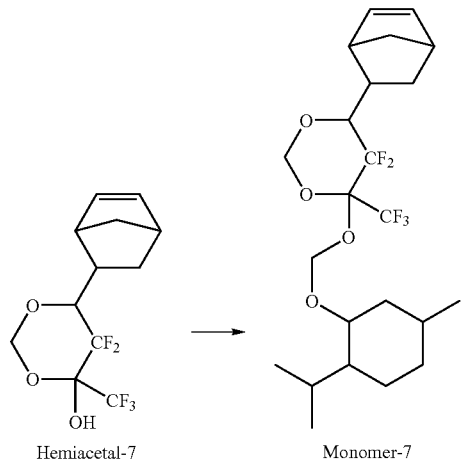 [SMILES: OC1(C(F)(F)F)OCOC(C2CC3C=CC2C3)C1(F)F ; CC1CCC(C(C)C)C(OCOC2(C(F)(F)F)OCOC(C3CC4C=CC3C4)C2(F)F)C1]

Hemiacetal-7 → Monomer-7

Monomer 7 was synthesized by the same procedure as in Example 3 aside from using Hemiacetal-7 instead of Hemiacetal-3, and chloromethyl menthyl ether instead of chloromethyl methyl ether.

Example 8

Synthesis of Monomer 8

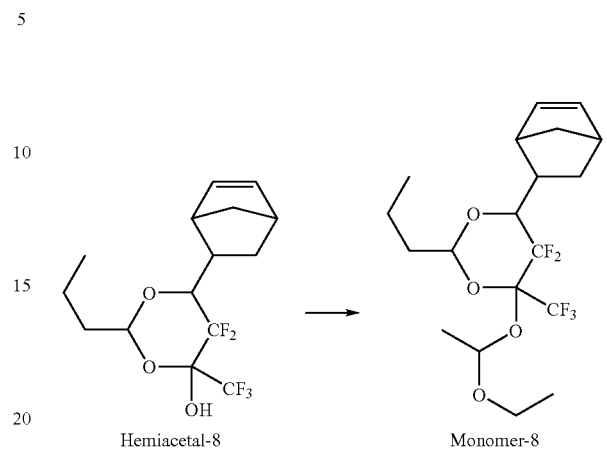

Hemiacetal-8 → Monomer-8

Monomer 8 was synthesized by the same procedure as in Example 3 aside from using Hemiacetal-8 instead of Hemiacetal-3, and 1-chloroethyl ethyl ether instead of chloromethyl methyl ether.

Example 9

Synthesis of Monomer 9

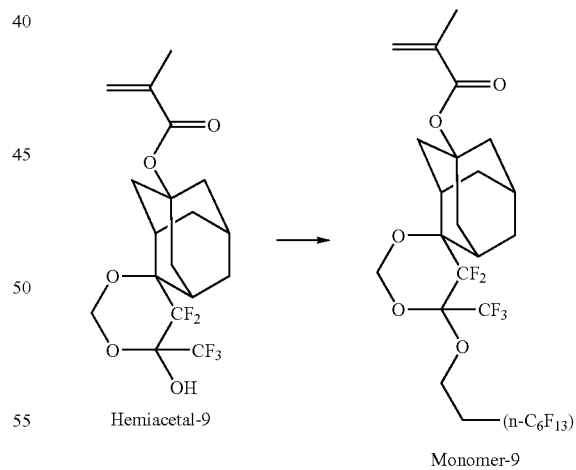

Hemiacetal-9 → Monomer-9

Monomer 9 was synthesized by the same procedure as in Example 2 aside from using Hemiacetal-9 instead of Hemiacetal-2, and 1,1,1,2,2,3,3,4,4,5,5,6,6-tridecafluoro-1-iodooctane instead of methyl iodide.

Example 10

Synthesis of Monomer 10

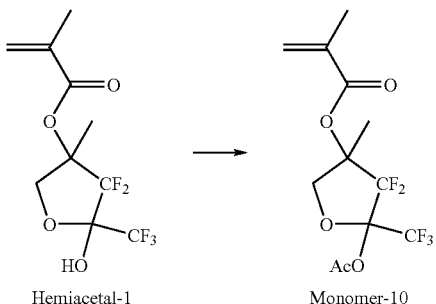 [SMILES: C=C(C)C(=O)OC1(C)COC(O)(C(F)(F)F)C1(F)F ; C=C(C)C(=O)OC1(C)COC(OC(C)=O)(C(F)(F)F)C1(F)F]

Monomer 10 was synthesized by the same procedure as in Example 1 aside from using acetic anhydride instead of isobutyric acid chloride.

Example 11

Synthesis of Monomer 11

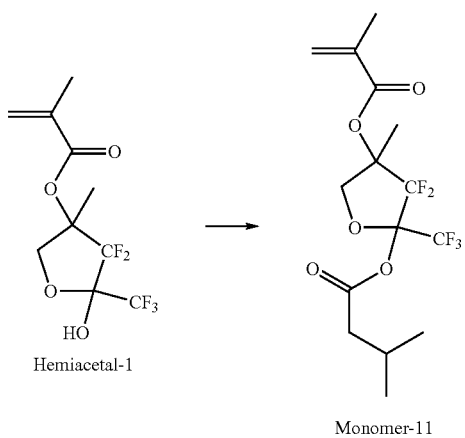 [SMILES: C=C(C)C(=O)OC1(C)COC(O)(C(F)(F)F)C1(F)F ; C=C(C)C(=O)OC1(C)COC(OC(=O)CC(C)C)(C(F)(F)F)C1(F)F]

Monomer 11 was synthesized by the same procedure as in Example 1 aside from using isovaleric acid chloride instead of isobutyric acid chloride.

Colorless liquid, boiling point 70° C./13 Pa

IR (thin film): $\nu$=2966, 2935, 2877, 1779, 1727, 1639, 1469, 1452, 1386, 1371, 1336, 1301, 1282, 1216, 1155, 1110, 1087, 1039, 1004, 946, 927 cm$^{-1}$ $^1$H-NMR (600 MHz in DMSO-d$_6$) of mixture of 65:35 (mole) diastereomers: $\delta$=0.89 (1.05H, d, J=6.4 Hz), 0.90 (1.05H, d, J=6.4 Hz), 0.92 (1.95H, d, J=6.4 Hz), 0.92 (1.95H, d, J=6.4 Hz), 1.66 (1.05H, br.d, J=3.7 Hz), 1.68 (1.95H, br.d, J=3.2 Hz), 1.86 (1.95H, m), 1.87 (1.05H, m), 1.90-2.05 (1H, m), 2.31 (0.35H, dd, J=15.6, 7.3 Hz), 2.36 (0.65H, dd, J=15.5, 6.8 Hz), 2.37 (0.35H, dd, J=15.6, 6.4 Hz), 2.40 (0.65H, dd, J=15.5, 6.9 Hz), 4.63 (0.65H, br.d, J=11.0 Hz), 4.66 (0.35H, dd, J=10.1, 1.0 Hz), 4.77 (0.35H, br.d, J=10.1 Hz), 4.83 (0.65H, dd, J=11.0, 2.3 Hz), 5.78 (0.65H, m), 5.81 (0.35H, m), 6.06 (0.65H, m), 6.08 (0.35H, m) ppm $^{19}$F-NMR (565 MHz in DMSO-d$_6$) of mixture of 65:35 (mole) diastereomers: $\delta$=−124.06 (0.65F, dq, J=249, 16 Hz), −119.57 (0.35F, dqd, J=246, 17.3 Hz), −110.46 (0.35F, d, J=246 Hz), −108.98 (0.65F, d, J=249 Hz), −79.90 (0.65F, d, J=16 Hz), −79.57 (0.35F, d, J=18 Hz) ppm

Example 12

Synthesis of Monomer 12

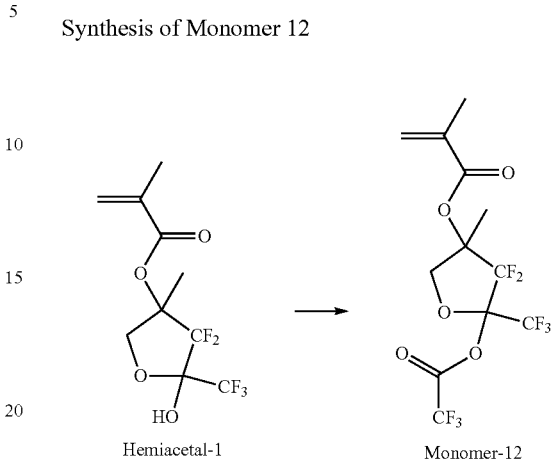

Monomer 12 was synthesized by the same procedure as in Example 1 aside from using trifluoroacetic anhydride instead of isobutyric acid chloride.

Colorless liquid, boiling point 74° C./800 Pa

IR (thin film): $\nu$=2989, 2937, 1814, 1731, 1639, 1454, 1405, 1388, 1340, 1301, 1282, 1228, 1180, 1153, 1101, 1012, 950, 919, 842 cm$^{-1}$ $^1$H-NMR (300 MHz in DMSO-d$_6$) of mixture of 60:40 (mole) diastereomers: $\delta$=1.71 (1.2H, br.d, J=3.8 Hz), 1.73 (1.8H, br.d, J=3.3 Hz), 1.88 (1.2H, m), 1.89 (1.8H, m), 4.80 (0.6H, br.d, J=11.1 Hz), 4.87 (0.4H, dd, J=10.6, 1.2 Hz), 5.01 (0.4H, br.d, J=10.6 Hz), 5.03 (0.6H, dd, J=11.1, 2.5 Hz), 5.81 (0.4H, m), 5.83 (0.4H, m), 6.06 (0.4H, m), 6.10 (0.4H, m) ppm $^{19}$F-NMR (283 MHz in DMSO-d$_6$) of mixture of 60:40 (mole) diastereomers: $\delta$=−124.81 (0.6F, dq, J=248, 16 Hz), −120.54 (0.4F, dqd, 3=246, 17.3 Hz), −117.96 (0.4F, d, J=246 Hz), −113.14 (0.6F, d, J=248 Hz), −79.29 (0.6F, d, J=16 Hz), −78.74 (0.4F, d, J=16 Hz), −75.95 (0.4F, s), −75.92 (0.6F, s) ppm

Example 13

Synthesis of Monomer 13

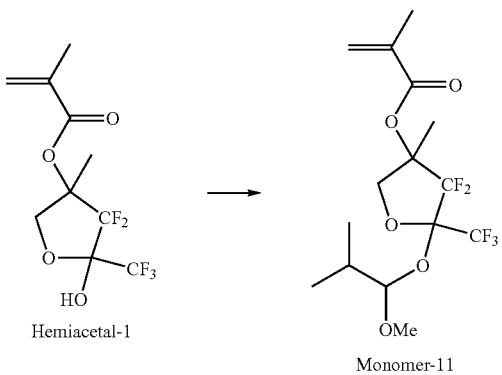 [SMILES: C=C(C)C(=O)OC1(C)COC(O)(C(F)(F)F)C1(F)F ; C=C(C)C(=O)OC1(C)COC(OC(OC)C(C)C)(C(F)(F)F)C1(F)F]

Monomer 13 was synthesized by the same procedure as in Example 3 aside from using Hemiacetal-1 instead of Hemiacetal-3, and 1-chloro-1-methoxy-2-methylpropane instead of chloromethyl methyl ether.

Colorless liquid, boiling point 70° C./27 Pa

IR (thin film): ν=2969, 2881, 2848, 1727, 1639, 1473, 1452, 1388, 1367, 1328, 1303, 1284, 1207, 1159, 1103, 1066, 1010, 970, 946 cm$^{-1}$ $^1$H-NMR (600 MHz in DMSO-$d_6$) of mixture of 33:32:19:16 (mole) four diastereomers: δ=0.80-0.90 (6H, m), 1.61-1.71 (3H, m), 1.84-1.95 (4H, m), 3.20 (0.16H, s), 3.26 (0.19H, s), 3.30 (0.33H, s), 3.34 (0.32H, s), 4.35-4.80 (2H, m), 5.72-5.82 (1H, m), 6.05-6.10 (1H, m) ppm $^{19}$F-NMR (565 MHz in DMSO-$d_6$) of mixture of 33:32:19:16 (mole) diastereomers: δ=−124.63 (0.33F, dq, J=243, 19 Hz), −124.30 (0.32F, dq, J=236, 18 Hz), −121.63 (0.32F, d, J=236 Hz), −121.49 (0.16F, d, J=241 Hz), −120.52 (0.16F, dq, J=241, 17 Hz), −119.38 (0.19F, dq, J=245, 21 Hz), −116.83 (0.19F, d, J=24.5 Hz), −114.83 (0.33F, d, J=243 Hz), −79.00 (0.19F, d, J=21 Hz), −78.76 (0.33F, d, J=20 Hz), −78.29 (0.16F, d, J=18 Hz), −78.23 (0.32F, d, J=20 Hz) ppm

[Polymer Synthesis]

Polymerizable monomers (Monomers 14 to 29) and an amine (Base 1) used in polymer synthesis are identified below by their structural formulae.

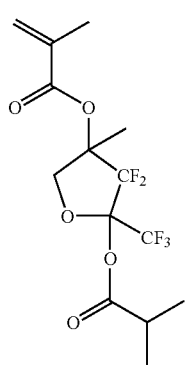

Monomer 14

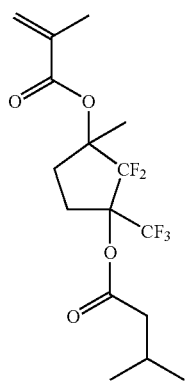

Monomer 15

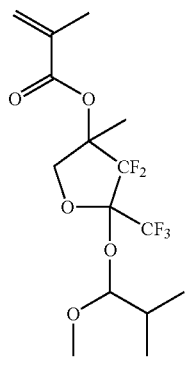

Monomer 16

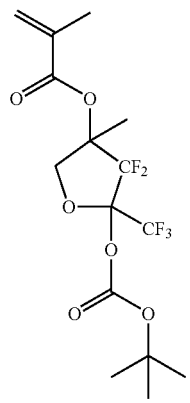

Monomer 17

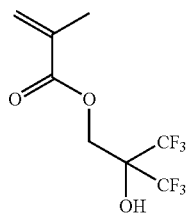

Monomer 18

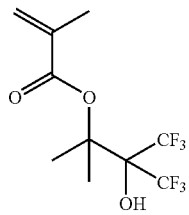

Monomer 19

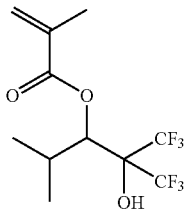

Monomer 20

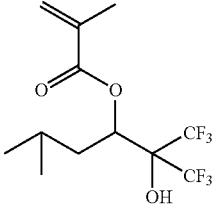

Monomer 21

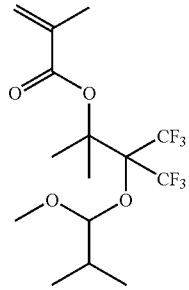

Monomer 22

Monomer 23

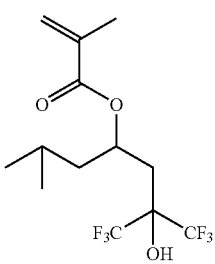

Monomer 24

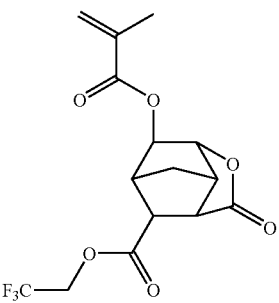

Monomer 25

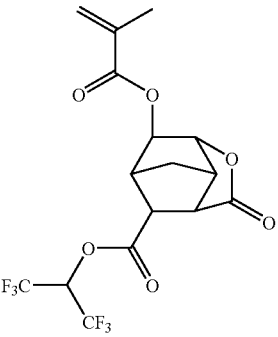

Monomer 26

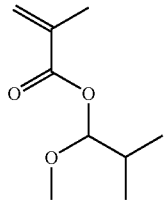

Monomer 27

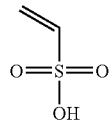

Monomer 28

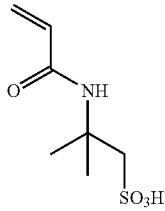

Monomer 29

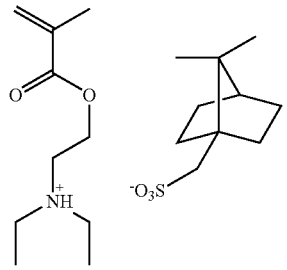

Base 1

(structure shown)

Polymer Synthesis Example 1

Copolymerization of Monomers 14 and 19 (20/80)

In a nitrogen atmosphere, a flask was charged with 23.41 g of Monomer 14, 77.11 g of Monomer 19, 3.75 g of 2,2'-azobis(isobutyric acid) dimethyl, and 100.1 g of methyl ethyl ketone to form a monomer solution at a temperature of 20-25° C. In a nitrogen atmosphere, another flask was charged with 50.1 g of methyl ethyl ketone, which was heated at 80° C. with stirring. The monomer solution was added dropwise thereto over 4 hours. After the completion of dropwise addition, the polymerization solution was stirred for a further 2 hours while maintaining the temperature of 80° C. At the end of maturing, the solution was cooled to room temperature. To the flask 200 g of toluene was admitted. Using an evaporator, the reaction mixture was concentrated until the total weight reached 250 g. The concentrate was added dropwise to 1,500 g of hexane. The copolymer thus precipitated was separated and washed with 600 g of hexane, obtaining a white solid. The solid was vacuum dried at 50° C. for 20 hours, yielding 69.3 g of the target polymer, designated Polymer 2. On $^1$H-NMR analysis of resin composition, the copolymer consisted of Monomers 14 and 19 in a ratio of 19/81 mol %.

Polymer Synthesis Examples 2 to 19

As in Polymer Synthesis Example 1, Polymers 1 to 19 were synthesized using the polymerizable monomers (Monomers 14 to 29) in accordance with the formulation shown in Tables 1 to 5.

TABLE 1

| | Monomer | | | | | Yield | | |
|---|---|---|---|---|---|---|---|---|
| | 14 | 18 | 19 | 20 | 21 | (%) | Mw | Mw/Mn |
| Polymer 1 | 20 | 80 | | | | 68.2 | 7,400 | 1.4 |
| Polymer 2 | 20 | | 80 | | | 69.3 | 7,800 | 1.4 |
| Polymer 3 | 20 | | | 80 | | 70.2 | 7,500 | 1.4 |
| Polymer 4 | 20 | | | | 80 | 69.8 | 7,400 | 1.4 |

TABLE 1-continued
| Monomer | | | | | Yield | | |
|---|---|---|---|---|---|---|---|
| 14 | 18 | 19 | 20 | 21 | (%) | Mw | Mw/Mn |
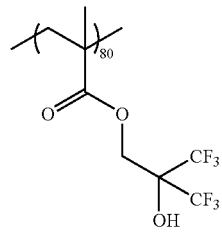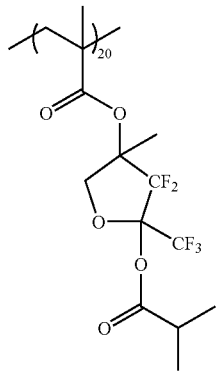
Polymer 1
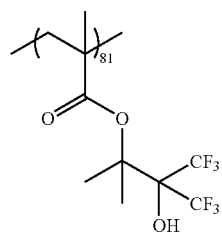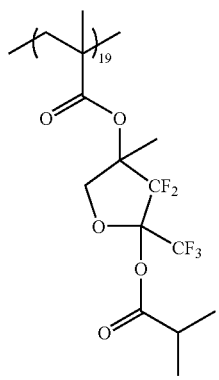
Polymer 2
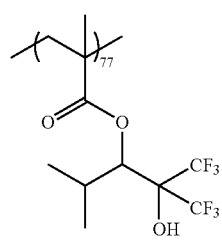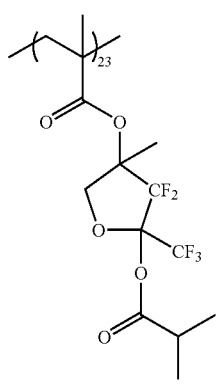
Polymer 3
TABLE 1-continued
| Monomer | | | | | Yield | | |
|---|---|---|---|---|---|---|---|
| 14 | 18 | 19 | 20 | 21 | (%) | Mw | Mw/Mn |
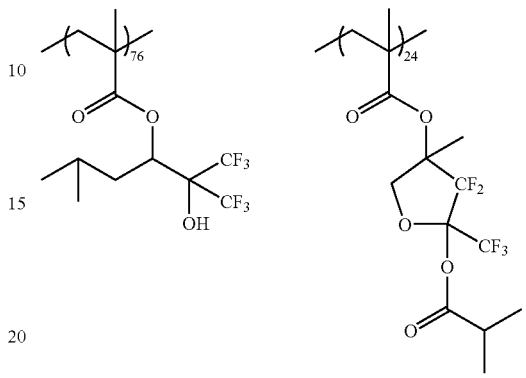
Polymer 4
TABLE 2
| | Monomer | | | | Yield | | |
|---|---|---|---|---|---|---|---|
| | 15 | 16 | 17 | 19 | (%) | Mw | Mw/Mn |
| Polymer 5 | 20 | | | 80 | 69.2 | 7,300 | 1.4 |
| Polymer 6 | | 20 | | 80 | 71.2 | 7,100 | 1.4 |
| Polymer 7 | | | 20 | 80 | 70.5 | 7,100 | 1.4 |
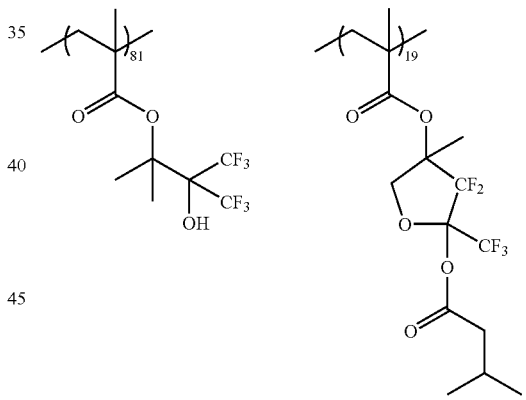
Polymer 5
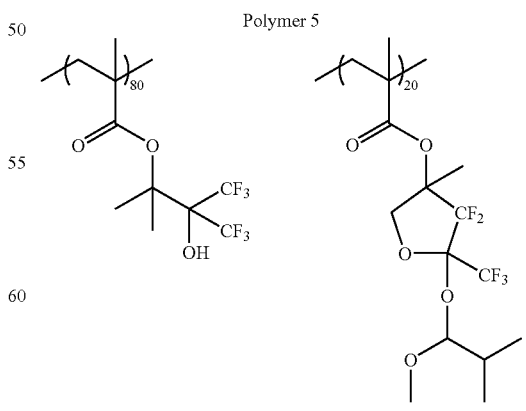
Polymer 6

TABLE 2-continued
| | Monomer | | | | Yield | | |
|---|---|---|---|---|---|---|---|
| | 15 | 16 | 17 | 19 | (%) | Mw | Mw/Mn |
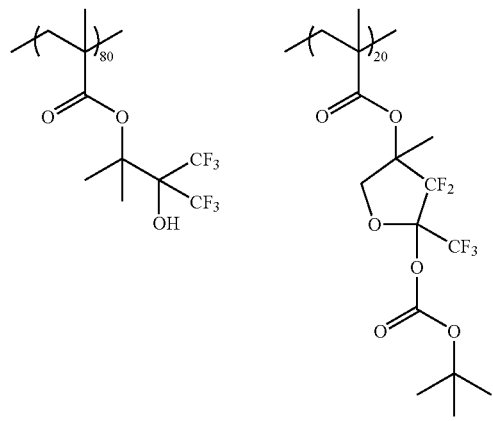
Polymer 7
TABLE 3
| | Monomer | | | | | Yield | | |
|---|---|---|---|---|---|---|---|---|
| | 14 | 18 | 19 | 20 | 21 | (%) | Mw | Mw/Mn |
| Polymer 8 | 40 | 60 | | | | 71.2 | 7,300 | 1.4 |
| Polymer 9 | 40 | | 60 | | | 72.4 | 7,700 | 1.4 |
| Polymer 10 | 40 | | | 60 | | 71.6 | 7,600 | 1.4 |
| Polymer 11 | 40 | | | | 60 | 69.4 | 7,500 | 1.4 |
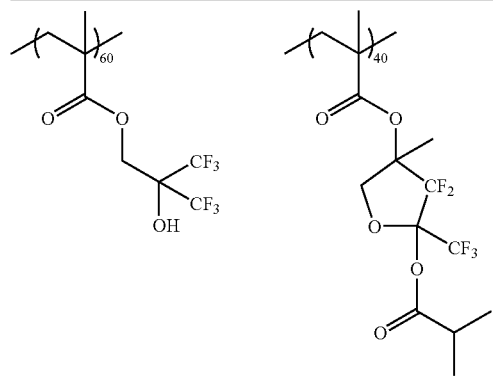
Polymer 8
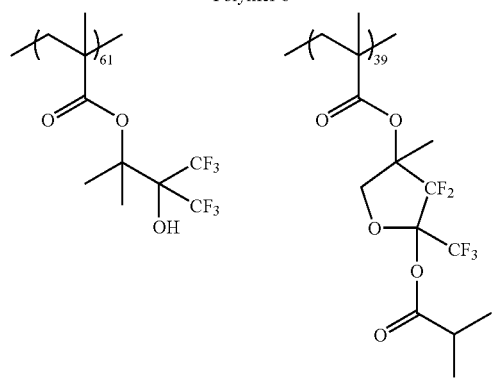
Polymer 9
TABLE 3-continued
| | Monomer | | | | | Yield | | |
|---|---|---|---|---|---|---|---|---|
| | 14 | 18 | 19 | 20 | 21 | (%) | Mw | Mw/Mn |
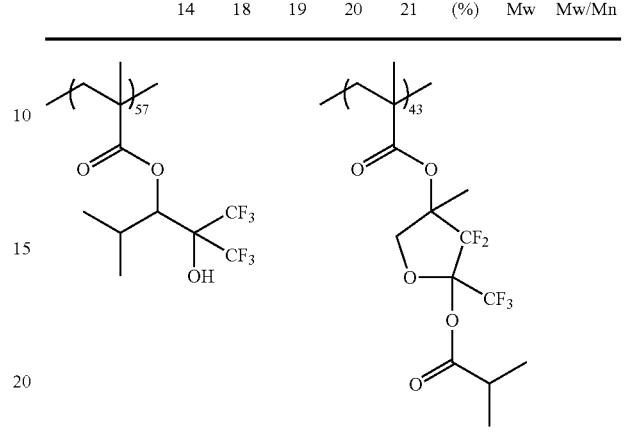
Polymer 10
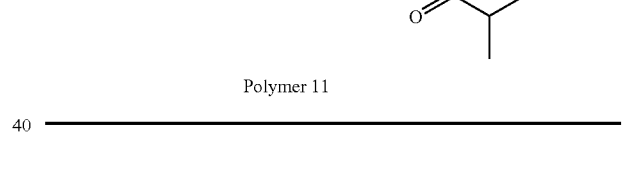
Polymer 11
TABLE 4
| | Monomer | | | | Yield | | |
|---|---|---|---|---|---|---|---|
| | 15 | 16 | 17 | 19 | (%) | Mw | Mw/Mn |
| Polymer 12 | 40 | | | 60 | 72.4 | 7,200 | 1.4 |
| Polymer 13 | | 40 | | 60 | 71.1 | 7,500 | 1.4 |
| Polymer 14 | | | 40 | 60 | 70.7 | 7,400 | 1.4 |
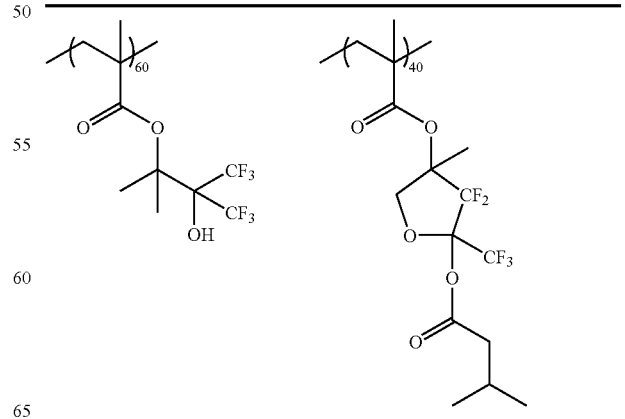
Polymer 12

TABLE 4-continued
| | Monomer | | | | Yield | | |
|---|---|---|---|---|---|---|---|
| | 15 | 16 | 17 | 19 | (%) | Mw | Mw/Mn |
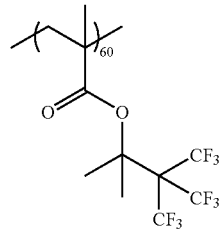
Polymer 13
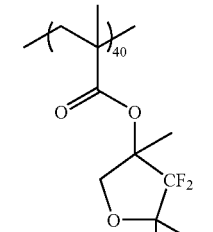
Polymer 14
TABLE 5
| | Monomer | | | | | | | Yield | | |
|---|---|---|---|---|---|---|---|---|---|---|
| | 14 | 19 | 22 | 23 | 24 | 25 | 26 | (%) | Mw | Mw/Mn |
| Polymer 15 | 20 | 70 | 10 | | | | | 68.9 | 7,400 | 1.4 |
| Polymer 16 | 20 | 70 | | 10 | | | | 70.5 | 7,500 | 1.4 |
| Polymer 17 | 20 | 70 | | | 10 | | | 71.4 | 7,400 | 1.4 |
| Polymer 18 | 20 | 70 | | | | 10 | | 72.1 | 7,300 | 1.4 |
| Polymer 19 | 20 | 70 | | | | | 10 | 71.8 | 7,600 | 1.4 |
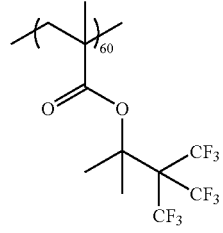
TABLE 5-continued
| | Monomer | | | | | | | Yield | | |
|---|---|---|---|---|---|---|---|---|---|---|
| | 14 | 19 | 22 | 23 | 24 | 25 | 26 | (%) | Mw | Mw/Mn |
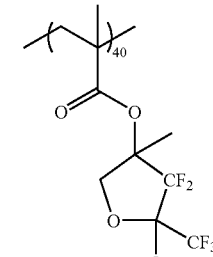
Polymer 15
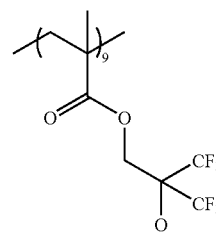
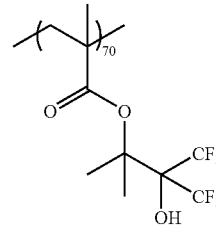
Polymer 16
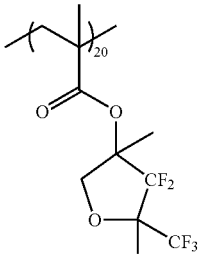

TABLE 5-continued

| | Monomer | | | | | | Yield | | |
|---|---|---|---|---|---|---|---|---|---|
| 14 | 19 | 22 | 23 | 24 | 25 | 26 | (%) | Mw | Mw/Mn |

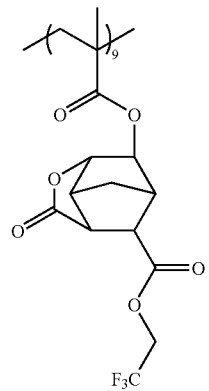

Polymer 17

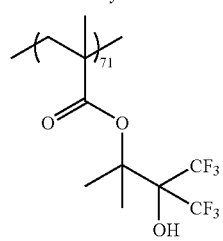

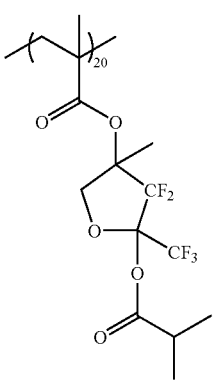

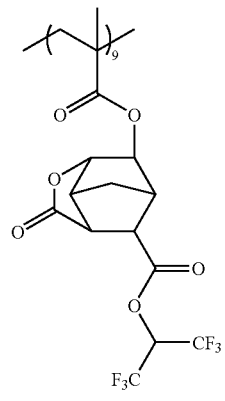

Polymer 18

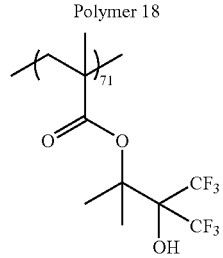

TABLE 5-continued

| | Monomer | | | | | | Yield | | |
|---|---|---|---|---|---|---|---|---|---|
| 14 | 19 | 22 | 23 | 24 | 25 | 26 | (%) | Mw | Mw/Mn |

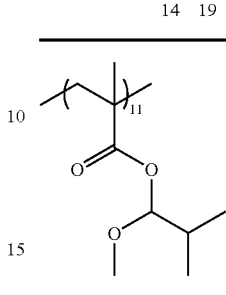

Polymer 19

Polymer Synthesis Example 20

Copolymerization of Monomers 19 and 27 (90/10) in the Presence of Base 1

In a nitrogen atmosphere, a flask was charged with 96.46 g of Monomer 19, 4.03 g of Monomer 27, 1.87 g of Base 1, 4.18 g of 2,2'-azobis(isobutyric acid) dimethyl, and 155.56 g of isopropyl alcohol to form a monomer solution at a temperature of 20-25° C. In a nitrogen atmosphere, another flask was charged with 77.78 g of isopropyl alcohol, which was heated at 80° C. with stirring. The monomer solution was added dropwise thereto over 4 hours. After the completion of dropwise addition, the polymerization solution was stirred for a further 2 hours while maintaining the temperature of 80° C. At the end of maturing, the solution was cooled to room temperature. After 300 g of 2-propanol was added, the polymerization solution was washed three times with 300 g of ultrapure water. The organic layer extracted was concentrated on an evaporator until the total weight reached 200 g. The concentrate was crystallized in 1,500 g of hexane. The copolymer thus precipitated was separated and washed with 600 g of hexane, obtaining a white solid. The solid was vacuum dried at 50° C. for 20 hours, yielding 79.8 g of the target polymer, designated Polymer 20. On $^{1}$H-NMR analysis of resin composition, the copolymer consisted of Monomer 19, Monomer 27 and Base 1 salt in a ratio of 89/9/2 mol % as shown below.

Polymer 20

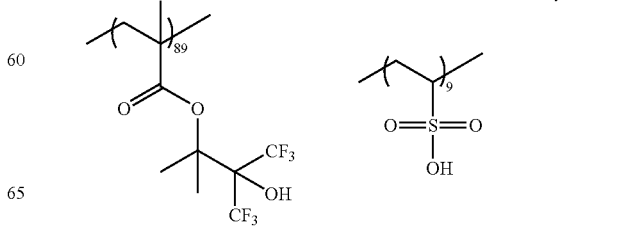

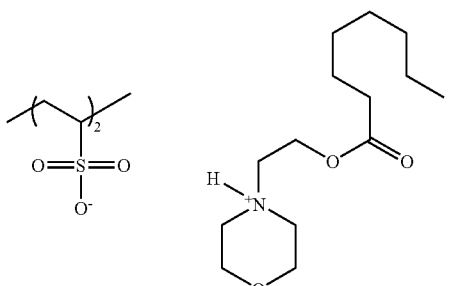

Polymer Synthesis Example 21

Copolymerization of Monomers 19 and 28 (90/10) in the Presence of Base 1

By the same procedure as in the synthesis of Polymer 20, aside from using Monomer 19, Monomer 28 and Base 1, 75.3 g of the target polymer (Polymer 21) was synthesized. On $^1$H-NMR analysis of resin composition, the copolymer consisted of Monomer 19, Monomer 28 and Base 1 salt in a ratio of 90/8/2 mol % as shown below.

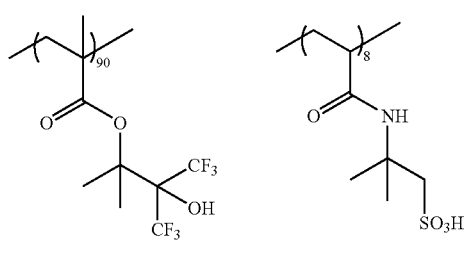

Polymer 21

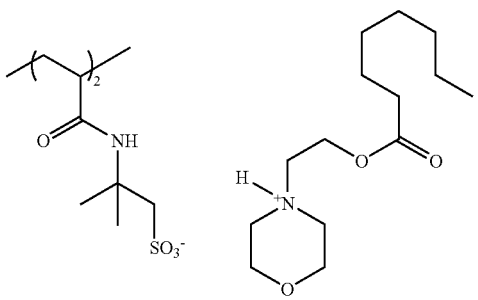

Polymer Synthesis Example 22

Copolymerization of Monomers 19 and 29 (90/10)

By the same procedure as in the synthesis of Polymer 20, aside from using Monomers 19 and 29, 81.5 g of the target polymer (Polymer 22) was synthesized. On $^1$H-NMR analysis of resin composition, the copolymer consisted of Monomers 19 and 29 in a ratio of 90/10 mol % as shown below.

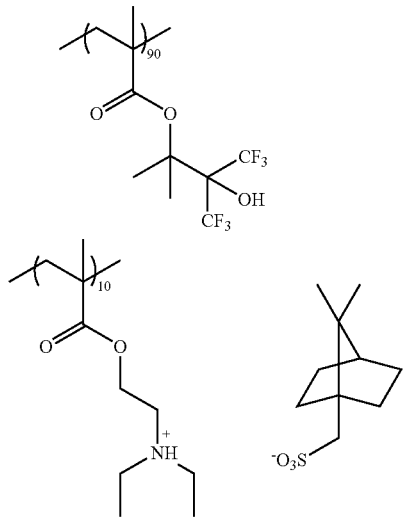

Polymer 22

Comparative Polymer Synthesis Example 1

Synthesis of Homopolymer of Monomer 19

In a nitrogen atmosphere, a flask was charged with 100.0 g of Monomer 19, 3.91 g of 2,2'-azobis(isobutyric acid) dimethyl, and 100.0 g of isopropyl alcohol to form a monomer solution at a temperature of 20-25° C. In a nitrogen atmosphere, another flask was charged with 50.0 g of isopropyl alcohol, which was heated at 80° C. with stirring. The monomer solution was added dropwise thereto over 4 hours. After the completion of dropwise addition, the polymerization solution was stirred for a further 3 hours while maintaining the temperature of 80° C. At the end of maturing, the solution was cooled to room temperature. The polymerization solution was added dropwise to 2,000 g of water. The polymer thus precipitated was filtered and washed four times with 600 g of a 9/1 hexane/isopropyl ether mixture, obtaining a white solid. The solid was vacuum dried at 50° C. for 20 hours, yielding 92.8 g of the target polymer, designated Comparative Polymer 1. On GPC analysis, the polymer had Mw of 7,800 and Mw/Mn of 1.6.

[Evaluation of Protective Coating]

Resist protective topcoat solutions TC-1 to 27 and Comparative-TC-1 to 2 were prepared by dissolving 1.0 g of each of Inventive Polymers 1 to 22 and Comparative Polymer 1 in a solvent mixture of 23 g of diisopentyl ether and 2 g of 2-methyl-1-butanol in accordance with the formulation of Table 6 and filtering through a polypropylene filter with a pore size of 0.2 µm.

The resist protective topcoat solutions were spin coated onto silicon substrates and baked at 100° C. for 60 seconds to form protective films TC-1 to 27 and Comparative-TC-1 to 2 of 50 nm thick. The wafers coated with protective films were tested for the following properties: (1) a refractive index at wavelength 193 nm using a spectroscopic ellipsometer of J. A. Woollam Co., (2) a film thickness change after rinsing with pure water for 5 minutes, (3) a film thickness change after development with 2.38 wt % tetramethylammonium hydroxide (TMAH) aqueous solution, and (4) a sliding angle and a receding contact angle using an inclination contact angle meter Drop Master 500 (Kyowa Interface Science Co., Ltd.). The results are shown in Table 6.

TABLE 6

| Resist protective topcoat | Polymers in protective topcoat (mix ratio) | Refractive index @193 nm | Film thickness change after water rinsing (nm) | Film thickness change after development (nm) | Sliding angle (°) | Receding contact angle (°) |
|---|---|---|---|---|---|---|
| TC-1 | Polymer 1 (100) | 1.54 | 0 | 0 | 13 | 67 |
| TC-2 | Polymer 2 (100) | 1.54 | 0 | 0 | 11 | 76 |
| TC-3 | Polymer 3 (100) | 1.54 | 0 | 0 | 11 | 75 |
| TC-4 | Polymer 4 (100) | 1.54 | 0 | 0 | 10 | 76 |
| TC-5 | Polymer 5 (100) | 1.54 | 0 | 0 | 11 | 74 |
| TC-6 | Polymer 6 (100) | 1.54 | 0 | 0 | 10 | 78 |
| TC-7 | Polymer 7 (100) | 1.54 | 0 | 0 | 12 | 73 |
| TC-8 | Polymer 8 (100) | 1.54 | 0 | 0 | 13 | 70 |
| TC-9 | Polymer 9 (100) | 1.54 | 0 | 0 | 10 | 79 |
| TC-10 | Polymer 10 (100) | 1.54 | 0 | 0 | 10 | 79 |
| TC-11 | Polymer 11 (100) | 1.54 | 0 | 0 | 9 | 80 |
| TC-12 | Polymer 12 (100) | 1.54 | 0 | 0 | 10 | 78 |
| TC-13 | Polymer 13 (100) | 1.54 | 0 | 0 | 10 | 80 |
| TC-14 | Polymer 14 (100) | 1.54 | 0 | 0 | 10 | 77 |
| TC-15 | Polymer 15 (100) | 1.54 | 0 | 0 | 10 | 76 |
| TC-16 | Polymer 16 (100) | 1.54 | 0 | 0 | 10 | 77 |
| TC-17 | Polymer 17 (100) | 1.54 | 0 | 0 | 12 | 73 |
| TC-18 | Polymer 18 (100) | 1.54 | 0 | 0 | 12 | 74 |
| TC-19 | Polymer 19 (100) | 1.54 | 0 | 0 | 11 | 75 |
| TC-20 | Polymer 8 (75) Polymer 20 (25) | 1.54 | 0 | 0 | 12 | 69 |
| TC-21 | Polymer 9 (75) Polymer 20 (25) | 1.54 | 0 | 0 | 9 | 78 |
| TC-22 | Polymer 10 (75) Polymer 20 (25) | 1.54 | 0 | 0 | 9 | 78 |
| TC-23 | Polymer 11 (75) Polymer 20 (25) | 1.54 | 0 | 0 | 9 | 79 |
| TC-24 | Polymer 12 (75) Polymer 20 (25) | 1.54 | 0 | 0 | 9 | 77 |
| TC-25 | Polymer 14 (75) Polymer 20 (25) | 1.54 | 0 | 0 | 9 | 77 |
| TC-26 | Polymer 9 (75) Polymer 21 (25) | 1.54 | 0 | 0 | 9 | 80 |
| TC-27 | Polymer 9 (75) Polymer 22 (25) | 1.54 | 0 | 0 | 9 | 81 |
| Comparative TC-1 | Comparative Polymer 1 (100) | 1.54 | 0 | 0 | 15 | 69 |
| Comparative TC-2 | Comparative Polymer 1 (75) Polymer 20 (25) | 1.54 | 0 | 0 | 15 | 68 |

As seen from Table 6, the inventive polymers P1 have a greater receding contact angle than the comparative polymer. The value of receding contact angle differs little between a P1/P2 polymer blend and polymer P1 alone, demonstrating effective layer separation between polymers P1 and P2, that is, a layer of polymer P1 is disposed on top of a layer of polymer P2. In general, a smaller sliding angle indicates an easier flow of water on the protective coating; and a larger receding contact angle indicates that fewer liquid droplets are left during high-speed scan exposure. It is seen from Table 6 that the protective topcoats TC-1 to 27 within the scope of the invention are improved in sliding angle and ring contact angle over Comparative TC-1 to 2.

[Evaluation of Resist]

A resist solution was prepared by dissolving 5 g of Resist Polymer, 0.5 g of a photoacid generator PAG1, and 0.1 g of Quencher 1 (all shown below) in 100 g of PGMEA and filtering through a polypropylene filter having a pore size of 0.2 μm.

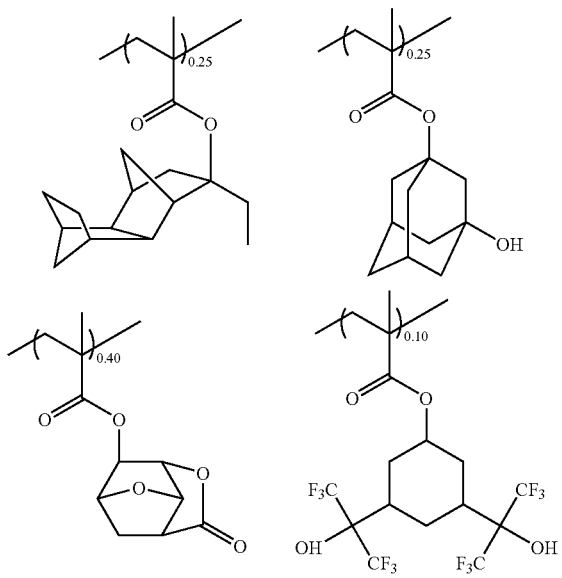

Resist Polymer: Mw = 7,600, Mw/Mn = 1.8

-continued

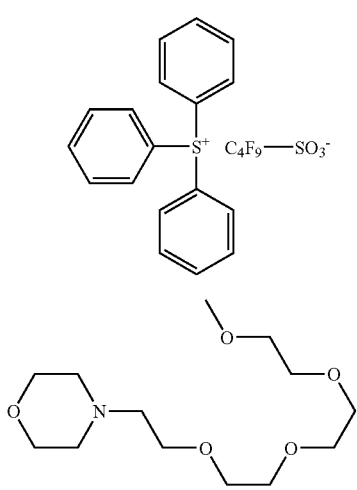

PAG 1

Quencher 1

An antireflective coating ARC-29A (Nissan Chemical Co., Ltd.) was deposited on a silicon substrate to a thickness of 87 nm. The resist solution was applied onto the ARC and baked at 105° C. for 60 seconds to form a resist film of 120 nm thick. The protective topcoat solution (prepared above) was applied onto the resist film and baked at 100° C. for 60 seconds. In order to simulate immersion lithography, light exposure was preceded by rinsing of the coating with pure water for 5 minutes. The structure was exposed by means of an ArF scanner model S307E (Nikon Corp., NA 0.85, a 0.93/0.62, 20° dipole illumination, 6% halftone phase shift mask), rinsed for 5 minutes while splashing pure water, post-exposure baked (PEB) at 100° C. for 60 seconds, and developed with a 2.38 wt % TMAH aqueous solution for 60 seconds. As a comparative run, a similar process including light exposure, water rinsing, PEB and development was carried out in the absence of the protective coating. The wafers were sectioned for comparing the profile of 65-nm line-and-space pattern and sensitivity. Further, 0.5 µl of water droplet was dropped on the resist film after development, and a contact angle at the interface between the resist and water droplet was measured. The results are shown in Table 7.

TABLE 7

| Resist protective topcoat | Sensitivity (mJ/cm$^2$) | 65-nm pattern profile | Contact angle with water after development (°) |
|---|---|---|---|
| TC-20 | 30 | rectangular | 60 |
| TC-21 | 29 | rectangular | 59 |
| TC-22 | 29 | rectangular | 60 |
| TC-23 | 30 | rectangular | 61 |
| TC-24 | 30 | rectangular | 61 |
| TC-25 | 30 | rectangular | 60 |
| TC-26 | 30 | rectangular | 60 |
| TC-27 | 30 | rectangular | 60 |
| Comparative TC-1 | 28 | rounded top | 68 |
| Comparative TC-2 | 29 | rounded top | 70 |
| no protective film | 30 | T-top | 62 |

When water rinsing was carried out after exposure in the absence of a protective topcoat, the resist pattern had a T-top profile. This is presumably because the acid generated was dissolved in water. In the presence of a protective topcoat according to the invention which had a large receding contact angle, the resist film had a reduced contact angle after development and produced a resist pattern of rectangular profile after development.

A protective topcoat of polymer P1 alone has a large receding contact angle, but provides a large contact angle with water after development. In contrast, a film of polymer P2 having a sulfonic acid amine salt is inferior in water repellency and water sliding property, but provides a small contact angle with water after development and a resist pattern of rectangular profile. A blend of polymer P1 with polymer P2 forms a protective topcoat which has a large receding contact angle and provides a small contact angle with water after development.

In a further run, some resist protective topcoat solutions (TC-21 and Comparative TC-2) used in the exposure experiment were precision filtered through a high-density polyethylene filter with a pore size of 0.02 µm. An antireflective coating ARC-29A (Nissan Chemical Co., Ltd.) of 87 nm thick was deposited on a 8-inch silicon substrate. The resist solution was applied onto the ARC and baked at 105° C. for 60 seconds to form a resist film of 120 nm thick. Each protective topcoat solution was coated thereon and baked at 100° C. for 60 seconds. Using an ArF scanner model S307E (Nikon Corp., NA 0.85, σ 0.93, Cr mask), the entire surface of the wafer was subjected to checkered-flag exposure including alternate exposure of open-frame exposed and unexposed portions having an area of 20 mm square. This was followed by post-exposure baking (PEB) and development with a 2.38 wt % TMAH aqueous solution for 60 seconds.

Using a flaw detector Win-Win 50-1200 (Tokyo Seimitsu Co., Ltd.), the number of defects in the unexposed portion of the checkered-flag was counted at the pixel size of 0.125 µm. Those defects on the resist surface in the unexposed portion are stain-like defects and classified as blob defects. The results are shown in Table 8. It is evident that the protective topcoat compositions comprising a blend of polymers P1 and P2 produce a dramatically reduced number of defects, as compared with the comparative protective topcoat composition.

TABLE 8

| Resist protective topcoat | Number of defects |
|---|---|
| TC-21 | 16 |
| Comparative TC-2 | 3,000 |

[EB Lithography]

In an EB image writing test, a positive resist material was prepared by dissolving 90 parts by weight of EB Polymer synthesized by radical polymerization, 10 parts by weight of PAG2, and 0.4 part by weight of Quencher 2 (all shown below) in 700 parts by weight of PGMEA and 300 parts by weight of ethyl lactate (EL) and filtering through a filter with a pore size of 0.2 µm.

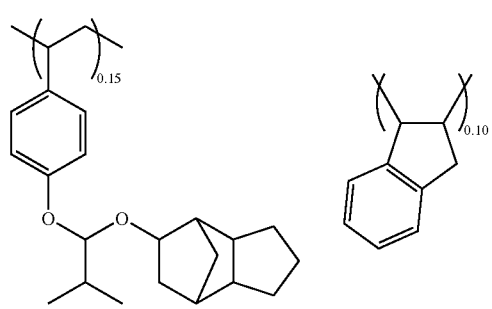

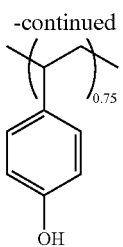

EB Polymer: Mw = 5,300, Mw/Mn = 1.6

PAG 2

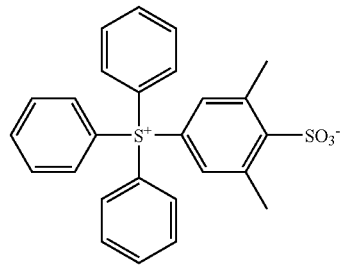

Quencher 2

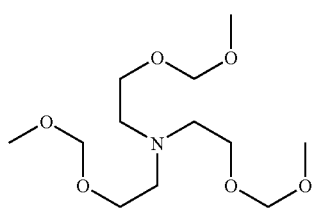

Using Clean Track Mark 5 (Tokyo Electron Ltd.), the positive resist material was spin coated on a silicon substrate with a diameter of 6 inches (150 mm) and prebaked on a hot plate at 110° C. for 60 seconds to form a resist film of 200 nm thick. A protective coating was coated thereon. Using HL-800D (Hitachi, Ltd.) at a HV voltage of 50 keV, imagewise exposure was performed on the wafer in a vacuum chamber. The wafer was then allowed to stand in the vacuum chamber for 20 hours, after which additional imagewise exposure was performed at a different area.

Using Clean Track Mark 5 (Tokyo Electron Ltd.), immediately after the imagewise exposure, the wafer was post-exposure baked (PEB) on a hot plate at 90° C. for 60 seconds and puddle developed in a 2.38 wt % TMAH aqueous solution for 30 seconds to form a positive pattern.

Using a measurement SEM S-7280 (Hitachi, Ltd.), a size change during the vacuum holding duration was determined. After an exposure dose which provided a 1:1 resolution at the top and bottom of a 0.12 μm line-and-space pattern was determined, a 0.12 μm line-and-space pattern at that exposure dose was measured for line width in both the initially exposed area and the 20 hour later exposed area. A difference therebetween is the size change. Positive values of size change indicate that the resist sensitivity varies toward a higher level during vacuum holding whereas negative values indicate that the sensitivity varies toward a lower level. The results are shown in Table 9.

TABLE 9

| Resist protective topcoat | Size change (nm) |
|---|---|
| TC-20 | 0 |
| TC-21 | −1 |
| TC-22 | 0 |

TABLE 9-continued

| Resist protective topcoat | Size change (nm) |
|---|---|
| TC-23 | 0 |
| TC-24 | −1 |
| TC-25 | −1 |
| TC-26 | 0 |
| TC-27 | 0 |
| TC-28 | 0 |
| no protective film | −9 |

In the EB imagewise exposure test, the application of inventive resist protective topcoats (TC-20 to 28) improved the stability of resist during post-exposure vacuum holding.

[Evaluation of Resist Composition]

A resist solution was prepared by dissolving 5 g of Resist Polymer, 0.25 g of an additive polymer selected from Polymers 8 to 19 and Comparative Polymer 1, 0.25 g of PAG1, and 0.05 g of Quencher 1 (all shown below) in 75 g of PGMEA and filtering through a polypropylene filter having a pore size of 0.2 μm. For comparative purposes, a resist solution was similarly prepared without adding the additive polymer.

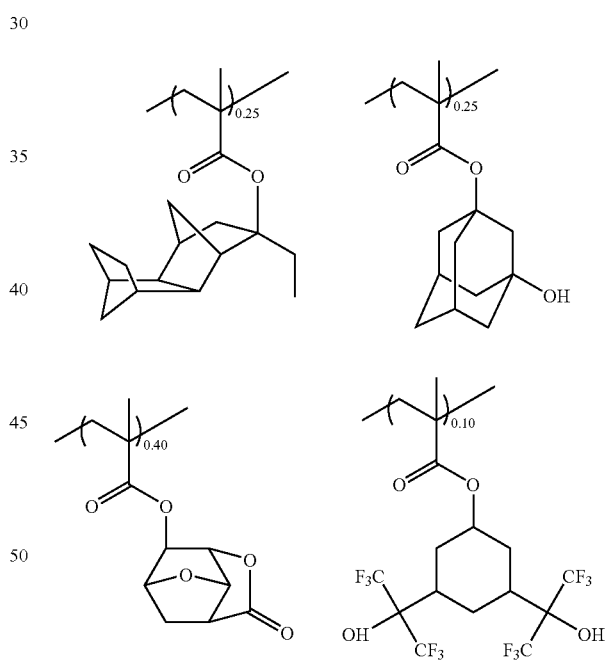

Resist Polymer: Mw = 7,600, Mw/Mn = 1.8

PAG 1

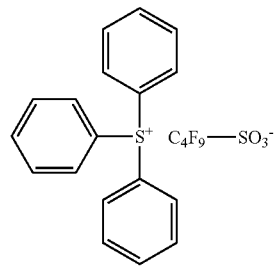

-continued

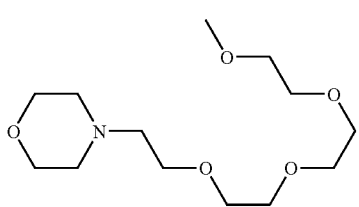
Quencher 1

An antireflective coating ARC-29A (Nissan Chemical Co., Ltd.) was deposited on a silicon substrate to a thickness of 87 nm. The resist solution was applied onto the ARC and baked at 120° C. for 60 seconds to form a resist film of 150 nm thick.

A contact angle with water of the resist film was measured, using an inclination contact angle meter Drop Master 500 by Kyowa Interface Science Co., Ltd. Specifically, the wafer covered with the resist film was kept horizontal, and 50 µL of pure water was dropped on the resist film to form a droplet. While the wafer was gradually inclined, the angle (sliding angle) at which the droplet started sliding down was determined as well as receding contact angle. The results are shown in Table 10.

TABLE 10

| Additive Polymer | Sliding angle (°) | Receding contact angle (°) | Anion leach-out (ppb) | Sensitivity (mJ/cm$^2$) | 75-nm pattern profile |
|---|---|---|---|---|---|
| Polymer 8 | 17 | 74 | 7 | 34 | rectangular |
| Polymer 9 | 11 | 84 | 6 | 35 | rectangular |
| Polymer 10 | 9 | 86 | 7 | 33 | rectangular |
| Polymer 11 | 9 | 87 | 6 | 34 | rectangular |
| Polymer 12 | 11 | 84 | 6 | 35 | rectangular |
| Polymer 13 | 8 | 87 | 7 | 32 | rectangular |
| Polymer 14 | 10 | 83 | 7 | 32 | rectangular |
| Polymer 15 | 12 | 74 | 6 | 33 | rectangular |
| Polymer 16 | 12 | 74 | 7 | 33 | rectangular |
| Polymer 17 | 14 | 73 | 6 | 32 | rectangular |
| Polymer 18 | 14 | 74 | 6 | 32 | rectangular |
| Polymer 19 | 13 | 75 | 7 | 33 | rectangular |
| Comparative Polymer 1 | 15 | 69 | 7 | 32 | rectangular |
| not added | 28 | 40 | 60 | 45 | T-top |

A smaller sliding angle indicates an easier flow of water on the resist film. A larger receding contact angle indicates that fewer liquid droplets are left during high-speed scan exposure. It is demonstrated in Table 10 that the inclusion of the additive polymer of the invention in a resist solution achieves a drastic improvement in the receding contact angle of photoresist film without adversely affecting the sliding angle, as compared with those photoresist films free of the additive polymer.

Also, the resist film-bearing wafer (prepared above) was irradiated through an open frame at an energy dose of 50 mJ/cm$^2$ using an ArF scanner S305B (Nikon Corp.). Then a true circle ring of Teflon® having an inner diameter of 10 cm was placed on the resist film, 10 mL of pure water was carefully injected inside the ring, and the resist film was kept in contact with water at room temperature for 60 seconds. Thereafter, the water was recovered, and a concentration of photoacid generator (PAG1) anion in the water was measured by an LC-MS analyzer (Agilent). The anion concentration measured indicates an amount of anions leached out for 60 seconds. The results are also shown in Table 10. It is evident from Table 10 that a photoresist film formed from a resist solution containing the inventive polymer is effective in inhibiting the PAG from being leached out of the film in water.

Further, the resist film-bearing wafer (prepared above) was exposed by means of an ArF scanner model S307E (Nikon Corp., NA 0.85, σ 0.93, 4/5 annular illumination, 6% halftone phase shift mask), rinsed for 5 minutes while splashing pure water, post-exposure baked (PEB) at 110° C. for 60 seconds, and developed with a 2.38 wt % TMAH aqueous solution for 60 seconds, forming a 75-nm line-and-space pattern. The wafer was sectioned, and the profile and sensitivity of the 75-nm line-and-space pattern were evaluated. The results are also shown in Table 10.

As seen from Table 10, when exposure is followed by water rinsing, the resist film having the additive polymer of the invention formulated therein formed a pattern of rectangular profile, in stark contrast with the resist film free of the additive polymer of the invention forming a pattern of T-top profile.

Japanese Patent Application Nos. 2008-279212, 2008-279224 and 2008-279231 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer comprising recurring units of he general formula (6) and having a weight average molecular weight of 1,000 to 500,000,

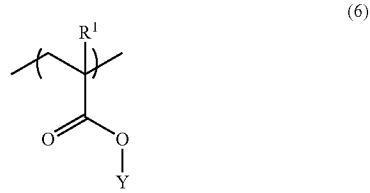
(6)

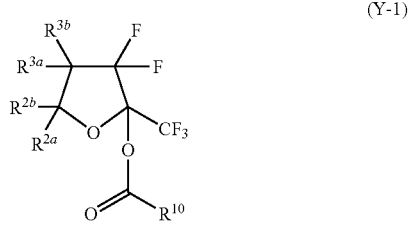
(Y-1)

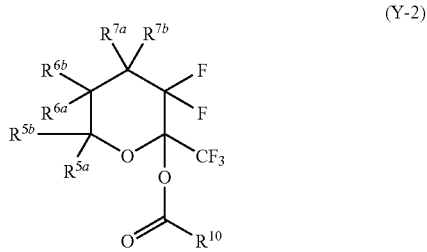
(Y-2)

(Y-3)

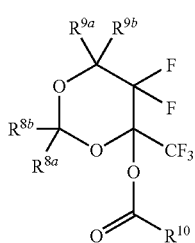

(8b)

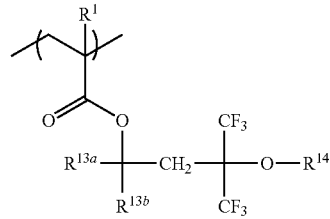

wherein $R^1$ is hydrogen, methyl or trifluoromethyl, and Y is a structure having the general formula (Y-1), (Y-2) or (Y-3), in formula (Y-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (Y-1) is linked to the —(C=O)—O— linkage in recurring unit (6) via any one of $R^{2a}$, $R^{2b}$, $R^{3a}$, and $R^{3b}$, in formula (Y-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Y-2) is linked to the —(C=O)—O— linkage in recurring unit (6) via any one of $R^{5a}$, $R^{5b}$, $R^{6a}$, $R^{6b}$, $R^{7a}$, and $R^{7b}$, in formula (Y-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Y-3) is linked to the —(C=O)—O— linkage in recurring unit (6) via any one of $R^{8a}$, $R^{8b}$, $R^{9a}$, and $R^{9b}$, and $R^{10}$ is a straight, branched or cyclic $C_1$-$C_{19}$ alkyl group in which at least one hydrogen atom may be substituted by a halogen atom or at least one methylene moiety may be substituted by an oxygen atom or carbonyl group, with the proviso that when the structure (Y-1), (Y-2) or (Y-3) is linked to the —(C=O)—O—linkage in recurring unit (6) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

2. The polymer of claim 1, further comprising recurring units of one or more type selected from the general formulae (8a) to (8f):

(8a)

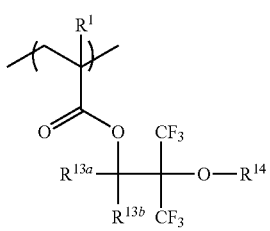

(8c)

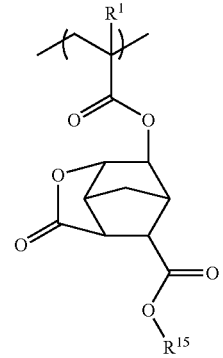

(8d)

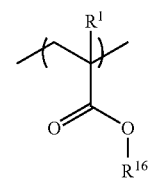

(8e)

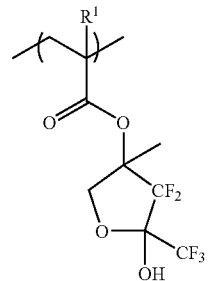

(8f)

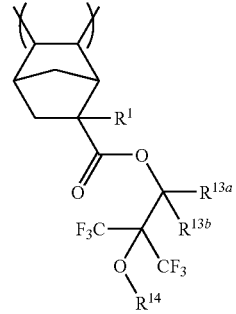

wherein $R^1$ is hydrogen, methyl or trifluoromethyl, $R^{13a}$ and $R^{13b}$ each are hydrogen or a straight, branched or cyclic $C_1$-$C_{15}$ alkyl group, or $R^{13a}$ and $R^{13b}$ may bond together to form a ring with the carbon atom to which they are attached, $R^{14}$ is hydrogen, a straight, branched or cyclic $C_1$-$C_{15}$ alkyl or fluoroalkyl group, or an acid labile group, $R^{15}$ is a straight, branched or cyclic $C_1$-$C_{15}$ fluoroalkyl group, and $R^{16}$ is an acid labile group.

3. A resist protective coating composition comprising a polymer comprising recurring units of the general formula (6):

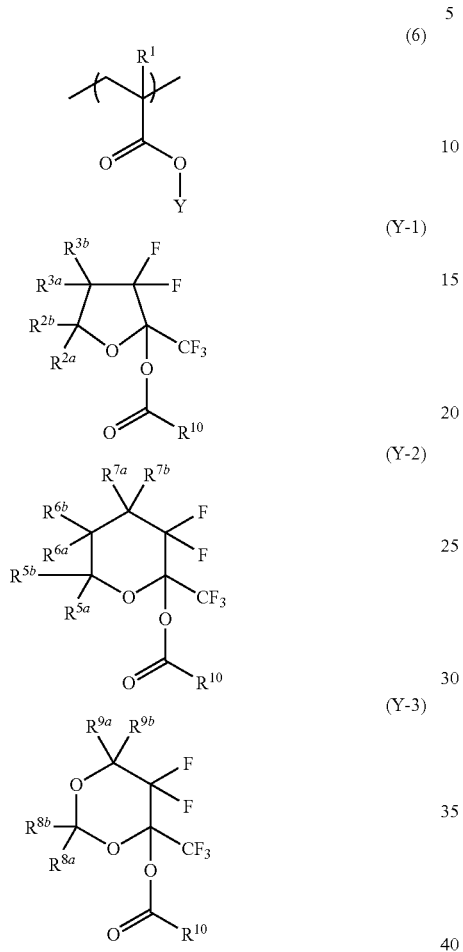

wherein $R^1$ is hydrogen, methyl or trifluoromethyl, and Y is a structure having the general formula (Y-1), (Y-2) or (Y-3),
  in formula (Y-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (Y-1) is linked to the —(C=O)—O— linkage in recurring unit (6) via any one of $R^{2a}$, $R^{2b}$, $R^{3a}$, and $R^{3b}$,
  in formula (Y-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Y-2) is linked to the —(C=O)—O— linkage in recurring unit (6) via any one of $R^{5a}$, $R^{5b}$, $R^{6a}$, $R^{6b}$, $R^{7a}$, and $R^{7b}$,
  in formula (Y-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Y-3) is linked to the —(C=O)—O— linkage in recurring unit (6) via any one of $R^{8a}$, $R^{8b}$, $R^{9a}$, and $R^{9b}$, and
  $R^{10}$ is a straight, branched or cyclic $C_1$-$C_{19}$ alkyl group in which at least one hydrogen atom may be substituted by a halogen atom or at least one methylene moiety may be substituted by an oxygen atom or carbonyl group,
  with the proviso that when the structure (Y-1), (Y-2) or (Y-3) is linked to the —(C=O)—O— linkage in recurring unit (6) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

4. The resist protective coating composition of claim 3 wherein said polymer further comprises recurring units of one or more type selected from the general formulae (8a) to (8f):

-continued

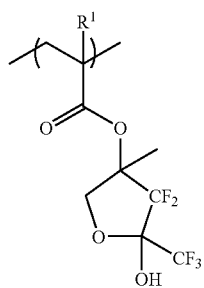

(8e)

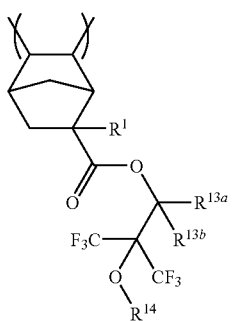

(8f)

wherein $R^1$ is hydrogen, methyl or trifluoromethyl, $R^{13a}$ and $R^{13b}$ each are hydrogen or a straight, branched or cyclic $C_1$-$C_{15}$ alkyl group, or $R^{13a}$ and $R^{13b}$ may bond together to form a ring with the carbon atom to which they are attached, $R^{14}$ is hydrogen, a straight, branched or cyclic $C_1$-$C_{15}$ alkyl or fluoroalkyl group, or an acid labile group, $R^{15}$ is a straight, branched or cyclic $C_1$-$C_{15}$ fluoroalkyl group, and $R^{16}$ is an acid labile group.

5. The protective coating composition of claim 3, further comprising a second polymer comprising recurring units of the general formula (9) or (10):

(9)

(10)

wherein $R^{31a}$ and $R^{31b}$ are hydrogen or methyl, $R^{32}$ is a single bond, $C_1$-$C_4$ alkylene, phenylene, —C(=O)—O—, or —C(=O)—NH—, $R^{33}$ is a single bond or a straight, branched or cyclic $C_1$-$C_8$ alkylene group, $R^{34a}$ to $R^{34d}$ and $R^{36a}$ to $R^{36c}$ are each independently hydrogen, a straight, branched or cyclic $C_1$-$C_{12}$ alkyl, alkenyl, oxoalkyl or oxoalkenyl group, $C_6$-$C_{20}$ aryl group, or $C_7$-$C_{12}$ aralkyl or aryloxoalkyl group, in which some or all hydrogen atoms may be substituted by alkoxy groups, $R^{34a}$ to $R^{34d}$ and $R^{36a}$ to $R^{36c}$ may contain a nitrogen atom, ether group, ester group, hydroxyl group or carboxyl group therein, any two of $R^{34a}$ to $R^{34d}$ and $R^{36a}$ to $R^{36c}$ may bond together to form a ring with the nitrogen atom to which they are attached, and when they form a ring, they are each independently a $C_3$-$C_{15}$ alkylene or a hetero-aromatic ring having the nitrogen atom therein, $R^{35}$ is a straight, branched or cyclic $C_1$-$C_8$ alkylene group, and $R^{37}$ is a straight, branched or cyclic $C_1$-$C_{20}$ alkyl group which may contain carbonyl, ester, ether or halogen, or a $C_6$-$C_{15}$ aryl group which may contain carbonyl, ester, ether, halogen, or $C_1$-$C_{15}$ alkyl or fluoroalkyl.

6. The protective coating composition of claim 5, wherein the second polymer further comprises recurring units of the general formula (11):

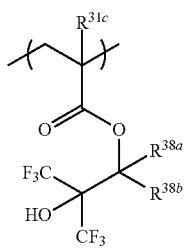

(11)

wherein $R^{31c}$ is hydrogen or methyl, $R^{38a}$ and $R^{38b}$ are hydrogen or a straight, branched or cyclic $C_1$-$C_{15}$ alkyl group, or $R^{38a}$ and $R^{38b}$ may bond together to form a ring with the carbon atom to which they are attached.

7. A resist protective coating composition comprising a polymer comprising recurring units of the general formula (5) and a second polymer comprising recurring units of the general formula (9) or (10):

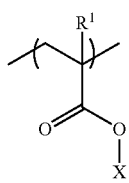

(5)

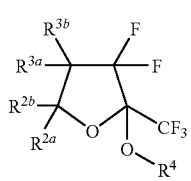

(X-1)

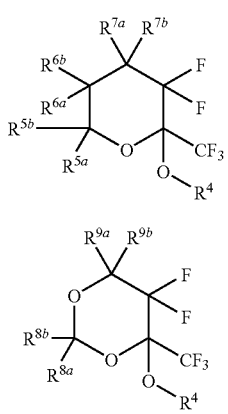

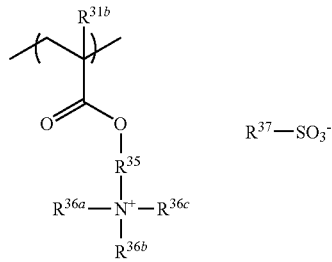

wherein $R^{31a}$ and $R^{31b}$ are hydrogen or methyl, $R^{32}$ is a single bond, $C_1$-$C_4$ alkylene, phenylene, —C(=O)—O—, or —C(=O)—NH—, $R^{33}$ is a single bond or a straight, branched or cyclic $C_1$-$C_8$ alkylene group, $R^{34a}$ to $R^{34d}$ and $R^{36a}$ to $R^{36c}$ are each independently hydrogen, straight, branched or cyclic $C_1$-$C_{12}$ alkyl, alkenyl, oxoalkyl or oxoalkenyl group, $C_6$-$C_{20}$ aryl group, or $C_7$-$C_{12}$ aralkyl or aryloxoalkyl group, in which some or all hydrogen atoms may be substituted by alkoxy groups, $R^{34a}$ to $R^{34d}$ and $R^{36a}$ to $R^{36c}$ may contain a nitrogen atom, ether group, ester group, hydroxyl group or carboxyl group therein, any two of $R^{34a}$ to $R^{34d}$ and $R^{36a}$ to $R^{36c}$ may bond together to form a ring with the nitrogen atom to which they are attached, and when they form a ring, they are each independently a $C_3$-$C_{15}$ alkylene or a hetero-aromatic ring having the nitrogen atom therein, $R^{35}$ is a straight, branched or cyclic $C_1$-$C_8$ alkylene group, and $R^{37}$ is a straight, branched or cyclic $C_1$-$C_{20}$ alkyl group which may contain carbonyl, ester, ether or halogen, or a $C_6$-$C_{15}$ aryl group which may contain carbonyl, ester, ether, halogen, or $C_1$-$C_{15}$ alkyl or fluoroalkyl.

8. The protective coating composition of claim 7, wherein the second polymer further comprises rurring units of the general formula (11):

wherein $R^1$ is hydrogen, methyl or trifluoromethyl, and X is a structure having the general formula (X-1), (X-2) or (X-3), in formula (X-1) $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (X-1) is linked to the —(C=O)—O— linkage in recurring unit (5) via any one of $R^{2a}$, $R^{2b}$, $R^{3a}$, and $R^{3b}$, in formula (X-2), $R^{5a}$, $R^{5b}$, $R^{6a}$, $R^{6b}$, $R^{7a}$, are $R^{7b}$ each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (X-2) is linked to the —(C=O)—O— linkage in recurring unit (5) via any one of $R^{5a}$, $R^{5b}$, $R^{6a}$, $R^{6b}$, $R^{7a}$, and $R^{7b}$, in formula (X-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R_{8a}$, $R^{8b}$, $R^{9a}$, and $R^{9b}$ may bond together to form a ring with the carbon atom to which they are attached, the structure (X-3) is linked to the —(C=O)—O— linkage in recurring unit (5) via any one of $R^{8a}$, $R^{8b}$, $R^{9a}$, and $R^{9b}$, $R^4$ is a straight, branched or cyclic $C_1$-$C_{20}$ alkyl group in which at least one hydrogen atom may be substituted by a halogen atom or at least one methylene moiety may be substituted by an oxygen atom or carbonyl group, with the proviso that when the structure (X-1), (X-2) or (X-3) is linked to the —(C=O)—O— linkage in recurring unit (5) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom,

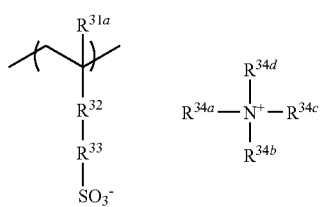

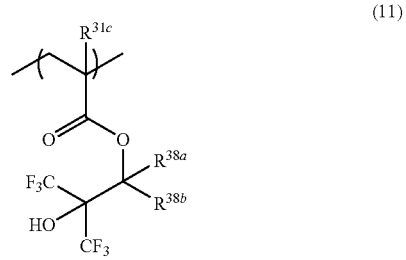

wherein $R^{31c}$ is hydrogen or methyl, $R^{38a}$ and $R^{38b}$ are hydrogen or a straight, branched or cyclic $C_1$-$C_{15}$ alkyl group, or $R^{38a}$ and $R^{38b}$ may bond together to form a ring with the carbon atom to which they are attached.

9. A resist protective coating composition comprising a polymer comprising recurring units of the general formula (5) and an ether compound of 8 to 12 carbon atoms as a solvent:

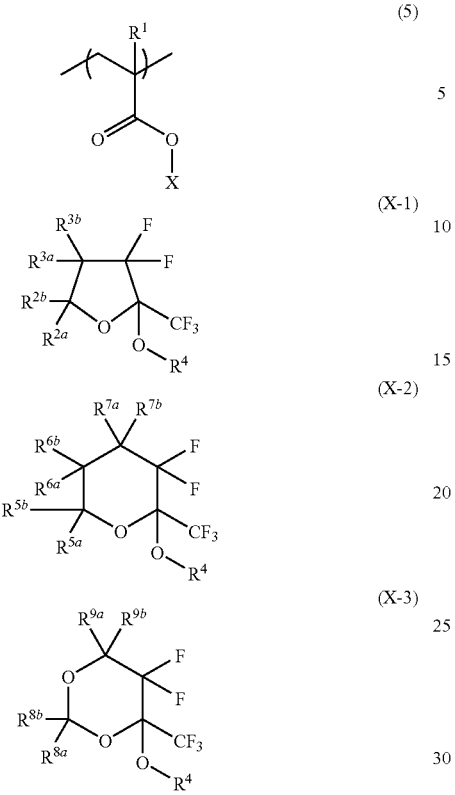

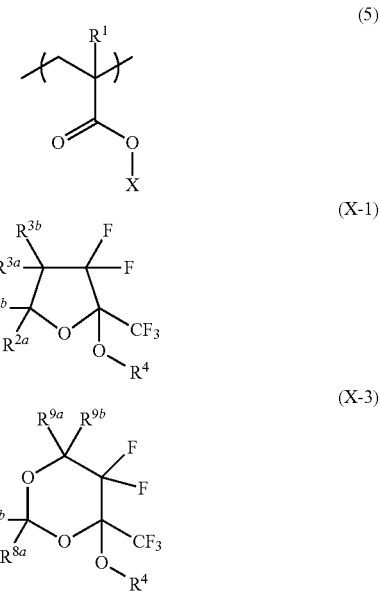

wherein $R^1$ is hydrogen, methyl or trifluoromethyl, and X is a structure having the general formula (X-1), (X-2) or (X-3), in formula (X-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (X-1) is linked to the —(C=O)—O— linkage in recurring unit (5) via any one of $R^{2a}$, $R^{2b}$, $R^{3a}$, and $R^{3b}$, in formula (X-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (X-2) is linked to the —(C=O)—O— linkage in recurring unit (5) via any one of $R^{5a}$, $R^{5b}$, $R^{6a}$, $R^{6b}$, $R^{7a}$, and $R^{7b}$, in formula (X-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (X-3) is linked to the —(C=O)—O— linkage in recurring unit (5) via any one of $R^{8a}$, $R^{8b}$, $R^{9a}$, and $R^{9b}$, $R^4$ is a straight, branched or cyclic $C_1$-$C_{20}$ alkyl group in which at least one hydrogen atom may be substituted by a halogen atom or at least one methylene moiety may be substituted by an oxygen atom or carbonyl group, with the proviso that when the structure (X-1), (X-2) or (X-3) is linked to the —(C=O)—O— linkage in recurring unit (5) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

10. The protective coating composition of claim 9 wherein the solvent comprises at least one ether compound of 8 to 12 carbon atoms selected from the group consisting of di-n-butyl ether, diisobutyl ether, di-sec-butyl ether, di-n-pentyl ether, diisopentyl ether, di-sec-pentyl ether, di-t-amyl ether, and di-n-hexyl ether.

11. The protective coating composition of claim 9 wherein the solvent comprises a mixture of the ether compound and 0.1 to 90% by weight of an alcohol of 4 to 10 carbon atoms.

12. A pattern forming process comprising the steps of (1) applying a resist material onto a substrate to form a photoresist film, (2) applying a resist protective coating composition onto the photoresist film to form a protective coating thereon, (3) heat treating and exposing the coated substrate to high-energy radiation from a projection lens through a photomask while holding a liquid between the substrate and the projection lens, and (4) developing with a developer, said resist protective coating composition comprising a polymer comprising recurring units of the general formula (5):

wherein $R^1$ is hydrogen, methyl or trifluoromethyl, and X is a structure having the general formula (X-1) or (X-3), in formula (X-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (X-1) is linked to the —(C=O)—O— linkage in recurring unit (5) via any one of $R^{2a}$, $R^{2b}$, $R^{3a}$, and $R^{3b}$, in formula (X-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (X-3) is linked to the —(C=O)—O— linkage in recurring unit (5) via any one of $R^{8a}$, $R^{8b}$, $R^{9a}$, and $R^{9b}$, $R^4$ is a straight, branched or cyclic $C_1$-$C_{20}$ alkyl group in which at least one hydrogen atom may be substituted by a halogen atom or at least one methylene moiety may be substituted by an oxygen atom or carbonyl group, with the proviso that when the structure (X-1) or (X-3) is linked to the —(C=O)—O— linkage in recurring unit (5) via a linking group which is any one of $R^{2a}$, $R^{2b}$, $R^{3a}$, $R^{3b}$, $R^{8a}$, $R^{8b}$, $R^{9a}$, and $R^{9b}$, the linking group is an organic group as defined above, but having a valence bond as a result of one hydrogen atom being eliminated therefrom.

13. The process of claim 12 wherein the liquid is water.

14. The process of claim 12 wherein the high-energy radiation has a wavelength in the range of 180 to 250 nm.

15. The process of claim 12 wherein the developing step uses a liquid alkaline developer for thereby developing the photoresist film to form a resist pattern and stripping the resist protective coating therefrom at the same time.

16. A lithography process for forming a pattern, comprising the steps of forming a protective coating on a photoresist layer disposed on a mask blank, exposing the layer structure in vacuum to electron beam, and developing, the protective coating being formed of a protective coating composition comprising a polymer comprising recurring units of the general formula (5):

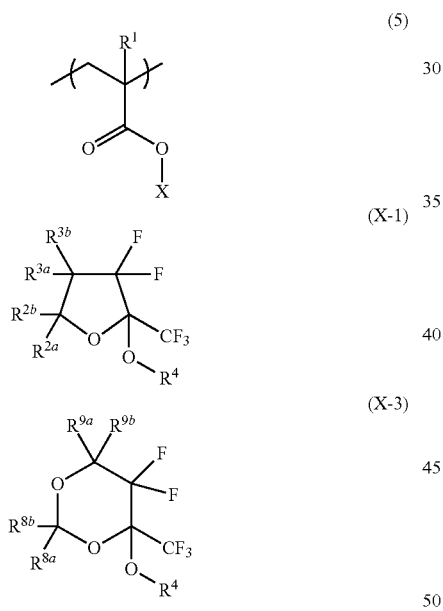

wherein $R^1$ is hydrogen, methyl or trifluoromethyl, and X is a structure having the general formula (X-1) or (X-3), in formula (X-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (X-1) is linked to the —(C=O)—O— linkage in recurring unit (5) via any one of $R^{2a}$, $R^{2b}$, $R^{3a}$, and $R^{3b}$, in formula (X-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (X-3) is linked to the —(C=O)—O— linkage in recurring unit (5) via any one of $R^{8a}$, $R^{8b}$, $R^{9a}$, and $R^{9b}$, $R^4$ is a straight, branched or cyclic $C_1$-$C_{20}$ alkyl group in which at least one hydrogen atom may be substituted by a halogen atom or at least one methylene moiety may be substituted by an oxygen atom or carbonyl group, with the proviso that when the structure (X-1) or (X-3) is linked to the —(C=O)—O— linkage in recurring unit (5) via a linking group which is any one of $R^{2a}$, $R^{2b}$, $R^{3a}$, $R^{3b}$, $R^{8a}$, $R^{8b}$, $R^{9a}$, and $R^{9b}$, the linking group is an organic group as defined above, but having a valence bond as a result of one hydrogen atom being eliminated therefrom.

17. A resist composition comprising (A) a polymer comprising recurring units of the general formula (6), (B) a base polymer having a structure derived from lactone ring, hydroxyl group and/or maleic anhydride, said base polymer becoming soluble in alkaline developer under the action of acid, (C) a compound capable of generating an acid upon exposure to high-energy radiation, and (D) an organic solvent,

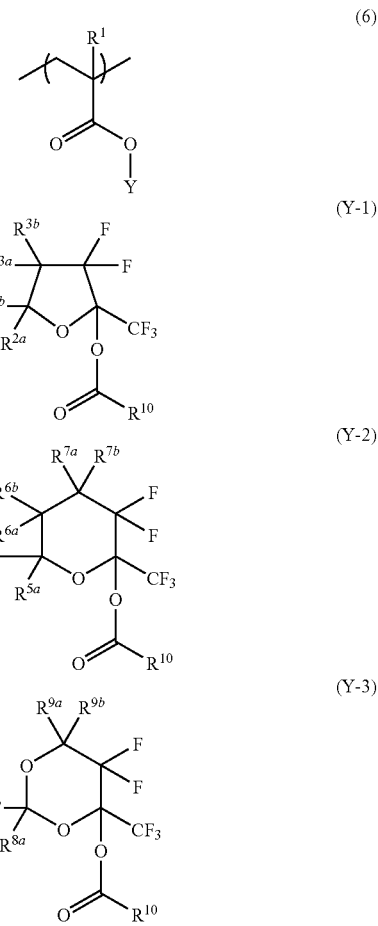

wherein $R^1$ is hydrogen, methyl or trifluoromethyl, and Y is a structure having the general formula (Y-1), (Y-2) or (Y-3), in formula (Y-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (Y-1) is linked to the —(C=O)—O— linkage in recurring unit (6) via any one of $R^{2a}$, $R^{2b}$, $R^{3a}$, and $R^{3b}$, in formula (Y-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Y-2) is linked to the —(C=O)—O— linkage in recurring unit (6) via any one of $R^{5a}$, $R^{5b}$, $R^{6a}$, $R^{6b}$, $R^{7a}$, and $R^{7b}$, in formula (Y-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Y-3) is linked to the —(C=O)—O— linkage in recurring unit (6) via any one of $R^{8a}$, $R^{8b}$, $R^{9a}$, and $R^{9b}$, and $R^{10}$ is a straight, branched or cyclic $C_1$-$C_{19}$ alkyl group in which at least one hydrogen atom may be substituted by a halogen atom or at least one methylene moiety may be substituted by an oxygen atom or carbonyl group, with the proviso that when the structure (Y-1), (Y-2) or (Y-3) is linked to the —(C=O)—O— linkage in recurring unit (6) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

18. The resist composition of claim 17 wherein said polymer (A) comprises recurring units as set forth in claim 17, and further recurring units of one or more type selected from the general formulae (8a) to (8f):

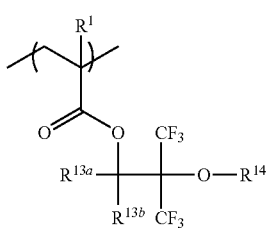
(8a)

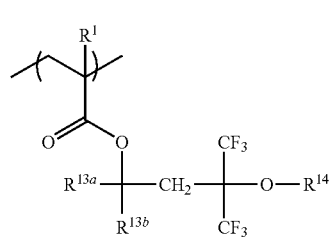
(8b)

-continued

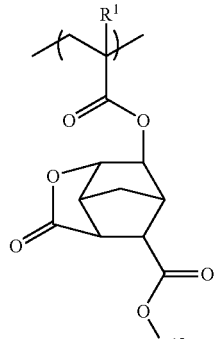
(8c)

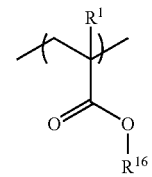
(8d)

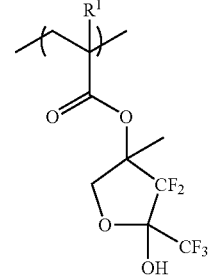
(8e)

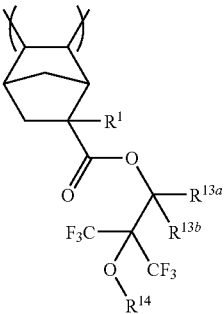
(8f)

wherein $R^1$ is hydrogen, methyl or trifluoromethyl, $R^{13a}$ and $R^{13b}$ each are hydrogen or a straight, branched or cyclic $C_1$-$C_{15}$ alkyl group, or $R^{13a}$ and $R^{13b}$ may bond together to form a ring with the carbon atom to which they are attached, $R^{14}$ is hydrogen, a straight, branched or cyclic $C_1$-$C_{15}$ alkyl or fluoroalkyl group, or an acid labile group, $R^{15}$ is a straight, branched or cyclic $C_1$-$C_{15}$ fluoroalkyl group, and $R^{16}$ is an acid labile group.

19. A pattern forming process comprising the steps of:
(1) applying the resist composition of claim 17 onto a substrate to form a resist film,
(2) heat treating the resist film and exposing it to high-energy radiation through a photomask, and
(3) developing the exposed resist film with a developer.

20. A pattern forming process comprising the steps of:
(1) applying the resist composition of claim 17 onto a substrate to form a resist film, (2) heat treating the coated substrate, and exposing it to high-energy radiation through a photomask while keeping a liquid between a projection lens and the coated substrate, and (3) developing the exposed resist film with a developer.

21. A pattern forming process comprising the steps of:
(1) applying the resist composition of claim 17 onto a substrate to form a resist film,
(2) forming a protective coating on the resist film,
(3) heat treating the coated substrate, and exposing it to high-energy radiation through a photomask while keeping a liquid between a projection lens and the coated substrate, and
(4) developing the exposed resist film with a developer.

22. A pattern forming process comprising the steps of:
(1) applying the resist composition of claim 17 onto a mask blank substrate to form a coating,
(2) heat treating the coating and irradiating it in vacuum with an electron beam, and
(3) developing the coating with a developer.

23. A resist protective coating composition comprising a polymer comprising recurring units of the general formula (7) and a second polymer comprising recurring units of the general formula (9) or (10):

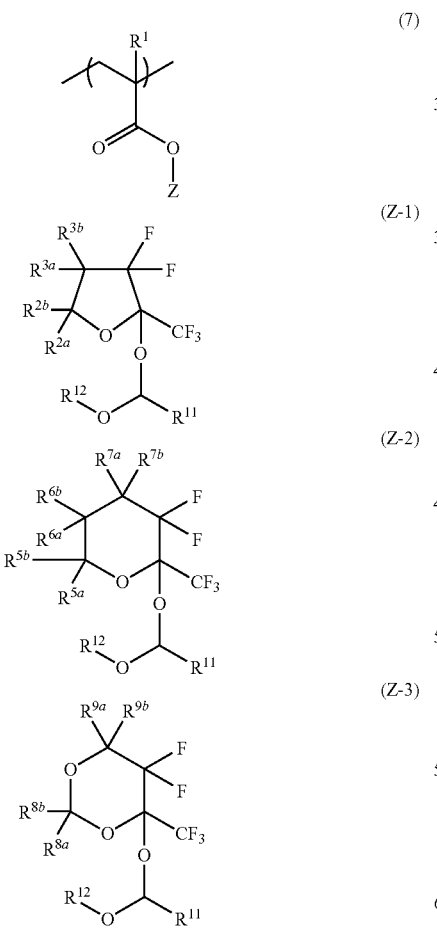

wherein $R^1$ is hydrogen, methyl or trifluoromethyl, and Z is a structure having the general formula (Z-1), (Z-2) or (Z-3),
in formula (Z-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$) may bond together to form a ring with the carbon atom to which they are attached, the structure (Z-1) is linked to the —(C=O)—O— linkage in recurring unit (7) via any one of $R^{2a}$, $R^{2b}$, $R^{3a}$, and $R^{3b}$, in formula (Z-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Z-2) is linked to the —(C=O)—O— linkage in recurring unit (7) via any one of $R^{5a}$, $R^{5b}$, $R^{6a}$, $R^{6b}$, $R^{7a}$, and $R^{7b}$, in formula (Z-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Z-3) is linked to the —(C=O)—O— linkage in recurring unit (7) via any one of $R^{8a}$, $R^{8b}$, $R^{9a}$, and $R^{9b}$, $R^{11}$ is hydrogen or a straight, branched or cyclic $C_1$-$C_{18}$ alkyl group in which at least one hydrogen atom may be substituted by a halogen atom or at least one methylene moiety may be substituted by an oxygen atom or carbonyl group, $R^{12}$ is a straight, branched or cyclic $C_1$-$C_{19}$ alkyl group in which at least one hydrogen atom may be substituted by a halogen atom or at least one methylene moiety may be substituted by an oxygen atom or carbonyl group, or $R^{11}$ and $R^{12}$ may bond together to form a cyclic structure with the carbon and oxygen atoms to which they are attached, with the proviso that when the structure (Z-1), (Z-2) or (Z-3) is linked to the —(C=O)—O— linkage in recurring unit (7) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$ the linking group is an organic group as defined above, but having a valence bond as a result of one hydrogen atom being eliminated therefrom,

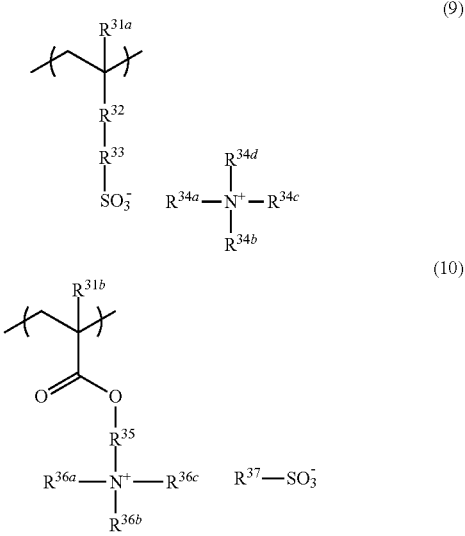

wherein $R^{31a}$ and $R^{31b}$ are hydrogen or methyl,
$R^{32}$ is a single bond, $C_1$-$C_4$ alkylene, phenylene, —C(=O)—O— or —C(=O)—NH—, $R^{33}$ is a single bond or a straight, branched or cyclic $C_1$-$C_8$ alkylene group, $R^{34a}$ to $R^{34d}$ and $R^{36a}$ to $R^{36c}$ are each independently hydrogen, a straight, branched or cyclic $C_1$-$C_{12}$ alkyl, alkenyl, oxoalkyl or oxoalkenyl group, $C_6$-$C_{20}$ aryl group, or $C_7$-$C_{12}$ aralkyl or aryloxoalkyl group, in which some or all hydrogen atoms may be substituted by alkoxy groups, $R^{34a}$ to $R^{34d}$ and $R^{36a}$ to $R^{36c}$ may contain a nitrogen atom, ether group, ester group, hydroxyl group or carboxyl group therein, any two of $R^{34a}$ to $R^{34d}$ and $R^{36a}$ to $R^{36c}$ may bond together to form a ring with the nitrogen atom to which they are attached, and when they form a ring, they are each independently a $C_3$-$C_{15}$ alkylene or a hetero-aromatic ring having the nitrogen atom therein, $R^{35}$ is a straight, branched or cyclic $C_1$-$C_8$ alkylene group, and $R^{37}$ is a straight, branched or cyclic $C_1$-$C_{20}$ alkyl group which may contain carbonyl, ester, ether or halogen, or a $C_6$-$C_{15}$ aryl group which may contain carbonyl, ester, ether, halogen, or $C_1$-$C_{15}$ alkyl or fluoroalkyl.

24. The protective coating composition of claim 23, wherein the second polymer further comprises recurring units of the general formula (11):

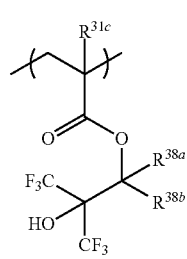

(11)

wherein $R^{31c}$ is hydrogen or methyl, $R^{38a}$ and $R^{38b}$ are hydrogen or a straight, branched or cyclic $C_1$-$C_{15}$ alkyl group, or $R^{38a}$ and $R^{38b}$ may bond together to form a ring with the carbon atom to which they are attached.

25. A resist protective coating composition comprising a polymer comprising recurring units of the general formula (6) and an ether compound of 8 to 12 carbon atoms as a solvent:

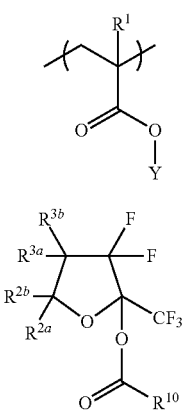

(6)

(Y-1)

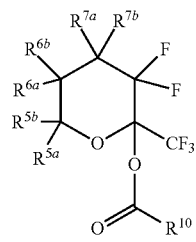

(Y-2)

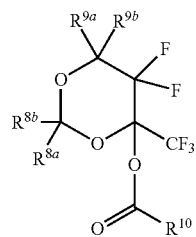

(Y-3)

wherein $R^1$ is hydrogen, methyl or trifluoromethyl, and Y is a structure having the general formula (Y-1), (Y-2) or (Y-3), in formula (Y-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (Y-1) is linked to the —(C=O)—O— linkage in recurring unit (6) via any one of $R^{2a}$, $R^{2b}$, $R^{3a}$, and $R^{3b}$, in formula (Y-2), and $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Y-2) is linked to the —(C=O)—O— linkage in recurring unit (6) via any one of $R^{5a}$, $R^{5b}$, $R^{6a}$, $R^{6b}$, $R^{7a}$, and $R^{7b}$, in formula (Y-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Y-3) is linked to the —(C=O)—O— linkage in recurring unit (6) via any one of $R^{8a}$, $R^{8b}$, $R^{9a}$, and $R^{9b}$, and $R^{10}$ is a straight, branched or cyclic $C_1$-$C_{19}$ alkyl group in which at least one hydrogen atom may be substituted by a halogen atom or at least one methylene moiety may be substituted by an oxygen atom or carbonyl group, with the proviso that when the structure (Y-1), (Y-2) or (Y-3) is linked to the —(C=O)—O— linkage in recurring unit (6) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

26. The protective coating composition of claim 25 wherein the solvent comprises a mixture of the ether compound and 0.1 to 90% by weight of an alcohol of 4 to 10 carbon atoms.

27. A resist protective coating composition comprising a polymer comprising recurring units of the general formula (7) and an ether compound of 8 to 12 carbon atoms as a solvent:

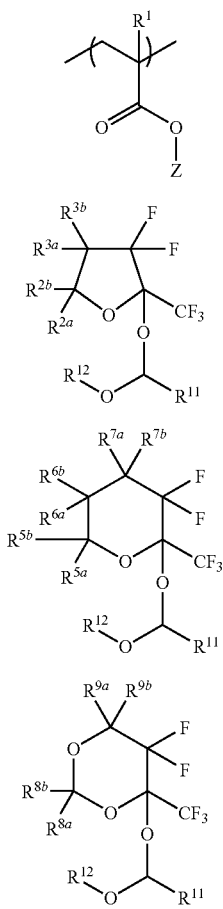

wherein $R^1$ is hydrogen, methyl or trifluoromethyl, and Z is a structure having the general formula (Z-1), (Z-2) or (Z-3), in formula (Z-1), $R^{2a}$, $R^{2b}$, $R^{3a}$, and $R^{3b}$ are each independently a single bond, hydrogen, hydroxyl, halogen, or a straight, branched or cyclic monovalent $C_1$-$C_{15}$ organic group, or any two of $R^{2a}$, $R^{2b}$, $R^{3a}$, and $R^{3b}$ may bond together to form a ring with the carbon atom to which they are attached, the structure (Z-1) is linked to the —(C=O)—O— linkage in recurring unit (7) via any one of $R^{2a}$, $R^{2b}$, $R^{3a}$, and $R^{3b}$, in formula (Z-2), $R^{5a}$, $R^{5b}$, $R^{6a}$, $R^{6b}$, $R^{7a}$, and $R^{7b}$ are each independently a single bond, hydrogen, hydroxyl, halogen, or a straight, branched or cyclic monovalent $C_1$-$C_{15}$ organic group, or any two of $R^{5a}$, $R^{5b}$, $R^{6a}$, $R^{6b}$, $R^{7a}$, and $R^{7b}$ may bond together to form a ring with the carbon atom to which they are attached, the structure (Z-2) is linked to the —(C=O)—O— linkage in recurring unit (7) via any one of $R^{5a}$, $R^{5b}$, $R^{6a}$, $R^{6b}$, $R^{7a}$, and $R^{7b}$, in formula (Z-3), $R^{8a}$, $R^{8b}$, $R^{9a}$, and $R^{9b}$ are each independently a single bond, hydrogen, hydroxyl, halogen, or a straight, branched or cyclic monovalent $C_1$-$C_{15}$ organic group, or any two of $R^{8a}$, $R^{8b}$, $R^{9a}$, and $R^{9b}$ may bond together to form a ring with the carbon atom to which they are attached, the structure (Z-3) is linked to the —(C=O)—O— linkage in recurring unit (7) via any one of $R^{8a}$, $R^{8b}$, $R^{9a}$, and $R^{9b}$, $R^{11}$ is hydrogen or a straight, branched or cyclic $C_1$-$C_{18}$ alkyl group in which at least one hydrogen atom may be substituted by a halogen atom or at least one methylene moiety may be substituted by an oxygen atom or carbonyl group, $R^{12}$ is a straight, branched or cyclic $C_1$-$C_{19}$ alkyl group in which at least one hydrogen atom may be substituted by a halogen atom or at least one methylene moiety may be substituted by an oxygen atom or carbonyl group, or $R^{11}$ and $R^{12}$ may bond together to form a cyclic structure with the carbon and oxygen atoms to which they are attached, with the proviso that when the structure (Z-1), (Z-2) or (Z-3) is linked to the —(C=O)—O— linkage in recurring unit (7) via a linking group which is any one of $R^{2a}$, $R^{2b}$, $R^{3a}$, $R^{3b}$, $R^{5a}$, $R^{5b}$, $R^{6a}$, $R^{6b}$, $R^{7a}$, $R^{7b}$, $R^{8a}$, $R^{8b}$, $R^{9a}$, and $R^{9b}$, the linking group is an organic group as defined above, but having a valence bond as a result of one hydrogen atom being eliminated therefrom.

28. The protective coating composition of claim 27 wherein the solvent comprises a mixture of the ether compound and 0.1 to 90% by weight of an alcohol of 4 to 10 carbon atoms.

* * * * *